(12) United States Patent
Carson et al.

(10) Patent No.: US 7,589,104 B2
(45) Date of Patent: *Sep. 15, 2009

(54) TRICYCLIC-BRIDGED PIPERIDINYLINE DERIVATIVES AS §-OPIOID MODULATORS

(75) Inventors: John R. Carson, Norristown, PA (US); Scott L. Dax, Landenberg, PA (US); Bart DeCorte, Southhampton, PA (US); Li Liu, Doylestown, PA (US); Mark McDonnell, Lansdale, PA (US); James J. McNally, Souderton, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 11/313,704

(22) Filed: Dec. 21, 2005

(65) Prior Publication Data

US 2006/0135524 A1 Jun. 22, 2006

Related U.S. Application Data

(60) Provisional application No. 60/638,336, filed on Dec. 22, 2004.

(51) Int. Cl.
*C07D 405/04* (2006.01)
*A61K 31/46* (2006.01)

(52) U.S. Cl. .................................... 514/304; 546/126
(58) Field of Classification Search .................. 546/126; 514/304
See application file for complete search history.

(56) References Cited

U.S. PATENT DOCUMENTS

| | | | |
|---|---|---|---|
| 2,368,006 A | 1/1945 | Cusic | |
| 2,784,185 A | 3/1957 | Schuler | |
| 2,901,478 A | 8/1959 | Schuler | |
| 3,179,665 A | 4/1965 | Schmutz | |
| 3,305,547 A | 2/1967 | Stach et al. | |
| 3,470,188 A | 9/1969 | Kaiser et al. | |
| 3,557,287 A | 1/1971 | Berde et al. | |
| 3,931,232 A | 1/1976 | Bender et al. | |
| 3,987,042 A | 10/1976 | Gueremy et al. | |
| 4,086,350 A | 4/1978 | Zirkle | |
| 4,275,209 A | 6/1981 | Lassen et al. | |
| 4,356,184 A | 10/1982 | Deason et al. | |
| 4,666,907 A | 5/1987 | Fortin et al. | |
| 4,777,177 A | 10/1988 | Traber et al. | |
| 5,502,049 A | 3/1996 | Garret et al. | |
| 6,004,983 A | 12/1999 | Andersen et al. | |
| 6,114,354 A | 9/2000 | Andersen et al. | |
| 6,153,626 A | 11/2000 | Pelcman et al. | |
| 7,060,711 B2 | 6/2006 | Lubbert et al. | |
| 2003/0018447 A1 | 1/2003 | Florschuetz | |
| 2003/0166672 A1 | 9/2003 | Lubbert et al. | |
| 2005/0009860 A1* | 1/2005 | Carson et al. ............... 514/297 |
| 2006/0030585 A1* | 2/2006 | Dax et al. .................... 514/304 |
| 2006/0135522 A1* | 6/2006 | Carson et al. ............... 514/241 |
| 2006/0135524 A1 | 6/2006 | Carson et al. | |
| 2006/0135763 A1* | 6/2006 | Coats et al. .................... 544/43 |
| 2006/0148823 A1* | 7/2006 | Coats et al. ............ 514/255.05 |
| 2006/0287297 A1* | 12/2006 | DeCorte et al. ............. 514/216 |

FOREIGN PATENT DOCUMENTS

| | | |
|---|---|---|
| DE | 2009555 | 2/1970 |
| EP | 0005607 B1 | 11/1979 |
| EP | 1049676 B1 | 11/2000 |
| EP | 1306376 A1 | 5/2003 |
| EP | 1321169 A1 | 6/2003 |
| FR | 2290202 A1 | 6/1976 |
| GB | 1128734 | 10/1968 |
| WO | WO 98/28275 A1 | 7/1998 |
| WO | WO 9900376 A1 | 1/1999 |
| WO | WO 0146191 A1 | 6/2001 |
| WO | WO 0166543 A2 | 9/2001 |
| WO | WO 0172303 A1 | 10/2001 |
| WO | WO 02/36573 A2 | 5/2002 |
| WO | WO 0248122 A2 | 6/2002 |
| WO | WO 03035646 A2 | 5/2003 |
| WO | WO 2004026030 A2 | 4/2004 |
| WO | WO 2004035541 A1 | 4/2004 |
| WO | WO 2004/092165 A1 | 10/2004 |
| WO | WO 2005/003131 A1 | 1/2005 |

OTHER PUBLICATIONS

Zhang et. al. Journal of Medicinal Chemistry 1999, 42, 5455.*
Catalog Frontier Scientific Logan, Utah,online "http://www.frontiersci.com/browse.php?browse=Boronic%20acid" Apr. 2, 2007.*
Dorwald F. A. Side Reactions in Organic Synthesis, 2005; Wiley: VCH, Weinheim p. IX of Preface p. 1-15.*
West, Anthony R., Solid State Chemistry and its Applications, Wiley, New York, 1988, pp. 358 & 365.*

(Continued)

*Primary Examiner*—Rita J Desai
*Assistant Examiner*—David K O'Dell

(57) ABSTRACT

Disclosed are compounds, compositions and methods for treating various diseases and conditions, including pain. Such compounds are represented by Formula I as follows:

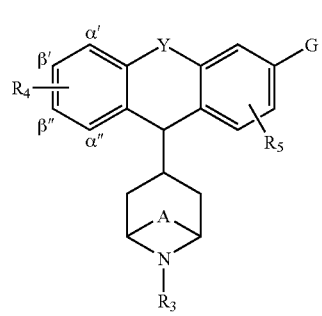

Formula (I)

wherein A, G, Y, $R_3$, $R_4$, and $R_5$ are defined herein.

19 Claims, No Drawings

OTHER PUBLICATIONS

Kaiser, C. et al., "Analogs of Phenothiazines. 5. Synthesis and Neuropharmacological Activity of Some Piperidytidene Derivatives of Thioxanthenes, Xanthenes, Dibenzoxepins, and Acridans", *J. Med. Chem.*, 1974, pp. 57-62, vol. 17, No. 1.

Wentland, M. et al., "8-Aminocyclazocine Analogues: Synthesis and Structure-Activity relationships", *Bioorganic & Med. Chem. Lett.*, 2000, pp. 183-187, vol. 10, No. 2.

Wentland, M. et al., "Selective Protection and Functionalization of Morphine: Synthesis and Opioid Receptor Binding Properties of 3-Amino-3-desoxymorphine Derivatives", *J. Med. Chem.* 2000, pp. 3558-3565, vol. 43, No. 19.

Wentland, M. et al., "3-Carboxamide Analogues of Morphine and Naltrexone: Synthesis and Opioid Receptor Binding Properties", *Bioorganic & Med. Chem. Lett.*, 2001, pp. 1717-1721, vol. 11.

Wentland, M. et al., "8-Carboxamidocyclazocine Analogues: Redefining the Structure-Activity Relationships of 2,6-Methano-3-benzazocines", *Bioorganic & Med. Chem. Lett.*, 2001, pp. 623-626, vol. 11.

Bidlack, J. M., "8-Carboxamidocyclazocine: A Long-Acting, Novel Benzomorphan", *J. Pharm. & Exp. Ther.* 2002, pp. 374-380, vol. 302, No. 1.

Wentland, M. et al., "Synthesis and Opioid Receptor Binding Affinities of 8-Amino-2,6-methano-3-benzazocines", *J. Med. Chem.* 2003, pp. 838-849, vol. 46.

Wentland, M. et al., "Redefining the Structure—Activity Relationships of 2,6-Methano-3-benzazocines. Part 2:8-Formamidocylclazocine Analogues". *Bioorganic & Med. Chem. Lett.* 2003, pp. 1911-1914, vol. 13.

Wentland, M. et al., "Thioformamido and Thiocarboxamido Derivatives of Cyclazocine: Syntheses and Opioid Receptor Bnding Properties", *Abstract of Papers, 226th ACS Natl. Mtg., N.Y.* 2003.

Zhang, A. et. al., "10-Ketomorphinan and 3-Substituted-3-desoxymorphinan Analogues as Mixed κ and μ Opioid Ligands: Synthesis and Biological Evaluation of Their Binding Affinity at Opioid Receptors", *J. Med. Chem.*, 2004, pp. 165-174, vol. 47, No. 1.

Kaiser, Carl. 'Analogs Phenothiazines. 5. Synthesis and Neuropharmacological Activity of Some Piperidylidene Derivatives of Thioxanthenes, Xanthenes, Dibenzoxephins, and Acridans' *J. Med. Chem.* (1974). vol. 17, No. 1, pp. 57-62.

Loughhead, David G. 'Unusual Reductions Induced by Formic Acid' *Tetrahedron Letters* (1988). vol. 29, No. 45, pp. 5701-5702.

Wentland, M. et al., "Redefining the structure-activity relationships of 2,6-methano-3-benzazocines. Part 3: 8-Thiocarboxamido and 8-thioformamido derivatives of cyclazocine", *Bioorganic & Med. Chem. Lett.*, 2005. pp. 2547-2551, vol. 15.

Wentland, M. et al., "Synthesis and opioid receptor binding properties of a highly potent 4-hydroxy analogue of naltrexone", *Bioorganic & Med. Chem. Lett.*, 2005, pp. 2107-2110.

Sun, X., et al. "Synthesis and Opioid Receiptor Binding Properties of Conformation-Rigidified Analogues of 8-Carboxamldocyclazocine and 8-Formamidocyclazocine", *Abstract of Papers, 229th ACS Natl. Mtg., N.Y.* 2005.

VanAtstine, M. A., "Synthesis and evaluation of novel N-substituted derivatives of 8-carboxamidocyclazocine", Abstact of papers 231st ACS National Meeting, Atlanta, GA, 2006, MEDI-009.

PCT International Search Report dated May 26, 2006 for PCT Application No. PCT/US2005/046692 which relates to U.S. Appl. No. 11/313,704 and a Written Opinion dated May 26, 2006.

Ananthan, S.: The AAPS Journal 2006, 8(1): E118-E125.

Berge, S.M. et al.: Pharmaceutical Salts; J. of Pharmaceutical Sciences (1977) 66(1): 1-19.

Biemans, H.A.M. et al.: Hexapyrrolylbenzene and Octapyrrolylnaphthalene; J. Org. Chem. (1996) 61: 9012-9015.

Boyd, R.E. et al.: Synthesis and Binding Affinities of 4-Diarylaminotropanes, a New Class of Delta Opioid Agonists; Bioorg. & Med. Chem. Letters (2000) 10: 1109-1111.

Calderon, S.N. et al.: SNC 80 and Related δ Opioid Agonists; Current Pharmaceutical Design (2004) 10: 733-742.

Calo, G. et al.: [Nphe$^1$,Arg$^{14}$,Lys$^{15}$]Nociceptin-NH$_2$, a novel potent and selective antagonist of the nociceptin/orphanin FQ receptor; British J. of Pharmacology (2002) 136: 303-311.

Carson, J.R. et al.: N-Alkyl-4-[(8-azabicyclo[3.2.1]-oct-3-ylident)phenylmethyl]-benzamides, μ and δ opioid agonists: a μ address; Bioorganic & Med. Chem. Letters (2004) 14: 2113-2116.

Chang, K.J. et al.: Benzomorphan Sites Are Ligand Recognition Sites of Putative ϵ-Receptors; Molecular Pharmacology (1984) 26: 484-488.

Commerical 2-Bromo-Phenols from Sigma-Aldrich.

Commerical 4-piperidinones.

Connor, M. et al.: Opioid Receptor Signalling Mechanisms; Clinical and Exper. Pharmacology and Physiology (1999) 26: 493-499.

Dorwald, F.Z.: Side Reactions in Organic Synthesis (2005) Wiley: VCH, Weinheim, p. 1X of Preface.

Dörwald, F.Z.: Side Reactions in Organic Synthesis (2005) Wiley: VCH, Weinheim p. 1X of Preface & Chapter 8: 279-308.

Erchegyi, J. et al.: Novel sst$_4$-Selective Somatostatin (SRIF) Agonists. 2. Analogues with β-Methyl-3-(2-naphthyl)alanine Substitutions at Position 8; J. Med. Chem. (2003) 46: 5587-5596.

Frontier Scientific Catalog (Logan, UT) Advanced Discovery Chemicals Pure (*and no so*) Simple 2006; Discover Chemicals A-F, H-I, M-N, P-Q and T.

Furness, M. S. et al.: Probes for Narcotic Receptor-Mediated Phenomena. 27.$^1$ Synthesis and Pharmacological Evaluation of Selective δ-Opioid Receptor Agonists from 4-[(αR)-α-(2 S,5R)-4-Substituted-2,5-dimethyl-1-piperazinyl-3-methoxybenzyl]-N,N-diethylbenzamides and Their Enantiomers; J. Med. Chem. (2000) 43: 3193-3196.

Gilbert, P.E. et al.: The Effects of Morphine- And Nalorphine—Like Drugs in the Nondependent, Morphine-Dependent and Cyclazocine-Dependent Chronic Spinal Dog; The J. of Pharm. And Exp. Thera. (1976) 198(1): 66-82.

Gould, P.L.: Salt selection for basic drugs; Intl J. of Pharmaceutics (1986) 33: 201-217.

Gribble, G.W. et al.: Sodium Triacetoxyborohydride$^1$; Encyclopedia of Reagents for Organic Synthesis online @ http://www.mrw.interscience.wiley.com/eros/articles/rs112/sect0.html Apr. 24, 2007.

Gross, R.A. et al.: Dynorphin A and cAMP-dependent protein kinase independently regulate neuronal calcium currents; Proc. Natl. Acad. Sci. (1990) 87: 7025-7029.

Hancock, B.C. et al.: Characteristics and Significance of the Amorphous State in Pharmaceutical Systems; J. of Pharm. Sciences, (Jan. 1997) 86(1): 1-12.

Hutchins, R.O. et al.: Selective Reductive Displacement of Alkyl Halides and Sulfonate Esters with Cyanoborohydride Reagents in Hexamethylphosphoramide; J. Org. Chem. (1977) 42(1): 82-91.

Jones, M. JR.: Organic Chemistry Norton, New York (1997): 578-591.

Kenakin, T. et al.: The ligand paradox between affinity and efficacy: can you be there and not make a difference?; Trends in Pharm. Sciences (2002) 23(6): 275-280.

Kruszynski, R. et al.: Novel endomorphin-2 analogs with μ-opioid receptor antagonist activity; J. of Peptide Research (2005) 66: 125-131.

Le Bars, D. et al.: Animal Models of Nociception; Pharmacological Reviews (2001) 53(4): 597-652.

Lord, John A.H. et al.: Endogenous opioid peptides: multiple agonists and receptors; Nature (1977) 267: 495-499.

Mansour, A. et al.: Anatomy of CNS opioid receptors; Trends in Neuroscience (1988) 11(7): 308-314.

Nieschulz, O. et al.: Pharmacological studies on 10-(1-methyl-3-piperidyl)-2 methoxyphenthiazine and related compounds; Arzneimittel-Forschung (1960) 10: 156-165.

Pert, C.B. et al.: Opiate Receptor: Demonstration in Nervous Tissue; Science (1973) 179: 1011-1014.

Pozharskii, A.F. et al.: Molecular Rings Studded With Jewels; Heterocycles in Life and Society, Wiley (1997): 1-6.

Quock, R.M. et al.: The δ-Opioid Receptor: Molecular Pharmacology, Signal Transduction, and the Determination of Drug Efficacy; Pharmacological Reviews (1999) 51(3): 503-532.

Sharma, S.K. et al.: Dual regulation of adenylate cyclase accounts for narcotic dependence and tolerance; Proc. Natl. Acad. Sci. (1975) 72(8): 3092-3096.

Still, W. Clark et al.: Rapid Chromatographic Technique for Preparative Separations with Moderate Resolution; J. Org. Chem. (1978) 43(14): 2923-2925.

Structures in copending U.S. Appl. No. 11/195,231.

Tao, M. et al.: Synthesis and structure-activity relationships of novel poly(ADP-ribose) polymerase-1 inhibitors; Bioorg. & Med. Chem. Letters (2006) 16: 938-942.

Thomas, J.B. et al.: 4-[(8-Alkyl-8-azabicyclo[3.2.1]octyl-3-yl)-3-arylanilino]-N,N-diethylbenzamides: Displays High Affinity, Selective Ligands for the Delta Opioid Receptor Illustrate Factors Important to Antagonist Activity; Bioorg. & Med. Chem. Letters (2000) 10(11): 1281-1284.

Thomas, J.B. et al.: (±)-4-[(N-Allyl-CIS-3-Methyl-4-Piperidinyl)Phenylamino]-N,N-Diethylbenzamide Displays Selective Binding for the Delta Opioid Receptor; Bioorg. & Med. Chem. Letters (1999) 9(20): 3053-3056.

Thomas, J.B. et al.: Factors Influencing Agonist Potency and Selectivity for the Opioid δ Receptor Are Revealed in Structure—Activity Relationship Studies of the 4-[(N-Substituted-4-piperidinyl)arylamino]-N,N-diethylbenzamides; J. Med. Chem. (2001) 44(6): 972-987.

Truce, W. E. et al.: The Smiles and Related Rearrangements of Aromatic Systems; Organic Reactions (1970) 18: 99-215.

Walpole, C.S.J. et al.: The Discovery of Capsazepine, the First Competitive Antagonist of the Sensory Neuron Excitants Capsaicin and Resiniferatoxin; J. Med. Chem. (1994) 37: 1942-1954.

West, A.R.: Solid State Chemistry and its Applications, Wiley, New York, 1988: 358 & 365.

Wollemann, M.: Recent Developments in the Research of Opioid Receptor Subtype Molecular Characterization; J. of Neurochemistry (1990) 54(4): 1095-1101.

\* cited by examiner

TRICYCLIC-BRIDGED PIPERIDINYLINE DERIVATIVES AS δ-OPIOID MODULATORS

CROSS-REFERENCE TO RELATED APPLICATIONS

This application claims benefit to U.S. Provisional Application Ser. No. 60/638,336, filed Dec. 22, 2004, incorporated herein by reference in its entirety.

STATEMENT REGARDING FEDERALLY SPONSORED RESEARCH OR DEVELOPMENT

The research and development of the invention described below was not federally sponsored.

BACKGROUND OF THE INVENTION

The term "opiate" has been used to designate pharmacologically active alkaloids derived from opium, e.g., morphine, codeine, and many semi-synthetic congeners of morphine. After the isolation of peptide compounds with morphine-like actions, the term opioid was introduced to refer generically to all drugs with morphine-like actions. Included among opioids are various peptides that exhibit morphine-like activity, such as endorphins, enkephalins and dynorphins. However, some sources use the term "opiate" in a generic sense, and in such contexts, opiate and opioid are interchangeable. Additionally, the term opioid has been used to refer to antagonists of morphine-like drugs as well as to characterize receptors or binding sites that combine with such agents.

Opioids are generally employed as analgesics, but they may have many other pharmacological effects as well. Morphine and related opioids produce certain of their major effects on the central nervous and digestive systems. The effects are diverse, including analgesia, drowsiness, mood changes, respiratory depression, dizziness, mental clouding, dysphoria, pruritus, increased pressure in the biliary tract, decreased gastrointestinal motility, nausea, vomiting, and alterations of the endocrine and autonomic nervous systems.

When therapeutic doses of morphine are given to patients with pain, they report that the pain is less intense, less discomforting, or entirely gone. In addition to experiencing relief of distress, some patients experience euphoria. However, when morphine in a selected pain-relieving dose is given to a pain-free individual, the experience is not always pleasant; nausea is common, and vomiting may also occur. Drowsiness, inability to concentrate, difficulty in mentation, apathy, lessened physical activity, reduced visual acuity, and lethargy may ensue.

Two distinct classes of opioid molecules can bind opioid receptors: the opioid peptides (e.g., the enkephalins, dynorphins, and endorphins) and the alkaloid opiates (e.g., morphine, etorphine, diprenorphine and naloxone). Subsequent to the initial demonstration of opiate binding sites (Pert, C. B. and Snyder, S. H., Science (1973) 179:1011-1014), the differential pharmacological and physiological effects of both opioid peptide analogues and alkaloid opiates served to delineate multiple opioid receptors. Accordingly, three molecularly and pharmacologically distinct opioid receptor types have been described: delta, kappa and mu. Furthermore, each type is believed to have sub-types (Wollemann, M., J Neurochem (1990) 54:1095-1101; Lord, J. A., et al., Nature (1977) 267:495-499).

All three of these opioid receptor types appear to share the same functional mechanisms at a cellular level. For example, the opioid receptors cause inhibition of adenylate cyclase, and inhibition of neurotransmitter release via both potassium channel activation and inhibition of $Ca^{2+}$ channels (Evans, C. J., In: Biological Basis of Substance Abuse, S. G. Korenman & J. D. Barchas, eds., Oxford University Press (in press); North, A. R., et al., Proc Natl Acad Sci USA (1990) 87:7025-29; Gross, R. A., et al., Proc Natl Acad Sci USA (1990) 87:7025-29; Sharma, S. K., et al., Proc Natl Acad Sci USA (1975) 72:3092-96). Although the functional mechanisms are the same, the behavioral manifestations of receptor-selective drugs differ greatly (Gilbert, P. E. & Martin, W. R., J Pharmacol Exp Ther (1976) 198:66-82). Such differences may be attributable in part to the anatomical location of the different receptors.

Delta receptors have a more discrete distribution within the mammalian CNS than either mu or kappa receptors, with high concentrations in the amygdaloid complex, striatum, substantia nigra, olfactory bulb, olfactory tubercles, hippocampal formation, and the cerebral cortex (Mansour, A., et al., Trends in Neurosci (1988) 11:308-14). The rat cerebellum is remarkably devoid of opioid receptors including delta opioid receptors.

D. Delorme, E. Roberts and Z. Wei, World Patent WO/28275 (1998) discloses diaryl methylidenylpiperidines that are opioid analgesics, but does not disclose or suggest the compounds of the present invention.

C. Kaiser, and others (J. Med. Chem. 1974, Volume 17, pages 57-61) disclose some piperidylidene derivatives of thioxanthenes, xanthenes, dibenoxepins and acridans that are neuroleptic agents. These authors, however, do not disclose or suggest either the structure or the activity of the compounds of the present invention.

British Patent GB 1128734 (1966) discloses derivatives of 6,11-dihydrodibenzo[b,e]oxepine that are anticholinergic, anti-convulsive, muscle-relaxing, sedating, diuretic, and/or vasoactive agents. These, agents, however, differ significantly from the compounds of the present invention both structurally and pharmacologically.

There is a continuing need for new delta opioid receptor modulators as analgesics. There is a further need for delta opioid receptor selective agonists as analgesics having reduced side effects. There is also a need for delta opioid receptor antagonists as immunosuppressants, antiinflammatory agents, agents for the treatment of neurological and psychiatric conditions, agents for the treatment of urological and reproductive conditions, medicaments for drug and alcohol abuse, agents for treating gastritis and diarrhea, cardiovascular agents and agents for the treatment of respiratory diseases, having reduced side effects.

SUMMARY OF THE INVENTION

The present invention is directed, inter alia, to compounds of Formula (I) and compositions comprising a compound of Formula (I):

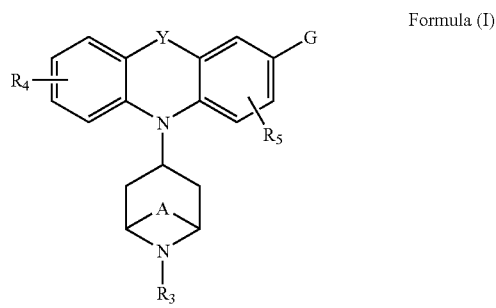

Formula (I)

wherein:
G is —C(Z)N($R_1$)$R_2$, $C_{6-10}$aryl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, furyl, indazolyl, indolyl, indolinyl, isothiazolyl, isoxazolyl, oxazolyl, isoxadiazolyl, benzoxazolyl, quinolinyl, isoquinolinyl, and pyridinyl; wherein aryl and the heterocycles of G are optionally substituted with one to three substituents independently selected from the group consisting of $C_{1-8}$alkanyl, $C_{2-8}$alkenyl, $C_{2-8}$alkynyl, $C_{1-8}$alkanyloxy, hydroxy($C_{1-8}$) alkanyl, carboxy($C_{1-8}$)alkanyl, $C_{1-8}$alkanylcarbonylamino, halogen, hydroxy, cyano, nitro, oxo, thioxo, amino, $C_{1-6}$alkanylamino, di($C_{1-6}$alkanyl)amino, $C_{1-8}$alkanylthio, $C_{1-8}$alkanylsulfonyl, $C_{1-8}$alkanylsulfonylamino, aminocarbonyl, aminothiocarbonyl, aminocarbonylamino, aminothiocarbonylamino, $C_{1-8}$alkanylaminocarbonyl, di($C_{1-8}$alkanyl)aminocarbonyl, and $C_{1-6}$alkanyloxycarbonylamino;

$R_1$ is a substituent selected from the group consisting of hydrogen, $C_{1-8}$alkanyl, $C_{2-8}$alkenyl, and $C_{2-8}$alkynyl;

$R_2$ is a substituent selected from the group consisting of hydrogen; $C_{1-8}$alkanyl; $C_{2-8}$alkenyl; $C_{2-8}$alkynyl; $C_{6-10}$aryl; and $C_{1-8}$cycloalkanyl; wherein $C_{1-8}$alkanyl is optionally substituted with one to three substituents independently selected from the group consisting of phenyl, amino, $C_{1-6}$alkanylamino, di($C_{1-6}$alkanyl)amino, $C_{1-6}$alkanyloxy, thio$C_{1-6}$alkanyloxy, hydroxy, fluoro, chloro, cyano, aminocarbonyl, $C_{1-8}$alkanylaminocarbonyl, di($C_{1-8}$alkanyl)aminocarbonyl, $C_{1-6}$alkanyloxycarbonyl, and aryloxy; and wherein any aryl-containing substituents and $C_{1-8}$cycloalkanyl substituents of $R_2$ are optionally substituted with one to three substituents independently selected from the group consisting of $C_{1-8}$alkanyl, $C_{2-8}$alkenyl, $C_{2-8}$alkynyl, $C_{1-8}$alkanyloxy, trifluoromethyl, trifluoromethoxy, phenyl, halogen, cyano, hydroxy, $C_{1-8}$alkanylthio, $C_{1-8}$alkanylsulfonyl, and $C_{1-8}$alkanylsulfonylamino;

or $R_1$ and $R_2$ taken together with the nitrogen to which they are attached form a 5-7 membered cycloheteroalkyl optionally substituted with one to three substituents independently selected from the group consisting of $C_{1-8}$alkanyl, hydroxy($C_{1-8}$)alkanyl, hydroxy, amino, $C_{1-6}$alkanylamino, di($C_{1-6}$alkanyl)amino, and halogen;

$R_3$ is a substituent selected from the group consisting of hydrogen, $C_{1-8}$alkanyl, halo$_{1-3}$($C_{1-8}$)alkanyl, $C_{2-8}$alkenyl, $C_{2-8}$alkynyl, $C_{3-8}$cycloalkanyl, cycloalkanyl($C_{1-8}$) alkanyl, $C_{1-8}$alkanyloxy($C_{1-8}$)alkanyl, $C_{1-8}$alkanylthio($C_{1-8}$)alkanyl, hydroxy$C_{1-8}$alkanyl, $C_{1-8}$alkanyloxycarbonyl, halo$_{1-3}$($C_{1-8}$)alkanylcarbonyl, formyl, thioformyl, carbamimidoyl, phenylimino($C_{1-8}$)alkanyl, phenyl($C_{1-8}$)alkanyl, phenyl($C_{1-8}$)alkenyl, phenyl($C_{1-8}$)alkynyl, naphthyl($C_{1-8}$)alkanyl and heteroaryl($C_{1-8}$)alkanyl wherein the heteroaryl is selected from the group consisting of benzo[1,3]dioxolyl, imidazolyl, furanyl, pyridinyl, thienyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, tetrazolyl, thiazolyl; wherein phenyl, naphthyl and heteroaryl are optionally substituted with one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl, thioureido, and fluoro($C_{1-6}$)alkanyloxy; alternatively, when phenyl and heteroaryl are optionally substituted with alkanyl or alkanyloxy substituents attached to adjacent carbon atoms, the two substituents can together form a fused cyclic alkanyl or cycloheteroalkanyl selected from the group consisting of —(CH$_2$)$_{3-5}$—, —O(CH$_2$)$_{2-4}$—, —(CH$_2$)$_{2-4}$O—, and —O(CH$_2$)$_{1-3}$O—;

$R_4$ is one to three substituents independently selected from the group consisting of hydrogen; $C_{1-6}$alkanyl; $C_{2-6}$alkenyl; $C_{2-6}$alkynyl; aryl($C_{2-6}$)alkynyl; $C_{1-6}$alkanyloxy; amino; $C_{1-6}$alkanylamino; di($C_{1-6}$alkanyl)amino; $C_{6-10}$arylamino wherein aryl is optionally substituted with one to three substitutents independently selected from the group consisting of $C_{1-6}$alkanyl, $C_{1-6}$alkoxy, halogen, and hydroxy; formylamino; pyridinylamino; $C_{1-6}$alkanylcarbonyl; $C_{1-6}$alkanylcarbonyloxy; $C_{1-6}$alkanyloxycarbonyl; aminocarbonyl; $C_{1-6}$alkanylaminocarbonyl; di($C_{1-6}$alkanyl)aminocarbonyl; $C_{1-6}$alkanylcarbonylamino; $C_{1-6}$alkanylthio; $C_{1-6}$alkanylsulfonyl; halogen; hydroxy; cyano; hydroxycarbonyl; $C_{6-10}$aryl; chromanyl; chromenyl; furanyl; imidazolyl; indazolyl; indolyl; indolinyl; isoindolinyl; isoquinolinyl; isothiazolyl; isoxazolyl; naphthyridinyl; oxazolyl; pyrazinyl; pyrazolyl; pyridazinyl; pyridinyl; pyrimidinyl; pyrrolyl; quinazolinyl; quinolinyl; quinolizinyl; quinoxalinyl; tetrazolyl; thiazolyl; thienyl; fluoroalkanyl; and fluoroalkanyloxy; or optionally, when $R_4$ is two substituents attached to adjacent carbon atoms, the two substituents together form a single fused moiety, wherein the fused moiety is —(CH$_2$)$_{3-5}$—, —O(CH$_2$)$_{2-4}$—, —(CH$_2$)$_{2-4}$O—, —O(CH$_2$)$_{1-3}$O—, or —S—C(NH$_2$)=N—;

$R_5$ is one to two substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl and fluoro($C_{1-6}$)alkanyloxy;

A is —(CH$_2$)$_m$—, wherein m is 2 or 3;

Y is O or S;

Z is O, S, NH, N($C_{1-6}$alkanyl), N(OH), N(O$C_{1-6}$alkanyl), or N(phenyl); and enantiomers, diastereomers, tautomers, solvates, or pharmaceutically acceptable salts thereof.

In certain embodiments, wherein G is pyridin-3-yl, furan-3-yl, thien-3-yl, or quinolin-3-yl and $R^3$ is hydrogen, $R^4$ is not hydrogen; and when G is N,N-diethylaminocarbonyl and $R^3$ is methyl, $R^4$ is not hydrogen; and when G is N,N-diethylaminocarbonyl and $R^3$ is hydrogen, $R^4$ is not α'-chloro.

Finally, the present invention is directed, inter alia, to veterinary and pharmaceutical compositions containing compounds of Formula (I) wherein the compositions are used to treat mild to severe pain in warm-blooded animals.

DETAILED DESCRIPTION OF THE INVENTION

As used herein, the following underlined terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms "Alkyl:" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1- en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl", "alkenyl" and/or "alkynyl" is used, as defined below. In preferred embodiments, the alkyl groups are ($C_1$-$C_6$) alkyl, with ($C_1$-$C_3$) being particularly preferred.

"Alkanyl:" refers to a saturated branched, straight-chain or cyclic monovalent hydrocarbon radical derived by the removal of one hydrogen atom from a single carbon atom of a parent alkane. Typical alkanyl groups include, but are not limited to, methanyl; ethanyl; propanyls such as propan-1-yl, propan-2-yl, cyclopropan-1-yl, etc.; butyanyls such as butan-1-yl, butan-2-yl, 2-methyl-propan-1-yl, 2-methyl-propan-2-yl, cyclobutan-1-yl, etc.; and the like. In preferred embodiments, the alkanyl groups are ($C_{1-8}$) alkanyl, with ($C_{1-3}$) being particularly preferred.

"Alkenyl" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Heteroalkyl" and Heteroalkanyl" refer to alkyl or alkanyl radicals, respectively, in which one or more carbon atoms (and any necessary associated hydrogen atoms) are independently replaced with the same or different heteroatoms (including any necessary hydrogen or other atoms). Typical heteroatoms to replace the carbon atom(s) include, but are not limited to, N, P, O, S, Si, etc. Preferred heteroatoms are O, N and S. Thus, heteroalkanyl radicals can contain one or more of the same or different heteroatomic groups, including, by way of example and not limitation, epoxy (—O—), epidioxy (—O—O—), thioether (—S—), epidithio (—SS—), epoxythio (—O—S—), epoxyimino (—O—NR'—), imino (—NR'—), biimino (—NR'—NR'—), azino (=N—N=), azo (—N=N—), azoxy (—N—O—N—), azimino (—NR'—N=N—), phosphano (—PH—), $\lambda^4$-sulfano (—SH$_2$—), sulfonyl (—S(O)$_2$—), and the like, where each R' is independently hydrogen or ($C_1$-$C_6$) alkyl.

"Parent Aromatic Ring System:" refers to an unsaturated cyclic or polycyclic ring system having a conjugated π electron system. Specifically included within the definition of "parent aromatic ring system" are fused ring systems in which one or more rings are aromatic and one or more rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like "Aryl:" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is ($C_{5-20}$) aryl, with ($C_{5-10}$) being particularly preferred. Particularly preferred aryl groups are phenyl and naphthyl groups.

"Arylalkyl:" refers to an acyclic alkyl group in which one of the hydrogen atoms bonded to a carbon atom, typically a terminal carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. [In preferred embodiments, the arylalkyl group is ($C_{6-26}$) arylalkyl, e.g., the alkanyl, alkenyl or alkynyl moiety of the arylalkyl group is ($C_{1-6}$) and the aryl moiety is ($C_{5-20}$). In particularly preferred embodiments the arylalkyl group is ($C_{6-13}$), e.g., the alkanyl, alkenyl or alkynyl moiety of the arylalkyl group is ($C_{1-3}$) and the aryl moiety is ($C_{5-10}$). Even more preferred arylalkyl groups are phenylalkanyls.

"Alkanyloxy:" refers to a saturated branched, straight-chain or cyclic monovalent hydrocarbon alcohol radical derived by the removal of the hydrogen atom from the hydroxide oxygen of the alcohol. Typical alkanyloxy groups include, but are not limited to, methanyloxy; ethanyloxy; propanyloxy groups such as propan-1-yloxy ($CH_3CH_2CH_2O$—), propan-2-yloxy (($CH_3$)$_2$CHO—), cyclopropan-1-yloxy, etc.; butanyloxy groups such as butan-1-yloxy, butan-2-yloxy, 2-methyl-propan-1-yloxy, 2-methyl-propan-2-yloxy, cyclobutan-1-yloxy, etc.; and the like. In preferred embodiments, the alkanyloxy groups are ($C_{1-8}$) alkanyloxy groups, with ($C_{1-3}$) being particularly preferred.

"Parent Heteroaromatic Ring System:" refers to a parent aromatic ring system in which one carbon atom is replaced with a heteroatom. Heteroatoms to replace the carbon atoms include N, O, and S. Specifically included within the definition of "parent heteroaromatic ring systems" are fused ring systems in which one or more rings are aromatic and one or more rings are saturated or unsaturated, such as, for example, arsindole, chromane, chromene, indole, indoline, xanthene, etc. Typical parent heteroaromatic ring systems include, but are not limited to, carbazole, imidazole, indazole, indole, indoline, indolizine, isoindole, isoindoline, isoquinoline, isothiazole, isoxazole, naphthyridine, oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl:" refers to a monovalent heteroaromatic radical derived by the removal of one hydrogen atom from a single atom of a parent heteroaromatic ring system. Typical heteroaryl groups include, but are not limited to, radicals derived from carbazole, imidazole, indazole, indole, indoline, indolizine, isoindole, isoindoline, isoquinoline, isothiazole, isoxazole, naphthyridine, oxadiazole, oxazole, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-20 membered heteroaryl, with 5-10 membered heteroaryl being particularly preferred.

"Cycloheteroalkyl:" refers to a saturated or unsaturated monocyclic or bicyclic alkyl radical in which one carbon atom is replaced with N, O or S. In certain specified embodiments the cycloheteroalkyl may contain up to four heteroatoms independently selected from N, O or S. Typical cycloheteroalkyl moieties include, but are not limited to, radicals derived from imidazolidine, morpholine, piperazine, piperidine, pyrazolidine, pyrrolidine, quinuclidine, and the like. In preferred embodiments, the cycloheteroalkyl is a 3-6 membered cycloheteroalkyl.

"Cycloheteroalkanyl:" refers to a saturated monocyclic or bicyclic alkanyl radical in which one carbon atom is replaced with N, O or S. In certain specified embodiments the cycloheteroalkanyl may contain up to four heteroatoms independently selected from N, O or S. Typical cycloheteroalkanyl moieties include, but are not limited to, radicals derived from imidazolidine, morpholine, piperazine, piperidine, pyrazolidine, pyrrolidine, quinuclidine, and the like. In preferred embodiments, the cycloheteroalkanyl is a 3-6 membered cycloheteroalkanyl.

"Cycloheteroalkenyl:" refers to a saturated monocyclic or bicyclic alkenyl radical in which one carbon atom is replaced with N, O or S. In certain specified embodiments the cycloheteroalkenyl may contain up to four heteroatoms independently selected from N, O or S. Typical cycloheteroalkenyl moieties include, but are not limited to, radicals derived from imidazoline, pyrazoline, pyrroline, indoline, pyran, and the like. In preferred embodiments, the cycloheteroalkanyl is a 3-6 membered cycloheteroalkanyl.

"Substituted:" refers to a radical in which one or more hydrogen atoms are each independently replaced with the same or different substituent(s). Typical substituents include, but are not limited to, —X, —R, —O⁻, =O, —OR, —O—OR, —SR, —S⁻, =S, —NRR, =NR, —CX$_3$, —CN, —OCN, —SCN, —NCO, —NCS, —NO, —NO$_2$, =N$_2$, —N$_3$, —NHOH, —S(O)$_2$O⁻, —S(O)$_2$OH, —S(O)$_2$R, —P(O)(O⁻)$_2$, —P(O)(OH)$_2$, —C(O)R, —C(O)X, —C(S)R, —C(S)X, —C(O)OR, —C(O)O⁻, —C(S)OR, —C(O)SR, —C(S)SR, —C(O)NRR, —C(S)NRR and —C(NR)NRR, where each X is independently a halogen (preferably —F, —Cl or —Br) and each R is independently —H, alkyl, alkanyl, alkenyl, alkynyl, alkylidene, alkylidyne, aryl, arylalkyl, arylheteroalkyl, heteroaryl, heteroarylalkyl or heteroaryl-heteroalkyl, as defined herein. Preferred substituents include hydroxy, halogen, C$_{1-8}$alkyl, C$_{1-8}$alkanyloxy, fluorinated alkanyloxy, fluorinated alkyl, C$_{1-8}$alkylthio, C$_{3-8}$cycloalkyl, C$_{3-8}$cycloalkanyloxy, nitro, amino, C$_{1-8}$alkylamino, C$_{1-8}$dialkylamino, C$_{3-8}$cycloalkylamino, cyano, carboxy, C$_{1-7}$alkanyloxycarbonyl, C$_{1-7}$alkylcarbonyloxy, formyl, carbamoyl, phenyl, aroyl, carbamoyl, amidino, (C$_{1-8}$alkylamino)carbonyl, (arylamino)carbonyl and aryl(C$_{1-8}$alkyl)carbonyl.

With reference to substituents, the term "independently" means that when more than one of such substituent is possible, such substituents may be the same or different from each other.

Throughout this disclosure, the terminal portion of the designated side chain is described first, followed by the adjacent functionality toward the point of attachment. Thus, for example, a "phenylC$_{1-6}$alkanylaminocarbonylC$_{1-6}$alkyl" substituent refers to a group of the formula

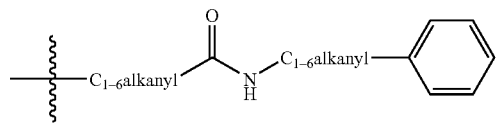

The present invention is directed, inter alia, to compounds of Formula (I) and compositions comprising a compound of Formula (I):

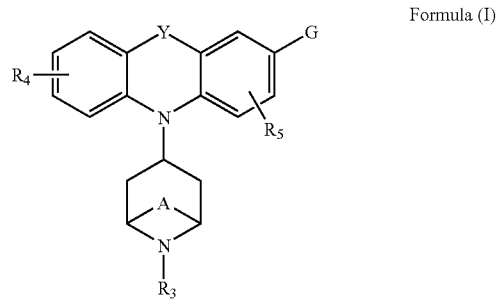

Formula (I)

wherein:
G is —C(Z)N(R$_1$)R$_2$, C$_{6-10}$aryl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, furyl, indazolyl, indolyl, indolinyl, isothiazolyl, isoxazolyl, oxazolyl, isoxadiazolyl, benzoxazolyl, quinolinyl, isoquinolinyl, and pyridinyl; wherein aryl and the heterocycles of G are optionally substituted with one to three substituents independently selected from the group consisting of C$_{1-8}$alkanyl, C$_{2-8}$alkenyl, C$_{2-8}$alkynyl, C$_{1-8}$alkanyloxy, hydroxy (C$_{1-8}$)alkanyl, carboxy(C$_{1-8}$)alkanyl, C$_{1-8}$alkanylcarbonylamino, halogen, hydroxy, cyano, nitro, oxo, thioxo, amino, C$_{1-6}$alkanylamino, di(C$_{1-6}$alkanyl)amino, C$_{1-8}$alkanylthio, C$_{1-8}$alkanylsulfonyl, C$_{1-8}$alkanylsulfonylamino, aminocarbonyl, aminothiocarbonyl, aminocarbonylamino, aminothiocarbonylamino, C$_{1-8}$alkanylaminocarbonyl, di(C$_{1-8}$alkanyl)aminocarbonyl, and C$_{1-6}$alkanyloxycarbonylamino;
R$_1$ is a substituent selected from the group consisting of hydrogen, C$_{1-8}$alkanyl, C$_{2-8}$alkenyl, and C$_{2-8}$alkynyl;
R$_2$ is a substituent selected from the group consisting of hydrogen; C$_{1-8}$alkanyl; C$_{2-8}$alkenyl; C$_{2-8}$alkynyl; C$_{6-10}$aryl; and C$_{1-8}$cycloalkanyl; wherein C$_{1-8}$alkanyl is optionally substituted with one to three substituents independently selected from the group consisting of phenyl, amino, C$_{1-6}$alkanylamino, di(C$_{1-6}$alkanyl)amino, C$_{1-6}$alkanyloxy, thioC$_{1-6}$alkanyloxy, hydroxy, fluoro, chloro, cyano, aminocarbonyl, C$_{1-8}$alkanylaminocarbonyl, di(C$_{1-8}$alkanyl)aminocarbonyl, C$_{1-6}$alkanyloxycarbonyl, and aryloxy; and wherein any aryl-containing substituents and $C_{1-8}$cycloalkanyl substituents of $R_2$ are optionally substituted with one to three substituents independently selected from the group consisting of $C_{1-8}$alkanyl, $C_{2-8}$alkenyl, $C_{2-8}$alkynyl, $C_{1-8}$alkanyloxy, trifluoromethyl, trifluoromethoxy, phenyl, halogen, cyano, hydroxy, $C_{1-8}$alkanylthio, $C_{1-8}$alkanylsulfonyl, and $C_{1-8}$alkanylsulfonylamino;

or $R_1$ and $R_2$ taken together with the nitrogen to which they are attached form a 5-7 membered cycloheteroalkyl optionally substituted with one to three substituents independently selected from the group consisting of $C_{1-8}$alkanyl, hydroxy($C_{1-8}$)alkanyl, hydroxy, amino, $C_{1-6}$alkanylamino, di($C_{1-6}$alkanyl)amino, and halogen;

$R_3$ is a substituent selected from the group consisting of hydrogen, $C_{1-8}$alkanyl, halo$_{1-3}(C_{1-8})$alkanyl, $C_{2-8}$alkenyl, $C_{2-8}$alkynyl, $C_{3-8}$cycloalkanyl, cycloalkanyl($C_{1-8}$)alkanyl, $C_{1-8}$alkanyloxy($C_{1-8}$)alkanyl, $C_{1-8}$alkanylthio($C_{1-8}$)alkanyl, hydroxy$C_{1-8}$alkanyl, $C_{1-8}$alkanyloxycarbonyl, halo$_{1-3}(C_{1-8})$alkanylcarbonyl, formyl, thioformyl, carbamimidoyl, phenylimino($C_{1-8}$)alkanyl, phenyl($C_{1-8}$)alkanyl, phenyl($C_{1-8}$)alkenyl, phenyl($C_{1-8}$)alkynyl, naphthyl($C_{1-8}$)alkanyl and heteroaryl ($C_{1-8}$)alkanyl wherein the heteroaryl is selected from the group consisting of benzo[1,3]dioxolyl, imidazolyl, furanyl, pyridinyl, thienyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, tetrazolyl, thiazolyl; wherein phenyl, naphthyl and heteroaryl are optionally substituted with one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl, thioureido, and fluoro($C_{1-6}$)alkanyloxy; alternatively, when phenyl and heteroaryl are optionally substituted with alkanyl or alkanyloxy substituents attached to adjacent carbon atoms, the two substituents can together form a fused cyclic alkanyl or cycloheteroalkanyl selected from the group consisting of —$(CH_2)_{3-5}$—, —$O(CH_2)_{2-4}$—, —$(CH_2)_{2-4}O$—, and —$O(CH_2)_{1-3}O$—;

$R_4$ is one to three substituents independently selected from the group consisting of hydrogen; $C_{1-6}$alkanyl; $C_{2-6}$alkenyl; $C_{2-6}$alkynyl; aryl($C_{2-6}$)alkynyl; $C_{1-6}$alkanyloxy; amino; $C_{1-6}$alkanylamino; di($C_{1-6}$alkanyl)amino; $C_{6-10}$arylamino wherein aryl is optionally substituted with one to three substitutents independently selected from the group consisting of $C_{1-6}$alkanyl, $C_{1-6}$alkoxy, halogen, and hydroxy; formylamino; pyridinylamino; $C_{1-6}$alkanylcarbonyl; $C_{1-6}$alkanylcarbonyloxy; $C_{1-6}$alkanyloxycarbonyl; aminocarbonyl; $C_{1-6}$alkanylaminocarbonyl; di($C_{1-6}$alkanyl)aminocarbonyl; $C_{1-6}$alkanylcarbonylamino; $C_{1-6}$alkanylthio; $C_{1-6}$alkanylsulfonyl; halogen; hydroxy; cyano; hydroxycarbonyl; $C_{6-10}$aryl; chromanyl; chromenyl; furanyl; imidazolyl; indazolyl; indolyl; indolinyl; isoindolinyl; isoquinolinyl; isothiazolyl; isoxazolyl; naphthyridinyl; oxazolyl; pyrazinyl; pyrazolyl; pyridazinyl; pyridinyl; pyrimidinyl; pyrrolyl; quinazolinyl; quinolinyl; quinolizinyl; quinoxalinyl; tetrazolyl; thiazolyl; thienyl; fluoroalkanyl; and fluoroalkanyloxy; or optionally, when $R_4$ is two substituents attached to adjacent carbon atoms, the two substituents together form a single fused moiety, wherein the fused moiety is —$(CH_2)_{3-5}$—, —$O(CH_2)_{2-4}$—, —$(CH_2)_{2-4}O$—, —$O(CH_2)_{1-3}O$—, or —S—C(NH$_2$)═N—;

$R_5$ is one to two substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl and fluoro($C_{1-6}$)alkanyloxy;

A is —$(CH_2)_m$—, wherein m is 2 or 3;

Y is O or S;

Z is O, S, NH, N($C_{1-6}$alkanyl), N(OH), N(O$C_{1-6}$alkanyl), or N(phenyl); and enantiomers, diastereomers, tautomers, solvates, or pharmaceutically acceptable salts thereof.

In certain embodiments, the present invention is directed, inter alia, to compounds of Formula (I) and compositions comprising a compound of Formula (I): provided that when G is pyridin-3-yl, furan-3-yl, thien-3-yl, or quinolin-3-yl and $R^3$ is hydrogen, $R^4$ is not hydrogen; and provided that when G is N,N-diethylaminocarbonyl and $R^3$ is methyl, $R^4$ is not hydrogen; and provided that when G is N,N-diethylaminocarbonyl and $R^3$ is hydrogen, $R^4$ is not α'-chloro.

An embodiment of the present invention is directed to a compound of Formula (I) wherein the structure is numbered as defined herein and the substituents are as defined herein.

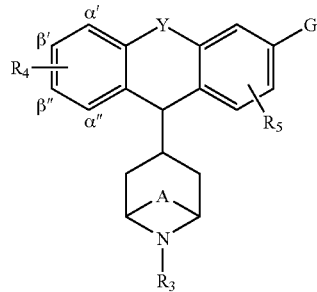

Formula (I)

The present invention is also directed, inter alia, to analgesic and anti-pyretic uses of compositions comprising a compound of Formula (I):

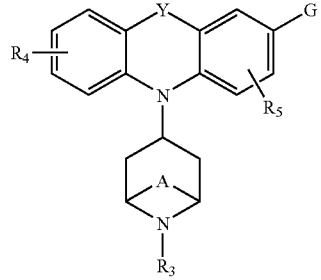

Formula (I)

wherein:

G is —C(Z)N($R_1$)$R_2$, $C_{6-10}$aryl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, furyl, indazolyl, indolyl, indolinyl, isothiazolyl, isoxazolyl, oxazolyl, isoxadiazolyl, benzoxazolyl, quinolinyl, isoquinolinyl, and pyridinyl; wherein aryl and the heterocycles of G are optionally substituted with one to three substituents independently selected from the group consisting of $C_{1-8}$alkanyl, $C_{2-8}$alkenyl, $C_{2-8}$alkynyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, nitro, oxo, thioxo, amino, $C_{1-6}$alkanylamino, di($C_{1-6}$alkanyl)amino, $C_{1-8}$alkanylthio, $C_{1-8}$alkanylsulfonyl, $C_{1-8}$alkanylsulfonylamino, aminocarbonyl, aminothiocarbonyl, aminocarbonylamino, aminothiocarbonylamino, $C_{1-8}$alkanylaminocarbonyl, di($C_{1-8}$alkanyl)aminocarbonyl, and $C_{1-6}$alkanyloxycarbonylamino;

$R_1$ is a substituent selected from the group consisting of hydrogen, $C_{1-8}$alkanyl, $C_{2-8}$alkenyl, and $C_{2-8}$alkynyl;

$R_2$ is a substituent selected from the group consisting of hydrogen; $C_{1-8}$alkanyl; $C_{2-8}$alkenyl; $C_{2-8}$alkynyl; $C_{6-10}$aryl; and $C_{1-8}$cycloalkanyl; wherein $C_{1-8}$alkanyl is optionally substituted with one to three substituents independently selected from the group consisting of phenyl, amino, $C_{1-6}$alkanylamino, di($C_{1-6}$alkanyl)amino, $C_{1-6}$alkanyloxy, thio$C_{1-6}$alkanyloxy, hydroxy, fluoro, chloro, cyano, aminocarbonyl, $C_{1-8}$alkanylaminocarbonyl, di($C_{1-8}$alkanyl)aminocarbonyl, $C_{1-6}$alkanyloxycarbonyl, and aryloxy; and wherein any aryl-containing substituents and $C_{1-8}$cycloalkanyl substituents of $R_2$ are optionally substituted with one to three substituents independently selected from the group consisting of $C_{1-8}$alkanyl, $C_{2-8}$alkenyl, $C_{2-8}$alkynyl, $C_{1-8}$alkanyloxy, trifluoromethyl, trifluoromethoxy, phenyl, halogen, cyano, hydroxy, $C_{1-8}$alkanylthio, $C_{1-8}$alkanylsulfonyl, and $C_{1-8}$alkanylsulfonylamino;

or $R_1$ and $R_2$ taken together with the nitrogen to which they are attached form a 5-7 membered cycloheteroalkyl optionally substituted with one to three substituents independently selected from the group consisting of $C_{1-8}$alkanyl, hydroxy($C_{1-8}$)alkanyl, hydroxy, amino, $C_{1-6}$alkanylamino, di($C_{1-6}$alkanyl)amino, and halogen;

$R_3$ is a substituent selected from the group consisting of hydrogen, $C_{1-8}$alkanyl, halo$_{1-3}$($C_{1-8}$)alkanyl, $C_{2-8}$alkenyl, $C_{2-8}$alkynyl, $C_{3-8}$cycloalkanyl, cycloalkanyl($C_{1-8}$)alkanyl, $C_{1-8}$alkanyloxy($C_{1-8}$)alkanyl, $C_{1-8}$alkanylthio($C_{1-8}$)alkanyl, hydroxy$C_{1-8}$alkanyl, $C_{1-8}$alkanyloxycarbonyl, halo$_{1-3}$($C_{1-8}$)alkanylcarbonyl, formyl, thioformyl, carbamimidoyl, phenylimino($C_{1-8}$)alkanyl, phenyl($C_{1-8}$)alkanyl, phenyl($C_{1-8}$)alkenyl, phenyl($C_{1-8}$)alkynyl, naphthyl($C_{1-8}$)alkanyl and heteroaryl($C_{1-8}$)alkanyl wherein the heteroaryl is selected from the group consisting of benzo[1,3]dioxolyl, imidazolyl, furanyl, pyridinyl, thienyl, indazolyl, indolyl, indolinyl, isoindolinyl, isoquinolinyl, isothiazolyl, isoxazolyl, oxazolyl, pyrazinyl, pyrazolyl, pyridazinyl, pyrimidinyl, pyrrolyl, quinolinyl, isoquinolinyl, tetrazolyl, thiazolyl; wherein phenyl, naphthyl and heteroaryl are optionally substituted with one to three substituents independently selected from the group consisting of $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl, thioureido, and fluoro($C_{1-6}$)alkanyloxy; alternatively, when phenyl and heteroaryl are optionally substituted with alkanyl or alkanyloxy substituents attached to adjacent carbon atoms, the two substituents can together form a fused cyclic alkanyl or cycloheteroalkanyl selected from the group consisting of —(CH$_2$)$_{3-5}$—, —O(CH$_2$)$_{2-4}$—, —(CH$_2$)$_{2-4}$O—, and —O(CH$_2$)$_{1-3}$O—;

$R_4$ is one to three substituents independently selected from the group consisting of hydrogen; $C_{1-6}$alkanyl; $C_{2-6}$alkenyl; $C_{2-6}$alkynyl; aryl($C_{2-6}$)alkynyl; $C_{1-6}$alkanyloxy; amino; $C_{1-6}$alkanylamino; di($C_{1-6}$alkanyl)amino; $C_{6-10}$arylamino wherein aryl is optionally substituted with one to three substituents independently selected from the group consisting of $C_{1-6}$alkanyl, $C_{1-6}$alkoxy, halogen, and hydroxy; formylamino; pyridinylamino; $C_{1-6}$alkanylcarbonyl; $C_{1-6}$alkanylcarbonyloxy; $C_{1-6}$alkanyloxycarbonyl; aminocarbonyl; $C_{1-6}$alkanylaminocarbonyl; di($C_{1-6}$alkanyl)aminocarbonyl; $C_{1-6}$alkanylcarbonylamino; $C_{1-6}$alkanylthio; $C_{1-6}$alkanylsulfonyl; halogen; hydroxy; cyano; hydroxycarbonyl; $C_{6-10}$aryl; chromanyl; chromenyl; furanyl; imidazolyl; indazolyl; indolyl; indolinyl; isoindolinyl; isoquinolinyl; isothiazolyl; isoxazolyl; naphthyridinyl; oxazolyl; pyrazinyl; pyrazolyl; pyridazinyl; pyridinyl; pyrimidinyl; pyrrolyl; quinazolinyl; quinolinyl; quinolizinyl; quinoxalinyl; tetrazolyl; thiazolyl; thienyl; fluoroalkanyl; and fluoroalkanyloxy; or optionally, when $R_4$ is two substituents attached to adjacent carbon atoms, the two substituents together form a single fused moiety, wherein the fused moiety is —(CH$_2$)$_{3-5}$—, —O(CH$_2$)$_{2-4}$—, —(CH$_2$)$_{2-4}$O—, —O(CH$_2$)$_{1-3}$O—, or —S—C(NH$_2$)=N—;

$R_5$ is one to two substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl and fluoro($C_{1-6}$)alkanyloxy;

A is —(CH$_2$)$_m$—, wherein m is 2 or 3;

Y is O or S;

Z is O, S, NH, N($C_{1-6}$alkanyl), N(OH), N(O$C_{1-6}$alkanyl), or N(phenyl); and enantiomers, diastereomers, tautomers, solvates, or pharmaceutically acceptable salts thereof.

In certain of these embodiments, when G is pyridin-3-yl, furan-3-yl, thien-3-yl, or quinolin-3-yl and $R^3$ is hydrogen, $R^4$ is not hydrogen; and provided that when G is N,N-diethylaminocarbonyl and $R^3$ is methyl, $R^4$ is not hydrogen; and provided that when G is N,N-diethylaminocarbonyl and $R^3$ is hydrogen, $R^4$ is not α'-chloro.

Embodiments of the present invention include compounds of Formula (I) wherein, preferably:

a) G is —C(Z)N($R_1$)$R_2$, phenyl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, isothiazolyl, isoxazolyl, oxazolyl, isoxadiazolyl, and pyridinyl; wherein phenyl and the heterocycles of G are optionally substituted with one to three substituents independently selected from the group consisting of $C_{1-8}$alkanyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, di($C_{1-8}$alkanyl)aminocarbonyl, and $C_{1-6}$alkanyloxycarbonylamino; provided that when G is pyridin-3-yl or thien-3-yl and $R^3$ is hydrogen, $R^4$ is not hydrogen; and provided that when G is N,N-diethylaminocarbonyl and $R^3$ is methyl, $R^4$ is not hydrogen; and provided that when G is N,N-diethylaminocarbonyl and $R^3$ is hydrogen, $R^4$ is not α'-chloro;

b) G is —C(Z)N($R_1$)$R_2$, phenyl, or a heterocycle selected from the group consisting of imidazolyl, tetrazolyl, oxadiazolyl, thiadiazolyl, oxathiadiazolyl, imidazolinyl, thienyl, pyrazolyl, pyrimidinyl, triazinyl, isothiazolyl, isoxazolyl, oxazolyl, isoxadiazolyl, and pyridinyl; wherein phenyl and the heterocycles of G (described herein) are optionally substituted with one to three substituents independently selected from the group consisting of $C_{1-4}$alkanyl, $C_{1-4}$alkanyloxy, hydroxy($C_{1-4}$)alkanyl, carboxy($C_{1-4}$)alkanyl, $C_{1-4}$alkanylcarbonylamino, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, and di($C_{1-8}$alkanyl)aminocarbonyl; provided that when G is pyridin-3-yl or thien-3-yl and $R^3$ is hydrogen, $R^4$ is not hydrogen; and provided that when G is N,N-diethylaminocarbonyl and $R^3$ is methyl, $R^4$ is not hydrogen; and provided that when G is N,N-diethylaminocarbonyl and $R^3$ is hydrogen, $R^4$ is not α'-chloro;

c) G is —C(Z)N($R_1$)$R_2$, phenyl, or a heterocycle selected from the group consisting of imidazolyl, tetrazolyl, oxadiazolyl, thiadiazolyl, oxathiadiazolyl, thienyl, isothiazolyl, isoxazolyl, isoxadiazolyl, and pyridinyl; wherein phenyl and the heterocycles of G (described herein) are optionally substituted with one to three substituents independently selected from the group consisting of $C_{1-4}$alkanyl, $C_{1-4}$alkanyloxy, hydroxy($C_{1-4}$)alkanyl, $C_{1-4}$alkanylcarbonylamino, hydroxy, cyano, oxo, thioxo, and aminocarbonyl; provided that when G is pyridin-3-yl or thien-3-yl and $R^3$ is hydrogen, $R^4$ is not hydrogen; and provided that when G is N,N-diethylaminocarbonyl and $R^3$ is methyl, $R_4$ is not hydrogen; and provided that when G is N,N-diethylaminocarbonyl and $R^3$ is hydrogen, $R^4$ is not α'-chloro;

d) $R_1$ is a substituent selected from the group consisting of hydrogen and $C_{1-4}$alkanyl;

e) $R_1$ is selected from the group consisting of hydrogen, methyl, ethyl, and propyl;

f) $R_1$ is selected from the group consisting of hydrogen, methyl, or ethyl;

g) $R_2$ is selected from the group consisting of hydrogen; $C_{1-4}$alkanyl; phenyl; and $C_{1-6}$cycloalkanyl; wherein $C_{1-4}$alkanyl is optionally substituted with one to three substituents independently selected from the group consisting of phenyl, amino, $C_{1-6}$alkanylamino, di($C_{1-6}$alkanyl)amino, $C_{1-4}$alkanyloxy, hydroxy, fluoro, chloro, cyano, aminocarbonyl, $C_{1-8}$alkanylaminocarbonyl, di($C_{1-8}$alkanyl)aminocarbonyl, and phenoxy; and wherein any phenyl-containing substituents and $C_{1-6}$cycloalkanyl substituents of $R_2$ are optionally substituted with one to three substituents independently selected from the group consisting of $C_{1-8}$alkanyl, $C_{1-8}$alkanyloxy, trifluoromethyl, phenyl, fluoro, hydroxy, $C_{1-8}$alkanylthio, $C_{1-8}$alkanylsulfonyl, and $C_{1-8}$alkanylsulfonylamino; or $R_1$ and $R_2$ taken together with the nitrogen to which they are attached form a 5-7 membered cycloheteroalkyl optionally substituted with one to three substituents independently selected from the group consisting of $C_{1-4}$alkanyl, hydroxy($C_{1-4}$)alkanyl, hydroxy, amino, $C_{1-6}$alkanylamino, di($C_{1-6}$alkanyl)amino, and fluoro;

h) $R_2$ is selected from the group consisting of hydrogen, $C_{1-4}$alkanyl, phenyl, and $C_{1-6}$cycloalkanyl; wherein $C_{1-4}$alkanyl is optionally substituted with one to three substituents independently selected from the group consisting of phenyl, $C_{1-4}$alkanyloxy, hydroxy, fluoro, aminocarbonyl, $C_{1-8}$alkanylaminocarbonyl, di($C_{1-8}$alkanyl)aminocarbonyl, and phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, hydroxy, and $C_{1-6}$alkanylthio; or $R_1$ and $R_2$ taken together with the nitrogen to which they are attached form a 5-7 membered cycloheteroalkyl optionally substituted with one to three substituents independently selected from the group consisting of $C_{1-4}$alkanyl and hydroxy;

i) $R_2$ is selected from the group consisting of hydrogen, $C_{1-4}$alkanyl and phenyl, wherein $C_{1-4}$alkanyl is optionally substituted with one to three substituents independently selected from the group consisting of phenyl, $C_{1-4}$alkanyloxy, hydroxy, fluoro, and phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, and hydroxy; or $R_1$ and $R_2$ taken together with the nitrogen to which they are attached form a pyrrolidinyl or piperidinyl ring wherein said pyrrolidinyl or piperidinyl is optionally substituted with a substituent selected from the group consisting of $C_{1-3}$alkanyl and hydroxy;

j) $R_3$ is selected from the group consisting of hydrogen, $C_{1-8}$alkanyl, $C_{2-8}$alkenyl, $C_{2-8}$alkynyl, $C_{1-8}$alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-8}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, isoquinolinyl, tetrazolyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O($CH_2$)$_{1-3}$O—;

k) $R_3$ is selected from the group consisting of hydrogen, methyl, allyl, 2-methyl-allyl, propynyl, hydroxyethyl, methylthioethyl, methoxyethyl, thioformyl, phenyliminomethyl, phenethyl, and heteroaryl($C_{1-8}$)alkanyl wherein the heteroaryl is selected from the group consisting of benzo[1,3]dioxolyl, imidazolyl, furanyl, pyridinyl, thienyl, pyrimidinyl, pyrrolyl, quinolinyl, isoquinolinyl, tetrazolyl; wherein the phenyl in any phenyl-containing substituent is optionally substituted with one hydroxyl group;

l) $R_3$ is hydrogen, methyl, allyl, or heteroarylmethyl wherein heteroaryl is selected from the group consisting of benzo[1,3]dioxolyl, imidazolyl, furanyl, pyridinyl, and thienyl;

m) $R_4$ is one to three substituents independently selected from the group consisting of hydrogen, $C_{1-6}$alkanyl, $C_{1-6}$alkanyloxy, $C_{6-10}$arylamino wherein aryl is optionally substituted with one to three substituents independently selected from the group consisting of $C_{1-6}$alkanyl, $C_{1-6}$alkoxy, halogen, and hydroxy, formylamino, pyridinylamino, aminocarbonyl, $C_{1-6}$alkanylaminocarbonyl, $C_{1-6}$alkanylcarbonylamino, halogen, hydroxy, C$_{6-10}$aryl, chromanyl, chromenyl, furanyl, imidazolyl, indazolyl, indolyl, indolinyl, isoindolinyl, isoquinolinyl, isothiazolyl, isoxazolyl, naphthyridinyl, oxazolyl, pyrazinyl, pyrazolyl, pyridazinyl, pyridinyl, pyrimidinyl, pyrrolyl, quinazolinyl, quinolinyl, quinolizinyl, quinoxalinyl, tetrazolyl, thiazolyl, and thienyl;

n) R$_4$ is one to two substituents independently selected from the group consisting of hydrogen, C$_{1-4}$alkanyl, C$_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, and hydroxy;

o) R$_4$ is one to two substituents independently selected from the group consisting of hydrogen, methyl, methoxy, bromo, fluoro, hydroxy, α'- or β'-phenyl, α'- or β'-pyridinyl, and α'- or β'-furanyl;

p) R$_5$ is one to two substituents independently selected from the group consisting of hydrogen and halogen;

q) R$_5$ is hydrogen;

r) A is —(CH$_2$)$_{2-3}$—;

s) A is —(CH$_2$)$_2$—;

t) Y is O or S;

u) Z is O, NH, N(C$_{1-6}$alkanyl), N(OH), N(OC$_{1-6}$alkanyl), or N(phenyl);

v) Z is O, NH, or N(OH);

w) Z is O or NH;

aa) G is —C(Z)N(R$_1$)R$_2$, phenyl, or a heterocycle selected from the group consisting of tetrazolyl, oxadiazolyl, furyl, quinolinyl, thienyl, and pyridinyl; wherein phenyl and the heterocycles of G are optionally substituted with one to three substituents independently selected from the group consisting of C$_{1-8}$alkanyl, C$_{1-8}$alkanyloxy, hydroxy(C$_{1-8}$)alkanyl, carboxy(C$_{1-8}$)alkanyl, C$_{1-8}$alkanylcarbonylamino, halogen, hydroxy, cyano, oxo, thioxo, amino, C$_{1-6}$alkanylamino, di(C$_{1-6}$alkanyl)amino, C$_{1-8}$alkanylthio, aminocarbonyl, aminothiocarbonyl, C$_{1-8}$alkanylaminocarbonyl, di(C$_{1-8}$alkanyl)aminocarbonyl, and C$_{1-6}$alkanyloxycarbonylamino;

bb) G is —C(Z)N(R$_1$)R$_2$, phenyl, or a heterocycle selected from the group consisting of tetrazolyl, oxadiazolyl, furyl, quinolinyl, thienyl, and pyridinyl; wherein phenyl and the heterocycles of G are optionally substituted with one to three substituents independently selected from the group consisting of C$_{1-4}$alkanyl, C$_{1-4}$alkanyloxy, hydroxy(C$_{1-4}$)alkanyl, C$_{1-4}$alkanylcarbonylamino, hydroxy, cyano, oxo, thioxo, and aminocarbonyl;

cc) G is —C(Z)N(R$_1$)R$_2$, tetrazolyl, furyl, quinolinyl, thienyl, pyridinyl, oxadiazolyl optionally substituted with oxo, or phenyl optionally substituted with (C$_{1-8}$)alkanylcarbonylamino;

dd) G is —C(Z)N(R$_1$)R$_2$, 1H-tetrazol-4-yl, 3-furyl, quinolin-3-yl, thiophen-3-yl, 4H-[1,2,4]-oxadiazol-5-oxo-3-yl, 2-methylcarbonylaminophenyl, pyridin-3-yl or pyridin-4-yl;

ee) R$_2$ is selected from the group consisting of hydrogen and C$_{1-4}$alkanyl; wherein C$_{1-4}$alkanyl is optionally substituted with phenyl; or R$_1$ and R$_2$ taken together with the nitrogen to which they are attached form a pyrrolidinyl ring wherein said pyrrolidinyl ring is optionally substituted with hydroxy;

ff) R$_2$ is selected from the group consisting of hydrogen, methyl, ethyl, and phenethyl; or R$_1$ and R$_2$ taken together with the nitrogen to which they are attached form pyrrolidin-1-yl, 3-hydoxypyrrolidin-1-yl or 3-(S)-hydoxypyrrolidin-1-yl;

gg) R$_2$ is ethyl or R$_1$ and R$_2$ taken together with the nitrogen to which they are attached form 3-hydoxypyrrolidin-1-yl or 3-(S)-hydoxypyrrolidin-1-yl;

hh) R$_3$ is selected from the group consisting of hydrogen, C$_{1-8}$alkanyl, C$_{2-8}$alkenyl, C$_{2-8}$alkynyl, C$_{1-8}$alkanyloxy(C$_{1-8}$)alkanyl, C$_{1-8}$alkanylthio(C$_{1-8}$)alkanyl, hydroxyC$_{1-8}$alkanyl, thioformyl, phenylimino(C$_{1-8}$)alkanyl, phenyl(C$_{1-8}$)alkanyl, and heteroaryl(C$_{1-8}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, thiazolyl, isoquinolinyl, and tetrazolyl; wherein phenyl and heteroaryl are optionally substituted with one to three substituents independently selected from the group consisting of C$_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O(CH$_2$)$_{1-3}$O—;

ii) R$_3$ is selected from the group consisting of hydrogen, methyl, methylbutenyl, propenyl, benzyl, phenethyl, allyl, and heteroaryl(C$_{1-8}$)alkanyl wherein the heteroaryl is selected from the group consisting of imidazolyl, furanyl, pyridinyl, thienyl, and thiazolyl;

jj) R$_3$ is selected from the group consisting of hydrogen, benzyl, allyl, methyl, phenethyl, and heteroaryl(C$_{1-8}$)alkanyl wherein the heteroaryl is selected from the group consisting of imidazolyl, furanyl, pyridinyl, and thienyl;

kk) R$_3$ is selected from the group consisting of hydrogen, methyl, benzyl, 2-phenethyl, pyridin-2-ylmethyl, fur-3-ylmethyl, thiophene-2-ylmethyl, and 1H-imidazol-2-ylmethyl;

ll) R$_4$ is one to two substituents independently selected from the group consisting of hydrogen, methoxy, methyl, phenyl, bromo, fluoro, aminocarbonyl, chloro and hydroxy;

mm) R$_4$ is one to two substituents independently selected from the group consisting of hydrogen, methoxy, and hydroxy wherein the methoxy and hydroxy groups are at the α' position;

nn) R$_4$ is one substituent and is hydrogen or hydroxy at the α' position;

oo) R$_4$ is one substituent and is hydrogen;

pp) R$_4$ is one substituent and is hydroxy at the α' position;

qq) Y is oxygen and combinations of a) through qq) above.

One embodiment of the present invention is a compound of Formula (I) wherein:

G is —C(Z)N(R$_1$)R$_2$, phenyl, or a heterocycle selected from the group consisting of imidazolyl, triazolyl, tetrazolyl, oxadiazolyl, thiadiazolyl, oxathiadiazolyl, imidazolinyl, tetrahydropyrimidinyl, thienyl, pyrazolyl, pyrimidinyl, triazinyl, isothiazolyl, isoxazolyl, oxazolyl, isoxadiazolyl, and pyridinyl; wherein phenyl and the heterocycles of G are optionally substituted with one to three substituents independently selected from the group consisting of C$_{1-8}$alkanyl, C$_{1-8}$alkanyloxy, hydroxy(C$_{1-8}$)alkanyl, carboxy(C$_{1-8}$)alkanyl, C$_{1-8}$alkanylcarbonylamino, halogen, hydroxy, cyano, oxo, thioxo, amino, C$_{1-6}$alkanylamino, di(C$_{1-6}$alkanyl)amino, C$_{1-8}$alkanylthio, aminocarbonyl, aminothiocarbonyl, C$_{1-8}$alkanylaminocarbonyl, di(C$_{1-8}$alkanyl)aminocarbonyl, and C$_{1-6}$alkanyloxycarbonylamino;

provided that when G is pyridin-3-yl or thien-3-yl and $R^3$ is hydrogen, $R^4$ is not hydrogen; and provided that when G is N,N-diethylaminocarbonyl and $R^3$ is methyl, $R^4$ is not hydrogen; and provided that when G is N,N-diethylaminocarbonyl and $R^3$ is hydrogen, $R^4$ is not α'-chloro;

$R_1$ is hydrogen or $C_{1-4}$alkanyl;

$R_2$ is selected from the group consisting of hydrogen; $C_{1-4}$alkanyl; phenyl; and $C_{1-6}$cycloalkanyl; wherein $C_{1-4}$alkanyl is optionally substituted with one to three substituents independently selected from the group consisting of phenyl, amino, $C_{1-6}$alkanylamino, di($C_{1-6}$alkanyl)amino, $C_{1-4}$alkanyloxy, hydroxy, fluoro, chloro, cyano, aminocarbonyl, $C_{1-8}$alkanylaminocarbonyl, di($C_{1-8}$alkanyl)aminocarbonyl, and phenoxy; and wherein the phenyl and $C_{1-6}$cycloalkanyl substituents of $R_2$ are optionally substituted with one to three substituents independently selected from the group consisting of $C_{1-8}$alkanyl, $C_{1-8}$alkanyloxy, trifluoromethyl, phenyl, fluoro, hydroxy, $C_{1-8}$alkanylthio, $C_{1-8}$alkanylsulfonyl, and $C_{1-8}$alkanylsulfonylamino; or $R_1$ and $R_2$ taken together with the nitrogen to which they are attached form a 5-7 membered cycloheteroalkyl optionally substituted with one to three substituents independently selected from the group consisting of $C_{1-4}$alkanyl, hydroxy($C_{1-4}$)alkanyl, hydroxy, amino, $C_{1-6}$alkanylamino, di($C_{1-6}$alkanyl)amino, and fluoro;

$R_3$ is selected from the group consisting of hydrogen, $C_{1-8}$alkanyl, $C_{2-8}$alkenyl, $C_{2-8}$alkynyl, $C_{1-8}$alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-8}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, isoquinolinyl, tetrazolyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O(CH$_2$)$_{1-3}$O—;

$R_4$ is one to three substituents independently selected from the group consisting of hydrogen, $C_{1-6}$alkanyl, $C_{1-6}$alkanyloxy, $C_{6-10}$arylamino wherein aryl is optionally substituted with one to three substitutents independently selected from the group consisting of $C_{1-6}$alkanyl, $C_{1-6}$alkoxy, halogen, and hydroxy, formylamino, pyridinylamino, aminocarbonyl, $C_{1-6}$alkanylaminocarbonyl, $C_{1-6}$alkanylcarbonylamino, halogen, hydroxy, $C_{6-10}$aryl, chromanyl, chromenyl, furanyl, imidazolyl, indazolyl, indolyl, indolinyl, isoindolinyl, isoquinolinyl, isothiazolyl, isoxazolyl, naphthyridinyl, oxazolyl, pyrazinyl, pyrazolyl, pyridazinyl, pyridinyl, pyrimidinyl, pyrrolyl, quinazolinyl, quinolinyl, quinolizinyl, quinoxalinyl, tetrazolyl, thiazolyl, and thienyl;

$R_5$ is one to two substituents independently selected from the group consisting of hydrogen and halogen;

A is CH$_2$CH$_2$;

Y is O or S;

Z is O, NH, N($C_{1-6}$alkanyl), N(OH), N(OC$_{1-6}$alkanyl), or N(phenyl); and enantiomers, diastereomers, tautomers, solvates, and pharmaceutically acceptable salts thereof.

Another embodiment of the present invention is a compound of Formula (I) wherein:

G is —C(Z)N(R$_1$)R$_2$, phenyl, or a heterocycle selected from the group consisting of imidazolyl, tetrazolyl, oxadiazolyl, thiadiazolyl, oxathiadiazolyl, imidazolinyl, thienyl, pyrazolyl, pyrimidinyl, triazinyl, isothiazolyl, isoxazolyl, oxazolyl, isoxadiazolyl, and pyridinyl; wherein phenyl and the heterocycles of G (described herein) are optionally substituted with one to three substituents independently selected from the group consisting of $C_{1-4}$alkanyl, $C_{1-4}$alkanyloxy, hydroxy($C_{1-4}$)alkanyl, carboxy($C_{1-4}$)alkanyl, $C_{1-4}$alkanylcarbonylamino, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, and di($C_{1-8}$alkanyl)aminocarbonyl; provided that when G is pyridin-3-yl or thien-3-yl and $R^3$ is hydrogen, $R^4$ is not hydrogen; and provided that when G is N,N-diethylaminocarbonyl and $R^3$ is methyl, $R^4$ is not hydrogen; and provided that when G is N,N-diethylaminocarbonyl and $R^3$ is hydrogen, $R^4$ is not α'-chloro;

$R_1$ is selected from the group consisting of hydrogen, methyl, ethyl, and propyl;

$R_2$ is selected from the group consisting of hydrogen, $C_{1-4}$alkanyl, phenyl, and $C_{1-6}$cycloalkanyl; wherein $C_{1-4}$alkanyl is optionally substituted with one to three substituents independently selected from the group consisting of phenyl, $C_{1-4}$alkanyloxy, hydroxy, fluoro, aminocarbonyl, $C_{1-8}$alkanylaminocarbonyl, di($C_{1-8}$alkanyl)aminocarbonyl, and phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, hydroxy, and $C_{1-6}$alkanylthio; or $R_1$ and $R_2$ taken together with the nitrogen to which they are attached form a pyrrolidinyl or piperidinyl ring wherein said pyrrolidinyl or piperidinyl is optionally substituted with a substituent selected from the group consisting of $C_{1-3}$alkanyl and hydroxy;

$R_3$ is selected from the group consisting of hydrogen, methyl, allyl, 2-methyl-allyl, propynyl, hydroxyethyl, methylthioethyl, methoxyethyl, thioformyl, phenyliminomethyl, phenethyl, and heteroaryl($C_{1-8}$)alkanyl wherein the heteroaryl is selected from the group consisting of benzo[1,3]dioxolyl, imidazolyl, furanyl, pyridinyl, thienyl, pyrimidinyl, pyrrolyl, quinolinyl, isoquinolinyl, tetrazolyl wherein the phenyl in any phenyl-containing substituent is optionally substituted with one hydroxyl group;

$R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, and hydroxy;

$R_5$ is hydrogen;

A is CH$_2$CH$_2$;

Y is O or S;

Z is O, NH, or N(OH); and enantiomers, diastereomers, tautomers, solvates, and pharmaceutically acceptable salts thereof.

Another embodiment of the present invention is directed to compositions comprising a compound of Formula (I) wherein:

G is selected from —C(Z)N(R$_1$)R$_2$, phenyl, or a heterocycle selected from the group consisting of imidazolyl, tetrazolyl, oxadiazolyl, thiadiazolyl, oxathiadiazolyl, thienyl, isothiazolyl, isoxazolyl, isoxadiazolyl, and pyridinyl; wherein phenyl and the heterocycles of G are optionally substituted with one to three substituents independently selected from the group consisting of $C_{1-4}$alkanyl, $C_{1-4}$alkanyloxy, hydroxy($C_{1-4}$)alkanyl, $C_{1-4}$alkanylcarbonylamino, hydroxy, cyano, oxo, thioxo, and aminocarbonyl; provided that when G is pyridin-3-yl or thien-3-yl and $R^3$ is hydrogen, $R^4$ is not hydrogen; and provided that when G is N,N-diethylaminocarbonyl and $R^3$ is methyl, $R^4$ is not hydrogen; and provided that when G is N,N-diethylaminocarbonyl and $R^3$ is hydrogen, $R^4$ is not α'-chloro;

$R_1$ is hydrogen, methyl, or ethyl;

$R_2$ is independently selected from the group consisting of hydrogen, $C_{1-4}$alkanyl and phenyl; wherein $C_{1-4}$alkanyl is optionally substituted with one to three substituents independently selected from the group consisting of phenyl, $C_{1-4}$alkanyloxy, hydroxy, fluoro, and phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, and hydroxy; or $R_1$ and $R_2$ taken together with the nitrogen to which they are attached form a pyrrolidinyl or piperidinyl ring wherein said pyrrolidinyl or piperidinyl are optionally substituted with a substituent selected from the group consisting of $C_{1-3}$alkanyl and hydroxy;

$R_3$ is hydrogen, methyl, allyl, or heteroarylmethyl wherein heteroaryl is selected from the group consisting of benzo[1,3]dioxolyl, imidazolyl, furanyl, pyridinyl, and thienyl;

$R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, and hydroxy;

A is $CH_2CH_2$;

Y is O or S;

Z is O or NH; and enantiomers, diasteromers, tautomers, solvates, and pharmaceutically acceptable salts thereof.

Another embodiment of the present invention is a compound of Formula (I) wherein:

G is selected from —C(Z)N($R_1$)$R_2$, 2-methylcarbonylaminophenyl, 2-aminocarbonyl-phenyl, 1H-tetrazol-4-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, or pyridin-3-yl; provided that when G is pyridin-3-yl and $R^3$ is hydrogen, $R^4$ is not hydrogen; and provided that when G is N,N-diethylaminocarbonyl and $R^3$ is methyl, $R^4$ is not hydrogen; and provided that when G is N,N-diethylaminocarbonyl and $R^3$ is hydrogen, $R^4$ is not α'-chloro;

$R_1$ is hydrogen, methyl, or ethyl;

$R_2$ is selected from the group consisting of hydrogen, $C_{1-4}$alkanyl and phenyl; wherein $C_{1-4}$alkanyl is optionally substituted with one to three substituents independently selected from the group consisting of phenyl, $C_{1-4}$alkanyloxy, hydroxy, fluoro, and phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, and hydroxy;

or $R_1$ and $R_2$ taken together with the nitrogen to which they are attached form a pyrrolidinyl or piperidinyl ring;

$R_3$ is selected from the group consisting of hydrogen, $C_{1-8}$alkanyl, $C_{2-8}$alkenyl, $C_{2-8}$alkynyl, $C_{1-8}$alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-8}$)alkanyl wherein heteroaryl is selected from the group consisting of hydrogen, methyl, allyl, or heteroarylmethyl; wherein heteroaryl is selected from the group consisting of benzo[1,3]dioxolyl, imidazolyl, furanyl, pyridinyl, and thienyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O($CH_2$)$_{1-3}$O—;

$R_4$ is one to three substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, and hydroxy;

$R_5$ is hydrogen;

A is $CH_2CH_2$;

Y is O or S;

Z is O or NH; and enantiomers, diastereomers, tautomers, solvates, and pharmaceutically acceptable salts thereof.

Another embodiment of the present invention is directed to compositions comprising a compound of Formula (I) wherein G is independently selected from —C(Z)N($R_1$)$R_2$, 2-methylcarbonylaminophenyl, 2-aminocarbonyl-phenyl, 1H-tetrazol-4-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, and pyridin-3-yl; provided that when G is pyridin-3-yl and $R^3$ is hydrogen, $R^4$ is not hydrogen; and provided that when G is N,N-diethylaminocarbonyl and $R^3$ is methyl, $R^4$ is not hydrogen; and provided that when G is N,N-diethylaminocarbonyl and $R^3$ is hydrogen, $R^4$ is not α'-chloro; $R_1$ is hydrogen, methyl, or ethyl; $R_2$ is a substituent selected from the group consisting of hydrogen, $C_{1-4}$alkanyl and phenyl; wherein $C_{1-4}$alkanyl is optionally substituted with one to three substituents independently selected from the group consisting of phenyl, $C_{1-4}$alkanyloxy, hydroxy, and 2,6-dimethyl-phenoxy; and wherein the any phenyl-containing substituent of $R_2$ is optionally substituted with one to three substituents independently selected from the group consisting of $C_{1-6}$alkanyl, $C_{1-6}$alkanyloxy, fluoro, and hydroxy; or $R_1$ and $R_2$ taken together with the nitrogen to which they are attached form a pyrrolidinyl or piperidinyl ring wherein said pyrrolidinyl or piperidinyl is optionally substituted with a substituent selected from the group consisting of $C_{1-3}$alkanyl and hydroxy; $R_3$ is a substituent selected from the group consisting of benzo[1,3]dioxol-5-ylmethyl, carbamimidoyl, 1-H-imidazol-4-ylmethyl, phenyliminomethyl, 1-prop-2-ynyl, thioformyl, 2-hydroxyphenyl-methyl, hydroxy-ethyl, methoxy-ethyl, 2-methyl-allyl, 2-methyl-but-2-enyl, allyl, furan-3-ylmethyl, H, Me, methylthioethyl, phenethyl, pyridin-2-yl methyl, and thiophen-2-ylmethyl; $R_4$ is one to two substituents independently selected from the group consisting of hydrogen, $C_{1-4}$alkanyl, $C_{1-4}$alkanyloxy, halogen, phenyl, furanyl, imidazolyl, indazolyl, indolyl, indolinyl, isoindolinyl, isoquinolinyl, isothiazolyl, isoxazolyl, oxazolyl, pyrazinyl, pyrazolyl, pyridazinyl, pyridinyl, pyrimidinyl, pyrrolyl, quinolinyl, tetrazolyl, thiazolyl, thienyl, and hydroxy; A is $CH_2CH_2$; Y is O or S; and Z is O or NH.

Another embodiment of the present invention is directed to compositions comprising a compound of Formula (I) wherein G is selected from —$C(Z)N(R_1)R_2$, 2-methylcarbonylaminophenyl, 2-aminocarbonyl-phenyl, 1H-tetrazol-4-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, or pyridin-3-yl; provided that when G is pyridin-3-yl and $R^3$ is hydrogen, $R^4$ is not hydrogen; and provided that when G is N,N-diethylaminocarbonyl and $R^3$ is methyl, $R^4$ is not hydrogen; $R_1$ is hydrogen, methyl, or ethyl; $R_2$ is a substituent selected from the group consisting of hydrogen, $C_{1-4}$alkanyl and phenyl; wherein $C_{1-4}$alkanyl is optionally substituted with one to three substituents independently selected from the group consisting of phenyl, methoxy, hydroxy, and 2,6-dimethyl-phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, and hydroxy; or $R_1$ and $R_2$ taken together with the nitrogen to which they are attached form a pyrrolidinyl or piperidinyl ring wherein said pyrrolidinyl or piperidinyl are optionally substituted with a substituent selected from the group consisting of $C_{1-3}$alkanyl and hydroxy; $R_3$ is a substituent selected from the group consisting of benzo[1,3]dioxol-5-ylmethyl, carbamimidoyl, 1-H-imidazol-4-yl methyl, phenyliminomethyl, 1-prop-2-ynyl, thioformyl, 2-hydroxyphenyl-methyl, hydroxyethyl, methoxyethyl, allyl, furan-3-yl methyl, H, Me, methylthioethyl, and phenethyl; $R_4$ is one to two substituents independently selected from the group consisting of hydrogen, methyl, methoxy, bromo, fluoro, hydroxy, α'- or β'-phenyl, α'- or β'-pyridinyl, and α'- or β'-furanyl; A is $CH_2CH_2$; Y is O or S; and Z is O or NH.

Another embodiment of the present invention is directed to compositions comprising a compound of Formula (I) wherein G is selected from —$C(Z)N(R_1)R_2$, 2-methylcarbonylaminophenyl, 2-aminocarbonyl-phenyl, 1H-tetrazol-4-yl, 2-methyl-tetrazol-5-yl, 4H-[1,2,4]-oxadiazol-5-oxo-3-yl, 4H-[1,2,4]-oxadiazol-5-thioxo-3-yl, 4H-[1,2,4]thiadiazol-5-oxo-3-yl, [1,2,3,5]oxathiadiazol-2-oxo-4-yl, or pyridin-3-yl; provided that when G is pyridin-3-yl and $R^3$ is hydrogen, $R^4$ is not hydrogen; and provided that when G is N,N-diethylaminocarbonyl and $R^3$ is methyl, $R^4$ is not hydrogen; $R_1$ is hydrogen, methyl, or ethyl; $R_2$ is a substituent selected from the group consisting of hydrogen, $C_{1-4}$alkanyl and phenyl; wherein $C_{1-4}$alkanyl is optionally substituted with one to three substituents independently selected from the group consisting of phenyl, methoxy, hydroxy, and 2,6-dimethyl-phenoxy; and wherein any phenyl-containing substituent of $R_2$ is optionally substituted with one to three substituents independently selected from the group consisting of $C_{1-6}$alkanyl, $C_{1-6}$alkanyloxy, fluoro, and hydroxy; alternatively $R_1$ and $R_2$ are taken together with the nitrogen to which they are attached to form a pyrrolidinyl or piperidinyl ring wherein said pyrrolidinyl or piperidinyl are optionally substituted with a substituent selected from the group consisting of $C_{1-3}$alkanyl and hydroxy; $R_3$ is a substituent selected from the group consisting of H, benzo[1,3]dioxol-5-ylmethyl, 1-H-imidazol-4-yl methyl, furan-3-ylmethyl, pyridin-2-ylmethyl, and phenyliminomethyl; $R_4$ is a substituent independently selected from the group consisting of hydrogen, methyl, methoxy, bromo, fluoro, hydroxy, α'- or β'-phenyl, α'- or β'-pyridinyl, and α'- or β'-furanyl; A is $CH_2CH_2$; Y is O or S; and Z is O or NH.

Another embodiment of the present invention is directed to a compound of Formula (I) wherein $R_4$ is preferably substituted at the α'- or β'-position of Formula (I).

Another embodiment of the present invention is directed to compounds of Formula (I) wherein:

G is —$C(Z)N(R_1)R_2$, phenyl, or a heterocycle selected from the group consisting of tetrazolyl, oxadiazolyl, furyl, quinolinyl, thienyl, and pyridinyl; wherein phenyl and the heterocycles of G are optionally substituted with one to three substituents independently selected from the group consisting of $C_{1-8}$alkanyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, di($C_{1-8}$alkanyl)aminocarbonyl, and $C_{1-6}$alkanyloxycarbonylamino;

$R_1$ is $C_{1-4}$ alkanyl, or hydrogen;

$R_2$ is hydrogen or $C_{1-4}$ alkanyl optionally substituted with phenyl;

or $R_1$ and $R_2$ taken together with the nitrogen to which they are attached form a pyrrolidinyl ring optionally substituted with hydroxy;

Z is NH or oxygen;

$R_3$ is pyridinyl($C_{1-8}$)alkanyl, furyl($C_{1-8}$)alkanyl, $C_{1-8}$ alkanyl, hydrogen, $C_{2-8}$ alkenyl, thienyl($C_{1-8}$)alkanyl, imidazolyl($C_{1-8}$)alkanyl, phenyl($C_{1-8}$)alkalnyl, or thiazolyl($C_{1-8}$)alkanyl;

$R_4$ is one to three substituents selected from the group consisting of hydrogen, $C_{1-6}$ alkanyl, $C_{1-6}$ alkanyloxy, hydroxy, halogen, aminocarbonyl, and phenyl;

$R_5$ is hydrogen;

A is $CH_2CH_2$;

Y is O;

Z is O or NH; and enantiomers, diastereomers, tautomers, solvates, and pharmaceutically acceptable salts thereof.

Another embodiment of the present invention is directed to compounds of Formula (I) wherein:

G is —$C(Z)N(R_1)R_2$, tetrazolyl, furyl, quinolinyl, thienyl, pyridinyl, oxadiazolyl optionally substituted with oxo, or phenyl optionally substituted with ($C_{1-8}$)alkanylcarbonylamino;

$R_1$ is $C_{1-4}$ alkanyl, or hydrogen;

$R_2$ is hydrogen or $C_{1-4}$ alkanyl;

or $R_1$ and $R_2$ taken together with the nitrogen to which they are attached form a pyrrolidinyl ring optionally substituted with hydroxy;

Z is NH or oxygen;

$R_3$ is pyridinyl($C_{1-8}$)alkanyl, furyl($C_{1-8}$)alkanyl, $C_{1-8}$ alkanyl, hydrogen, $C_{2-8}$ alkenyl, thienyl($C_{1-8}$)alkanyl, imidazolyl($C_{1-8}$)alkanyl, or phenyl($C_{1-8}$)alkanyl;

$R_4$ is one to three substituents selected from the group consisting of hydrogen, hydroxy, methyl, methoxy, phenyl, bromo, fluoro, and chloro;

$R_5$ is hydrogen;

A is $CH_2CH_2$;

Y is O;

Z is O or NH; and enantiomers, diastereomers, tautomers, solvates, and pharmaceutically acceptable salts thereof.

Another embodiment of the present invention is directed to compounds of Formula (I) wherein:

G is —C(Z)N($R_1$)$R_2$, 1H-tetrazol-4-yl, 4H-[1,2,4]-oxadiazol-5-oxo-3-yl, 2-methylcarbonylaminophenyl, 3-furyl, quinolin-3-yl, thiophen-3-yl, pyridin-3-yl or pyridin-4-yl, $R_1$ is hydrogen, ethyl, or methyl, $R_2$ is methyl, ethyl, phenethyl, or hydrogen;

or $R_1$ and $R_2$ taken together with the nitrogen to which they are attached form pyrrolidin-1-yl, 3-hydroxypyrrolidin-1-yl, or 3-(S)-hydroxypyrrolidin-1-yl;

Z is NH or oxygen, $R_3$ is pyridin-2-ylmethyl, fur-3-ylmethyl, methyl, hydrogen, 3-methyl-2-butenyl, thiophene-2-ylmethyl, 2-propenyl, 1H-imidazol-2-ylmethyl, 2-phenethyl, thiazol-2-ylmethyl, benzyl, or allyl;

$R_4$ is one to three substituents selected from the group consisting of hydrogen, hydroxy, methyl, methoxy, phenyl, bromo, fluoro, and chloro;

$R_5$ is hydrogen

A is $CH_2CH_2$;

Y is O;

Z is O or NH; and enantiomers, diastereomers, tautomers, solvates, and pharmaceutically acceptable salts thereof.

Another embodiment of the present invention is directed to compounds of Formula (I) wherein:

G is —C(Z)N($R_1$)$R_2$, 1H-tetrazol-4-yl, 4H-[1,2,4]-oxadiazol-5-oxo-3-yl, 2-methylcarbonylaminophenyl, 3-furyl, quinolin-3-yl, thiophen-3-yl, pyridin-3-yl or pyridin-4-yl;

$R_1$ is hydrogen or ethyl;

$R_2$ is hydrogen or ethyl;

or $R_1$ and $R_2$ taken together with the nitrogen to which they are attached form 3-hydroxypyrrolidin-1-yl;

Z is NH or oxygen;

$R_3$ is pyridin-2-ylmethyl, fur-3-ylmethyl, fur-2-ylmethyl, methyl, hydrogen, 3-methyl-2-butenyl, thiophene-2-ylmethyl, 2-propenyl, 1H-imidazol-2-ylmethyl, 2-phenethyl, thiazol-2-ylmethyl, allyl, or benzyl;

$R_4$ is hydrogen, methoxy, or hydroxy;

$R_5$ is hydrogen;

A is $CH_2CH_2$;

Y is O;

Z is O or NH; and enantiomers, diastereomers, tautomers, solvates, and pharmaceutically acceptable salts thereof.

In certain embodiments of Formula (I) when $R_1$ and $R_2$ are taken together with the nitrogen to which they are attached to form a 5-7 membered cycloheteroalkyl optionally substituted with one to three substituents independently selected from the group consisting of $C_{1-8}$alkanyl, hydroxy($C_{1-8}$)alkanyl, hydroxy, amino, $C_{1-6}$alkanylamino, di($C_{1-6}$alkanyl)amino, and halogen; Z is oxygen.

In certain embodiments of Formula (I) when $R_1$ and $R_2$ are taken together with the nitrogen to which they are attached to form a pyrrolidinyl ring optionally substituted with hydroxy, Z is oxygen.

Another embodiment of the present invention is directed to compositions comprising a compound selected from the group consisting of:

a compound of Formula (I) wherein G is N,N-diethylaminocarbonyl; $R^3$ is 1H-imidazol-2-yl-methyl; $R^4$ is α'-hydroxy; $R^5$ is H; Y is O; and A is —$CH_2CH_2$—;

a compound of Formula (I) wherein G is N,N-diethylaminocarbonyl; $R^3$ is furan-3-yl-methyl; $R^4$ is α'-hydroxy; $R^5$ is H; Y is O; and A is —$CH_2CH_2$—;

a compound of Formula (I) wherein G is N,N-diethylaminocarbonyl; $R^3$ is H; $R^4$ is α'-hydroxy; $R^5$ is H; Y is O; and A is —$CH_2CH_2$—;

a compound of Formula (I) wherein G is N,N-diethylaminocarbonyl; $R^3$ is H; $R^4$ is α'-methoxy; $R^5$ is H; Y is O; and A is —$CH_2CH_2$—;

a compound of Formula (I) wherein G is N,N-diethylaminocarbonyl; $R^3$ is pyridin-2-yl-methyl; $R^4$ is H; $R^5$ is H; Y is O; A is —$CH_2CH_2$—;

a compound of Formula (I) wherein G is N,N-diethylaminocarbonyl; $R^3$ is furan-3-yl-methyl; $R^4$ is H; $R^5$ is H; Y is O; and A is —$CH_2CH_2$—;

a compound of Formula (I) wherein G is N,N-diethylaminocarbonyl; $R^3$ is thien-2-yl-methyl; $R^4$ is H; $R^5$ is H; Y is O; and A is —$CH_2CH_2$—;

a compound of Formula (I) wherein G is N,N-diethylaminocarbonyl; $R^3$ is benzyl; $R^4$ is H; $R^5$ is H; Y is O; and A is —$CH_2CH_2$—;

a compound of Formula (I) wherein G is pyridin-3-yl; $R^3$ is furan-3-yl methyl; $R^4$ is H; $R^5$ is H; Y is O; and A is —$CH_2CH_2$—;

a compound of Formula (I) wherein G is N,N-diethylaminocarbonyl; $R^3$ is furan-2-yl methyl; $R^4$ is H; $R^5$ is H; Y is O; and A is —$CH_2CH_2$—;

a compound of Formula (I) wherein G is N,N-diethylaminocarbonyl; $R^3$ is H; $R^4$ is α'-methyl; $R^5$ is H; Y is O; and A is —$CH_2CH_2$—;

a compound of Formula (I) wherein G is N,N-diethylaminocarbonyl; $R^3$ is H; $R^4$ is α'-phenyl; $R^5$ is H; Y is O; and A is —$CH_2CH_2$—;

a compound of Formula (I) wherein G is N,N-diethylaminocarbonyl; $R^3$ is H; $R^4$ is H; $R^5$ is H; Y is O; and A is —$CH_2CH_2$—;

a compound of Formula (I) wherein G is N,N-diethylaminocarbonyl; $R^3$ is H; $R^4$ is H; $R^5$ is H; Y is O; and A is —$CH_2CH_2$—;

a compound of Formula (I) wherein G is N,N-diethylaminocarbonyl; $R^3$ is H; $R^4$ is β"-bromo; $R^5$ is H; Y is O; and A is —$CH_2CH_2$—;

a compound of Formula (I) wherein G is N,N-diethylaminocarbonyl; $R^3$ is H; $R^4$ is H; $R^5$ is H; Y is O; and A is —$CH_2CH_2$—;

a compound of Formula (I) wherein G is N,N-diethylaminocarbonyl; $R^3$ is H; $R^4$ is α'-chloro; $R^5$ is H; Y is O; and A is —$CH_2CH_2$—;

a compound of Formula (I) wherein G is N,N-diethylaminocarbonyl; $R^3$ is H; $R^4$ is β"-fluoro; $R^5$ is H; Y is O; and A is —$CH_2CH_2$—;

a compound of Formula (I) wherein G is 2-methylcarbonylamino-phenyl; $R^3$ is H; $R^4$ is H; $R^5$ is H; Y is O; and A is —$CH_2CH_2$—; and a compound of Formula (I) wherein G is pyrrolidin-1-yl; $R^3$ is H; $R^4$ is H; $R^5$ is H; Y is O; and A is —$CH_2CH_2$—.

Another embodiment of the present invention is directed to compounds and compositions comprising a compound selected from the group consisting of:

9-(8-Aza-bicyclo[3.2.1]oct-3-yl)-9H-xanthene-3-carboxylic acid diethylamide;

9-(8-Furan-3-ylmethyl-8-aza-bicyclo[3.2.1]oct-3-ylidene)-9H-xanthene-3-carboxylic acid diethylamide;

9-(8-Benzyl-8-aza-bicyclo[3.2.1]oct-3-yl)-9H-xanthene-3-carboxylic acid diethylamide;

9-(8-Phenethyl-8-aza-bicyclo[3.2.1]oct-3-yl)-9H-xanthene-3-carboxylic acid diethylamide;

9-(8-Furan-2-ylmethyl-8-aza-bicyclo[3.2.1]oct-3-yl)-9H-xanthene-3-carboxylic acid diethylamide;

9-(8-Thiophen-2-ylmethyl-8-aza-bicyclo[3.2.1]oct-3-yl)-9H-xanthene-3-carboxylic acid diethylamide;
9-(8-Pyridin-2-ylmethyl-8-aza-bicyclo[3.2.1]oct-3-yl)-9H-xanthene-3-carboxylic acid diethylamide;
9-[8-(1H-Imidazol-2-ylmethyl)-8-aza-bicyclo[3.2.1]oct-3-yl]-9H-xanthene-3-carboxylic acid diethylamide;
9-(8-Methyl-8-aza-bicyclo[3.2.1]oct-3-yl)-9H-xanthene-3-carboxylic acid diethylamide;
3-(3-Pyridin-3-yl-9H-xanthen-9-yl)-8-aza-bicyclo[3.2.1]octane;
8-Furan-3-ylmethyl-3-(3-pyridin-3-yl-9H-xanthen-9-yl)-8-aza-bicyclo[3.2.1]-octane;
3-(3-Furan-3-yl-9H-xanthen-9-yl)-8-aza-bicyclo[3.2.1]octane;
3-(3-Thiophen-3-yl-9H-xanthen-9-yl)-8-aza-bicyclo[3.2.1]octane;
N-{2-[9-(8-Aza-bicyclo[3.2.1]oct-3-yl)-9H-xanthen-3-yl]-phenyl}-acetamide;
3-[9-(8-Aza-bicyclo[3.2.1]oct-3-yl)-9H-xanthen-3-yl]-quinoline;
3-(3-Pyridin-3-yl-9H-xanthen-9-yl)-8-thiophen-2-ylmethyl-8-aza-bicyclo[3.2.1]octane;
8-Pyridin-2-ylmethyl-3-(3-pyridin-3-yl-9H-xanthen-9-yl)-8-aza-bicyclo[3.2.1]octane;
8-Benzyl-3-(3-pyridin-3-yl-9H-xanthen-9-yl)-8-aza-bicyclo[3.2.1]octane;
8-Phenethyl-3-(3-pyridin-3-yl-9H-xanthen-9-yl)-8-aza-bicyclo[3.2.1]octane;
N-{2-[9-(8-Furan-3-ylmethyl-8-aza-bicyclo[3.2.1]oct-3-yl)-9H-xanthen-3-yl]-phenyl}-acetamide;
N-{2-[9-(8-Thiophen-2-ylmethyl-8-aza-bicyclo[3.2.1]oct-3-yl)-9H-xanthen-3-yl]-phenyl}-acetamide;
N-{2-[9-(8-Pyridin-2-ylmethyl-8-aza-bicyclo[3.2.1]oct-3-yl)-9H-xanthen-3-yl]-phenyl}-acetamide;
N-{2-[9-(8-Benzyl-8-aza-bicyclo[3.2.1]oct-3-yl)-9H-xanthen-3-yl]-phenyl}-acetamide;
N-{2-[9-(8-Phenethyl-8-aza-bicyclo[3.2.1]oct-3-yl)-9H-xanthen-3-yl]-phenyl}-acetamide;
N-{2-[9-(8-Allyl-8-aza-bicyclo[3.2.1]oct-3-yl)-9H-xanthen-3-yl]-phenyl}-acetamide;
3-(3-Pyridin-4-yl-9H-xanthen-9-yl)-8-aza-bicyclo[3.2.1]octane;
3-(3-Pyridin-4-yl-9H-xanthen-9-yl)-8-thiophen-2-ylmethyl-8-aza-bicyclo[3.2.1]octane;
8-Pyridin-2-ylmethyl-3-(3-pyridin-4-yl-9H-xanthen-9-yl)-8-aza-bicyclo[3.2.1]octane;
8-Benzyl-3-(3-pyridin-4-yl-9H-xanthen-9-yl)-8-aza-bicyclo[3.2.1]octane;
8-Phenethyl-3-(3-pyridin-4-yl-9H-xanthen-9-9-yl)-8-aza-bicyclo[3.2.1]octane;
8-Furan-3-ylmethyl-3-(3-pyridin-4-yl-9H-xanthen-9-yl)-8-aza-bicyclo[3.2.1]octane;
8-(1H-Imidazol-2-ylmethyl)-3-(3-pyridin-3-yl 9 H-xanthen-9-yl)-8-aza-bicyclo[3.2.1]octane;
9-(8-Aza-bicyclo[3.2.1]oct-3-yl)-5-methoxy-9H-xanthene-3-carboxylic acid diethylamide;
9-(8-Aza-bicyclo[3.2.1]oct-3-yl)-5-hydroxy-9H-xanthene-3-carboxylic acid diethylamide;
9-(8-Furan-3-ylmethyl-8-aza-bicyclo[3.2.1]oct-3-yl)-5-hydroxy-9H-xanthene-3-carboxylic acid diethylamide;
5-Hydroxy-9-[8-(1H-imidazol-2-ylmethyl)-8-aza-bicyclo[3.2.1]oct-3-yl]-9H-xanthene-3-carboxylic acid diethylamide;
9-(8-Aza-bicyclo[3.2.1]oct-3-yl)-5-phenyl-9H-xanthene-3-carboxylic acid diethylamide;
9-(8-Aza-bicyclo[3.2.1]oct-3-yl)-7-fluoro-9H-xanthene-3-carboxylic acid diethylamide;
9-(8-Aza-bicyclo[3.2.1]oct-3-yl)-7-bromo-9H-xanthene-3-carboxylic acid diethylamide;
[9-(8-Aza-bicyclo[3.2.1]oct-3-yl)-9H-xanthen-3-yl]-pyrrolidin-1-yl-methanone;
9-(8-Aza-bicyclo[3.2.1]oct-3-yl)-5-methyl-9H-xanthene-3-carboxylic acid diethylamide;
9-(8-Aza-bicyclo[3.2.1]oct-3-yl)-5-chloro-9H-xanthene-3-carboxylic acid diethylamide;
3-[3-(1H-Tetrazol-5-yl)-9H-xanthen-9-yl]-8-aza-bicyclo[3.2.1]octane;
8-Furan-3-ylmethyl-3-[3-(1H-tetrazol-5-yl)-9H-xanthen-9-yl]-8-aza-bicyclo[3.2.1]octane;
3-[3-(1H-Tetrazol-5-yl)-9H-xanthen-9-yl]-8-thiophen-2-ylmethyl-8-aza-bicyclo[3.2.1]octane;
8-Pyridin-2-ylmethyl-3-[3-(1H-tetrazol-5-yl)-9H-xanthen-9-yl]-8-aza-bicyclo[3.2.1]octane;
8-Benzyl-3-[3-(1H-tetrazol-5-yl)-9H-xanthen-9-yl]-8-aza-bicyclo[3.2.1]octane;
8-Phenethyl-3-[3-(1H-tetrazol-5-yl)-9H-xanthen-9-yl]-8-aza-bicyclo[3.2.1]octane;
3-(5-Methoxy-3-pyridin-3-yl-9H-xanthen-9-yl)-8-aza-bicyclo[3.2.1]octane;
9-(8-Aza-bicyclo[3.2.1]oct-3-yl)-6-pyridin-3-yl-9H-xanthen-4-ol;
9-(8-Furan-3-ylmethyl-8-aza-bicyclo[3.2.1]oct-3-yl)-6-pyridin-3-yl-9H-xanthen-4-ol;
6-Pyridin-3-yl-9-(8-thiophen-2-ylmethyl-8-aza-bicyclo[3.2.1]oct-3-yl)-9H-xanthen-4-ol;
6-Pyridin-3-yl-9-(8-pyridin-2-ylmethyl-8-aza-bicyclo[3.2.1]oct-3-yl)-9H-xanthen-4-ol;
9-(8-Benzyl-8-aza-bicyclo[3.2.1]oct-3-yl)-6-pyridin-3-yl-9H-xanthen-4-ol;
9-(8-Phenethyl-8-aza-bicyclo[3.2.1]oct-3-yl)-6-pyridin-3-yl-9H-xanthen-4-ol;
3-(3-Bromo-5-methoxy-9H-xanthen-9-yl)-8-aza-bicyclo[3.2.1]octane;
N-{2-[9-(8-Aza-bicyclo[3.2.1]oct-3-yl)-5-methoxy-9H-xanthen-3-yl]-phenyl}-acetamide;
N-{2-[9-(8-Aza-bicyclo[3.2.1]oct-3-yl)-5-hydroxy-9H-xanthen-3-yl]-phenyl}-acetamide;
N-{2-[9-(8-Furan-3-ylmethyl-8-aza-bicyclo[3.2.1]oct-3-yl)-5-hydroxy-9H-xanthen-3-yl]-phenyl}-acetamide;
N-{2-[5-Hydroxy-9-(8-thiophen-2-ylmethyl-8-aza-bicyclo[3.2.1]oct-3-yl)-9H-xanthen-3-yl]-phenyl}-acetamide;
N-{2-[5-Hydroxy-9-(8-pyridin-2-ylmethyl-8-aza-bicyclo[3.2.1]oct-3-yl)-9H-xanthen-3-yl]-phenyl}-acetamide;
N-{2-[9-(8-Benzyl-8-aza-bicyclo[3.2.1]oct-3-yl)-5-hydroxy-9H-xanthen-3-yl]-phenyl}-acetamide;
N-{2-[5-Hydroxy-9-(8-phenethyl-8-aza-bicyclo[3.2.1]oct-3-yl)-9H-xanthen-3-yl]-phenyl}-acetamide;
N-(2-{5-Hydroxy-9-[8-(1H-imidazol-2-ylmethyl)-8-aza-bicyclo[3.2.1]oct-3-yl]-xanthen-3-yl}-phenyl)-acetamide;
9-(8-Aza-bicyclo[3.2.1]oct-3-yl)-N,N-diethyl-9H-xanthene-3-carboxamidine;
N,N-Diethyl-9-(8-furan-3-ylmethyl-8-aza-bicyclo[3.2.1]oct-3-yl)-9H-xanthene-3-carboxamidine;
N,N-Diethyl-9-(8-thiophen-2-ylmethyl-8-aza-bicyclo[3.2.1]oct-3-yl)-9H-xanthene-3-carboxamidine;
N,N-Diethyl-9-(8-pyridin-2-ylmethyl-8-aza-bicyclo[3.2.1]oct-3-yl)-9H-xanthene-3-carboxamidine;
9-(8-Benzyl-8-aza-bicyclo[3.2.1]oct-3-yl)-N,N-diethyl-9H-xanthene-3-carboxamidine;
N,N-Diethyl-9-(8-phenethyl-8-aza-bicyclo[3.2.1]oct-3-yl)-9H-xanthene-3-carboxamidine;
3-(9-Piperidin-4-yl-9H-xanthen-3-yl)-4H-[1,2,4]oxadiazol-5-one;

3-[9-(1-Furan-3-ylmethyl-piperidin-4-yl)-9H-xanthen-3-yl]-4H-[1,2,4]oxadiazol-5-one;

3-[9-(8-Pyridin-2-ylmethyl-8-aza-bicyclo[3.2.1]oct-3-yl)-9H-xanthen-3-yl]-4H-[1,2,4]oxadiazol-5-one;

[9-(8-Aza-bicyclo[3.2.1]oct-3-yl)-9H-xanthen-3-yl]-(3-hydroxy-pyrrolidin-1-yl)-methanone;

[9-(8-Furan-3-ylmethyl-8-aza-bicyclo[3.2.1]oct-3-yl)-9H-xanthen-3-yl]-(3-hydroxy-pyrrolidin-1-yl)-methanone;

(3-Hydroxy-pyrrolidin-1-yl)-[9-(8-thiophen-2-ylmethyl-8-aza-bicyclo[3.2.1]oct-3-yl)-9H-xanthen-3-yl]-methanone;

(3-Hydroxy-pyrrolidin-1-yl)-[9-(8-pyridin-2-ylmethyl-8-aza-bicyclo[3.2.1]oct-3-yl)-9H-xanthen-3-yl]-methanone;

[9-(8-Benzyl-8-aza-bicyclo[3.2.1]oct-3-yl)-9H-xanthen-3-yl]-(3-hydroxy-pyrrolidin-1-yl)-methanone;

(3-Hydroxy-pyrrolidin-1-yl)-[9-(8-phenethyl-8-aza-bicyclo[3.2.1]oct-3-yl)-9H-xanthen-3-yl]-methanone;

and enantiomers, diastereomers, tautomers, solvates, or pharmaceutically acceptable salts thereof.

Another embodiment of the present invention is a composition comprising the dextrorotatory enantiomer of a compound of formula (I), wherein said composition is substantially free from the levorotatory isomer of said compound. In the present context, substantially free means less than 25%, preferably less than 10%, more preferably less than 5%, even more preferably less than 2% and even more preferably less than 1% of the levorotatory isomer calculated as.

$$\% \text{ levorotatory} = \frac{\text{(mass levorotatory)}}{\text{(mass dextrorotatory)} + \text{(mass levorotatory)}} \times 100$$

Another embodiment of the present invention is a composition comprising the levorotatory enantiomer of a compound of formula (I) wherein said composition is substantially free from the dextrorotatory isomer of said compound. In the present context, substantially free from means less than 25%, preferably less than 10%, more preferably less than 5%, even more preferably less than 2% and even more preferably less than 1% of the dextrorotatory isomer calculated as $$\% \text{ dextrorotatory} = \frac{\text{(mass dextrorotatory)}}{\text{(mass dextrorotatory)} + \text{(mass levorotatory)}} \times 100$$

In certain embodiments, the present invention provides the endo isomer of a compound of formula (I) wherein said compound is substantially free from the exo isomer of said compound. In certain embodiments, the present invention provides compositions comprising the endo isomer of a compound of formula (I) wherein said composition is substantially free from the exo isomer of said compound. In the present context, substantially free means less than 25%, preferably less than 10%, more preferably less than 5%, even more preferably less than 2% and even more preferably less than 1% of the exo isomer.

In certain embodiments, the present invention provides the exo isomer of a compound of formula (I) wherein said compound is substantially free from the endo isomer of said compound. In certain embodiments, the present invention provides compositions comprising the exo isomer of a compound of formula (I) wherein said composition is substantially free from the endo isomer of said compound. In the present context, substantially free means less than 25%, preferably less than 10%, more preferably less than 5%, even more preferably less than 2% and even more preferably less than 1% of the endo isomer.

In other embodiments, compositions of the present invention comprise a mixture of the exo and endo isomers of a compound of formula (I).

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as analgesics is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The compounds of the present invention may be used to treat mild to severe pain in warm-blooded animals such as humans by administration of an analgesically effective dose. The dosage range would be from about 0.1 mg to about 15,000 mg, in particular from about 50 mg to about 3500 mg or, more particularly from about 100 mg to about 1000 mg of active ingredient in a regimen of about 1 to 4 times per day for an average (70 kg) human; although, it is apparent to one skilled in the art that the therapeutically effective amount for active compounds of the invention will vary as will the types of pain being treated.

For oral administration, a pharmaceutical composition is preferably provided in the form of tablets containing 0.01, 10.0, 50.0, 100, 150, 200, 250, and 500 milligrams of the active ingredient for the symptomatic adjustment of the dosage to the subject to be treated.

Examples of pain intended to be within the scope of the present invention include, but are not limited to, inflammatory pain, centrally mediated pain, peripherally mediated pain, visceral pain, structural or soft tissue injury related pain, progressive disease related pain, neuropathic pain and acute pain such as caused by acute injury, trauma or surgery and chronic pain such as headache and that caused by neuropathic conditions, post-stroke conditions, cancer, and migraine.

Compounds of the present invention are also useful as immunosuppressants, antiinflammatory agents, agents for the treatment and prevention of neurological and psychiatric conditions, for instance, depression and Parkinson's disease, agents for the treatment of urological and reproductive conditions, for instance, urinary incontinence and premature ejaculation, medicaments for drug and alcohol abuse, agents for treating gastritis and diarrhea, cardiovascular agents and cardioprotective agents and agents for the treatment of respiratory diseases.

The compounds of the present invention are also useful in treating pain caused by osteoarthritis, rheumatoid arthritis, fibromyalgia, migraine, headache, toothache, burn, sunburn, snake bite (in particular, venomous snake bite), spider bite, insect sting, neurogenic bladder, benign prostatic hypertrophy, interstitial cystitis, rhinitis, contact dermatitis/hypersensitivity, itch, eczema, pharyngitis, mucositis, enteritis, cellulites, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, post-herpetic neuralgia, trigeminal neuralgia, cluster headache, migraine headache, peripheral neuropathy, bilateral peripheral neuropathy, diabetic neuropathy, postherpetic neuralgia, trigeminal neuralgia, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, sinus headache, tension headache, labor, childbirth, menstrual cramps, and cancer.

In regard to the use of the present compounds in treatment of the disases or conditions such as those listed above, a therapeutically effective dose can be determined by persons skilled in the art by the use of established animal models. Such a dose would likely fall in the range of from about 0.01 mg to about 15,000 mg of active ingredient administered 1 to 4 times per day for an average (70 kg) human.

General Synthetic Methods

Representative compounds of the present invention can be synthesized in accordance with the general synthetic methods described below and are illustrated in the schemes that follow. Since the schemes are an illustration, the invention should not be construed as being limited by the chemical reactions and conditions expressed. The preparation of the various starting materials used in the schemes is well within the skill of persons versed in the art.

The preparation of compounds of this invention is illustrated in Schemes 1 and 2. Both schemes proceed with the same overall strategy. In stage 1, intermediates 1A and 1B is prepared with two benzene rings connected by a linker —Y—. The linker —Y— may be oxygen or sulfur. One benzene ring bears a group, Q, which is a group readily transformable to a substituent G as defined herein. Examples of such Q groups are fluoro, bromo, cyano, iodo, carboxy, or trifluoromethanesulfonyloxy. One benzene ring must bear a carboxylic acid, or a precursor to a carboxylic acid, positioned ortho to the linker —Y—. Schemes 1 and 2 differ in that in scheme 1, the carboxylic acid is on the benzene ring bearing the Q group (1A) while in scheme 2 the carboxylic acid function is on the benzene ring which does not bear the group Q (1B).

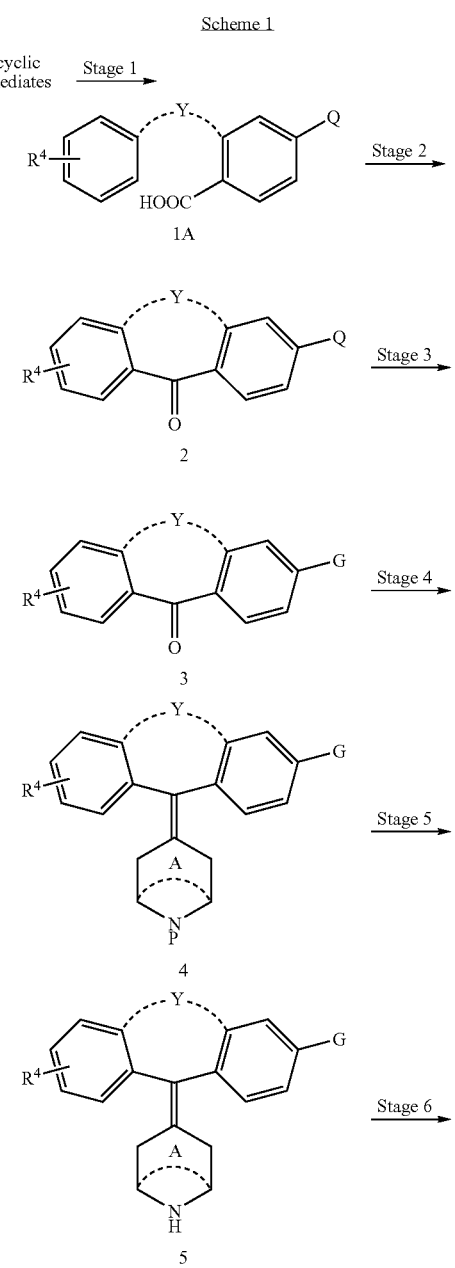

-continued

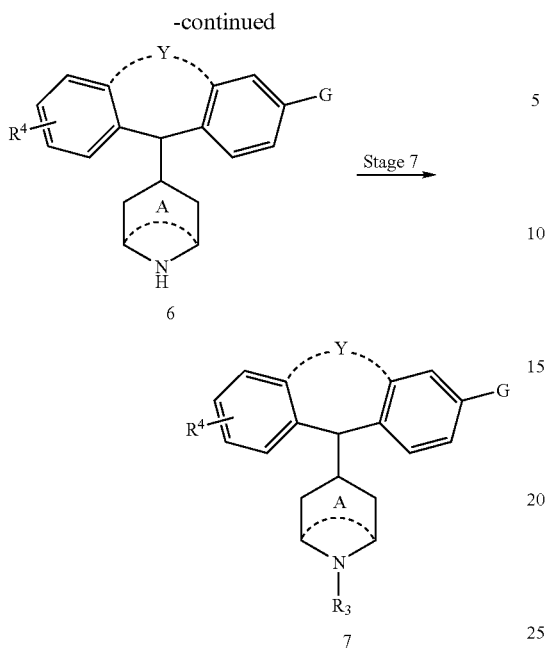

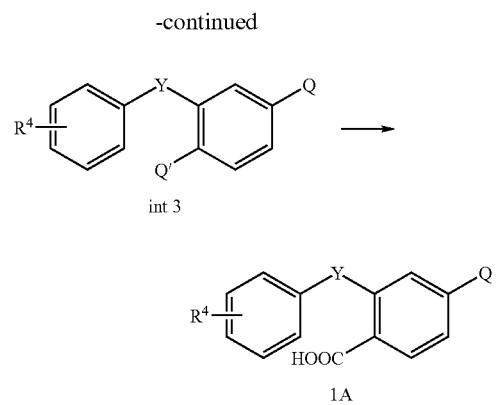

For Scheme 2, Stage 1, in order to prepare 1B compounds, the bridge may be constructed by nucleophilic aromatic displacement of fluoride from intermediate int 5 by phenoxides or thiophenoxides (int 4). The 1B compounds are then obtained by hydrolysis of int 6 with an alkali metal hydroxide.

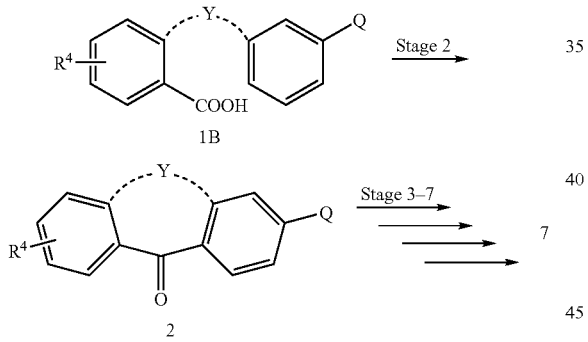

In stage 1 the linker —Y— is constructed between two monocyclic intermediates. For Scheme 1, Stage 1, the bridge may be constructed by nucleophilic aromatic displacement of fluoride from intermediate int 2 (where Q' is an electron withdrawing group, readily convertible to a carboxylic acid, for instance cyano or alkoxycarbonyl) by a phenoxide or thiophenoxide, int 1. The 1A compounds are then obtained by hydrolysis of int 3 with an alkali metal hydroxide.

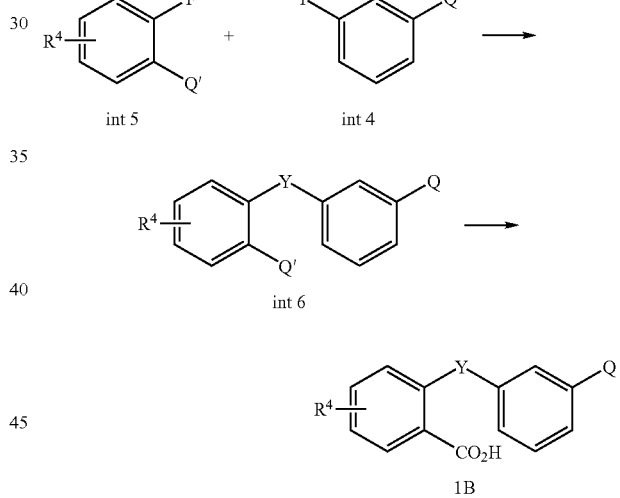

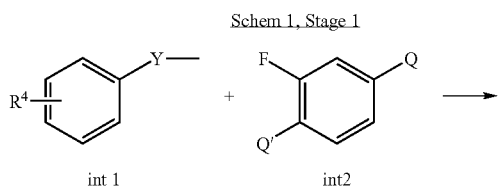

Following Stage 1, the schemes merge. In Stage 2, compounds 1A and 1B are converted by cycloacylation to ketones 2, using, for instance, $BF_3 \cdot Et_2O$-trifluoroacetic acid or polyphosphoric acid. Alternatively, the cyclization may be effected by converting acid 1A and 1B to an acid chloride, for instance with thionyl chloride, followed by Friedel-Crafts ring closure in the presence of a Lewis acid, such as aluminum chloride.

In addition, Stages 1 and 2 may be performed in reverse to give compounds 2 that are ready to enter Stage 3. For instance, Friedel-Crafts acylation between a methyl ether (int 7) and an appropriately substituted acid chloride (int 8) provides the ketone (int 9), which is simultaneously demethylated under the reaction conditions. Subsequent formation of the bridge —Y— via a nucleophilic aromatic displacement gives compounds 2 that are ready to enter Stage 3.

Scheme 3, Stages 1 and 2

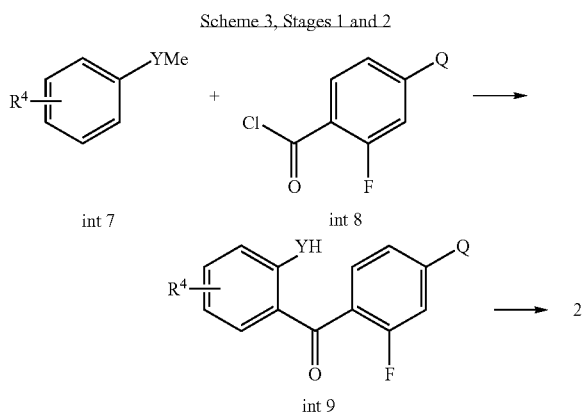

In stage 3, the Q function of compounds 2 is converted into group G, which may be —C(Z)N(R$_1$)R$_2$, an aryl substituent, or an appropriate heterocycle as defined herein, to give compounds of formula 3. When the Q function of compounds 2 is a halogen or trifluoromethanesulfonyloxy, it may be converted to an ester via alkoxycarbonylation using carbon monoxide, an aliphatic alcohol, a trialkanyl amine, and a palladium catalyst such as bis(triphenylphosphine) palladium(II) dichloride. Subsequently, when Q is an ester, the ester may be hydrolyzed to a carboxylic acid. The carboxylic acid may then be coupled with ammonia, a primary amine, or a secondary amine to form a primary, secondary or tertiary amide, respectively. Alternatively, the conversion of a carboxylic acid to an amide may be carried out via an acid chloride using thionyl chloride, oxalyl chloride, or the like, followed by a Schotten-Baumann reaction using ammonia or an amine in the presence of an alkali metal hydroxide. Alternatively, the conversion of a carboxylic acid to an amide may be carried out via the use of peptide coupling agents such as 1,3-dicyclohexylcarbondiimide (DCC), O-(7-azabenzotriazol-1-yl)-N,N,N',N'-tetramethyluronium hexafluorophosphate (HATU), O-benzotriazol-1-yl-N,N,N',N'-tetramethyluronium hexafluorophosphate (HBTU), or the like. Alternatively, the ester may be converted directly to the amide by the action of a dimethylaluminum amide.

Instead of proceeding to compounds 3 via an ester, one may effect the transformation of the group Q to a substituent G (wherein G is an amidino or heterocycle) by way of a nitrile. Synthesis of the nitrile may be accomplished by treatment of the compounds 2 (when Q is bromo or trifluoromethanesulfonyloxy) with Zn(CN)$_2$ and a palladium catalyst such as (Ph$_3$P)$_4$Pd or by treatment of the compounds 2 with CuCN at elevated temperatures. For the synthesis of amidino functional groups, the nitrile is treated with hydroxylamine under basic conditions to afford an oxime. Treatment of the oxime with a primary or secondary amine, CuCl, and an alkali metal carbonate under microwave irradiation in an alcoholic solvent provides the amidino compounds of the present invention. Microwave accelerated reactions may be performed using either a CEM Discover or a Personal Chemistry Smith Synthesizer microwave instrument. The oxime described above is instrumental in the preparation of compounds wherein G is a heterocycle. The oxime may be cyclized with a variety of electrophiles known to one versed in the art to give the heterocycles of the present invention. For instance, reaction of an oxime with CDI provides oxadiazolones, and treatment of the oxime with TCDI provides the corresponding oxadiazolethiones. Similarly, the treatment of the oxime with thionyl chloride in the presence of a tertiary amine gives oxathiadiazoles of the present invention.

Alternatively, compounds where Q is a halogen atom or a trifluoromethanesulfonyloxy group may participate in transition metal-mediated coupling reactions such as Suzuki, Stille or Negishi chemistry.

To perform stage 4, a 9-azabicyclo[3.3.1]nonanylidene or 8-azabicyclo[3.2.1]octanylidene function is attached to the tricyclic system, replacing the ketone to give compounds of type 4. This transformation may be carried out by McMurray condensation of ketones 3 with 9-azabicyclo[3.3.1]nonan-3-one or 8-azabicyclo[3.2.1]octan-3-one brought about by a lower valent titanium reagent such as the reagent obtained from addition of titanium tetrachloride to zinc dust. Alternatively, a 3-(9-azabicyclo[3.3.1]nonanyl)magnesium halide or 3-(8-aza-bicyclo[3.2.1]octanyl)magnesium halide may be added to ketone to afford carbinols. Dehydration of such carbinols with acidic reagents such as formic acid, sulfuric acid or trifluoroacetic acid gives rise to compounds of type 4. If desired, the operation of stages 3 and 4 may be carried out in reverse order. As illustrated in Schemes 1 and 2, the nitrogen atoms of compounds 4 may bear a group P. This group may be an alkanyl, alkenyl or aralkanyl in which case they are the therapeutically useful products of this invention. The group P may also be trifluoromethylcarbonyl, alkoxycarbonyl or aralkoxycarbonyl.

The olefin in compound 4 may be reduced to obtain the corresponding alkane (stage 5). This transformation may be carried out by treatment of compounds 4 with hydrogen iodide in chloroform or a mixture of trimethylsilyl iodide and ethanol in chloroform to yield compounds 5. The group P can be removed to produce free amines 6 (stage 6). This transformation may be carried out using certain acidic reagents such as hydrogen bromide or trimethylsilyl iodide. Or, when P is a trifluoromethylcarbonyl, basic reagents such as potassium carbonate in an alcoholic solvent may be used for the removal of P. Compounds of type 5 bearing readily cleavable groups such as methyl, allyl or benzyl may be transformed into the aforementioned alkoxycarbonyl derivatives by treatment with alkanylchloroformates such as ethyl chloroformate or 1-chloroethyl chloroformate.

Stages 5 and 6 may be performed in reverse to give compounds 6. In this case, group P is removed as described above before the olefin is reduced.

Finally, the secondary amines 6 may be converted to a compound of formula 7 as shown in Stage 7. These transformations may be carried out by reductive alkylation using a carbonyl compound and a reducing agent such as sodium borohydride, sodium cyanoborohydride, sodium triacetoxyborohydride, or tetramethylammonium triacetoxyborohydride. Alternatively, the amine of formula 6 may be treated with an appropriate alkylating agent, such as a halide- or tosylate-substituted alkanyl, alkenyl or aralkyl group and an organic or inorganic base.

Finally, the transformation of compound 4 into compound 7 may also be performed by performing stages 5 through 7 in the following order: stage 6, followed by stage 7, followed by stage 5. In this case, group P is removed prior to the introduction of R$_3$ by the methods described above. The final step consists of reduction of the olefin to the corresponding saturated carbon-carbon bond of Formula (I).

Desired end products of the present invention may include chemical modifications at R$_4$. Such transformations may include the dealkylation of lower alkyl ethers to give their corresponding alcohols, using reagents such as boron trihalides. Compounds where R$_4$ is a halogen atom may participate in transition metal-mediated coupling reactions such as Suzuki, Stille or Negishi chemistry.

Compounds of Formula (I) that are chiral may be separated into their enantiomers by chromatography on a chiral stationary phase following Stages 4, 5, or 6. Alternatively, the basic compounds of types 5, 6, and 7 may be converted to diastereomeric salts by mixture with a chiral acid and resolved into their enantiomers by fractional crystallization.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and heptanes are typical hydrocarbon solvents and dichloromethane and dichloroethane are representative halogenated hydrocarbon solvents. In those cases where the product is isolated as the acid addition salt the free base may be obtained by techniques known to those skilled in the art. In those cases in which the product is isolated as an acid addition salt, the salt may contain one or more equivalents of the acid. Enantiomers of the compounds of the present invention may be separated using chiral HPLC.

Representative compounds of the present invention can be synthesized in accordance with the general synthetic methods described above and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

| Abbreviations | |
|---|---|
| CDI = | 1,1'-carbonyldiimidazole |
| DBN = | 1,8-diazabicyclo[5.4.0]undec-7-ene |
| DMF = | N,N-dimethylformamide |
| dppf = | diphenylphosphinoferrocene |
| Et = | ethyl |
| h = | hour(s) |
| HBTU = | O-benzotriazol-1-yl-N,N,N',N'-tetramethyluronium hexafluorophosphate |
| Me = | methyl |
| min = | minute(s) |
| TCDI = | 1,1'-thiocarbonyldiimidazole |
| PPA = | polyphosphoric acid |
| t-Boc = | tert-butoxycarbonyl |
| TFA = | trifluoroacetic acid |
| THF = | tetrahydrofuran |
| µW = | microwave irradiation |
| W = | watt(s) |

Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

All publications and patent documents cited above are hereby incorporated by reference in their entirety for all purposes to the same extent as if each were so individually denoted.

EXAMPLES

Example A

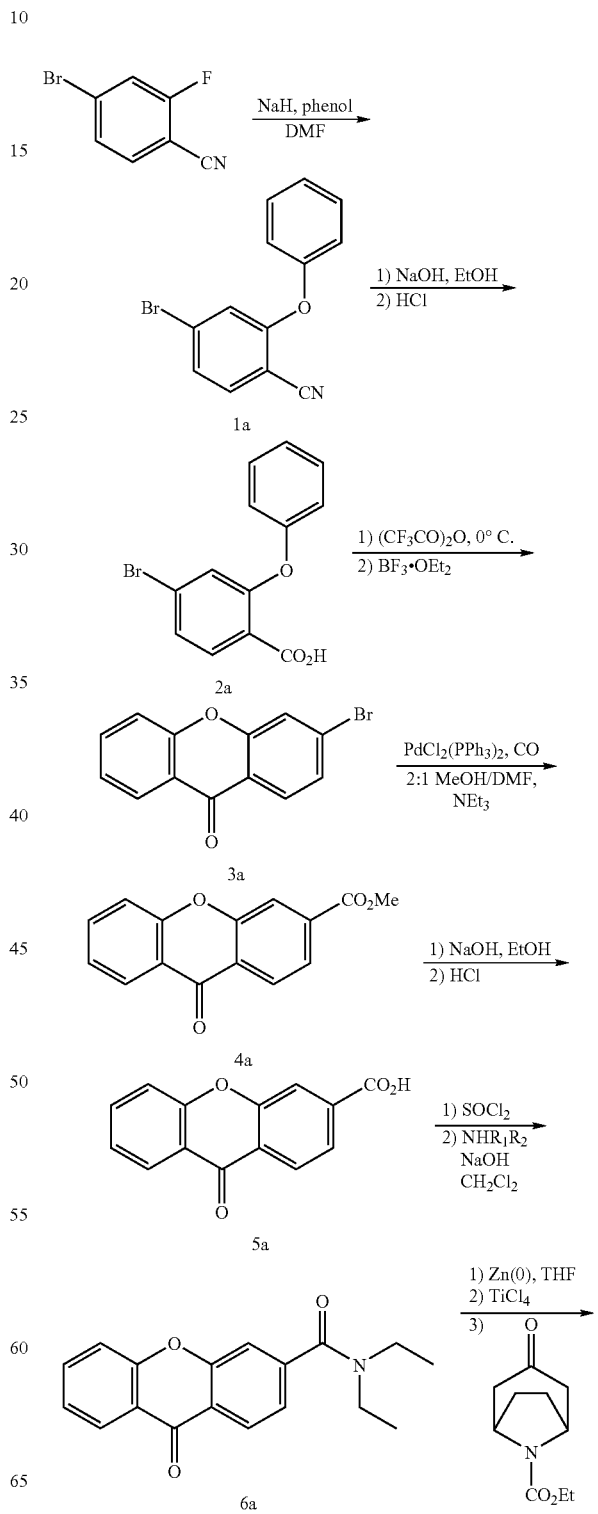

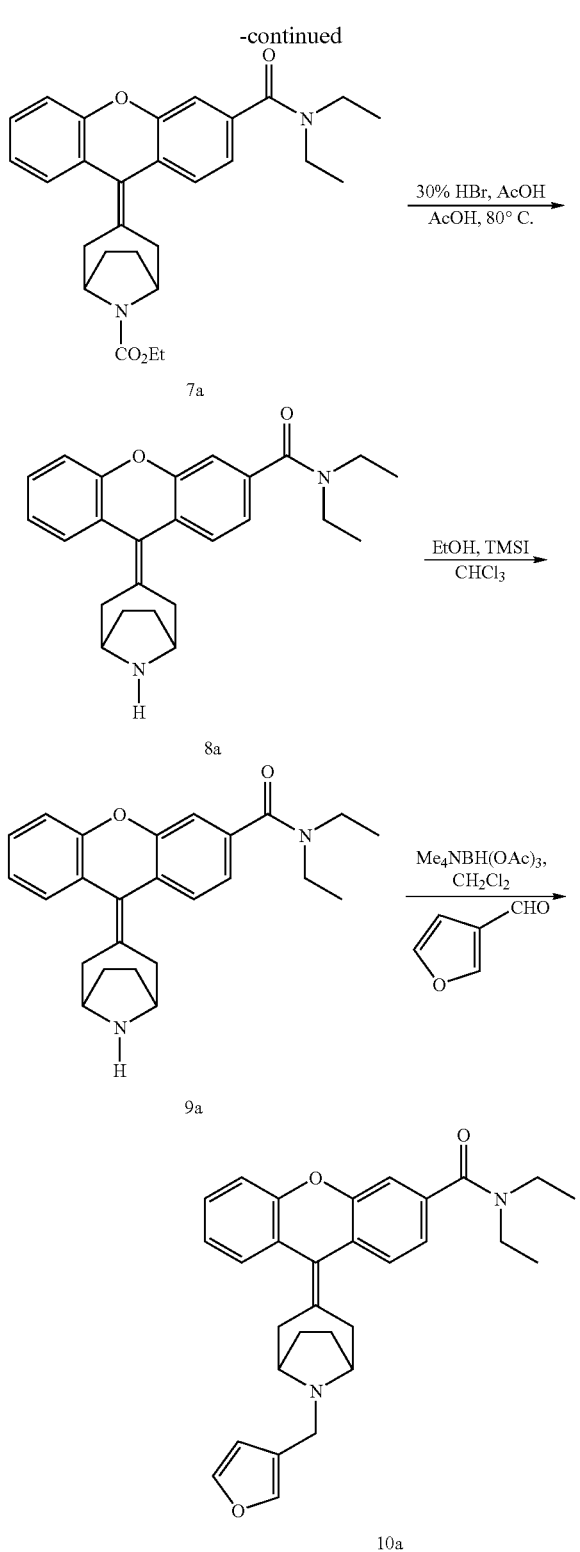

Procedure 1

4-Bromo-2-phenoxybenzonitrile, 1a

Sodium hydride (12 g, 300 mmol; 60% by wt) was weighed into a flask and washed free of oil with several hexane rinsings. The hexanes were decanted and discarded and DMF was added to the flask. A solution of phenol (23.5 g, 250 mmol) in DMF (100 mL) was added dropwise to the NaH mixture and stirred at rt. A solution of 4-bromo-2-fluorobenzonitrile (50 g, 250 mmol) in DMF (100 mL) was added dropwise. Upon complete addition, the reaction was heated to reflux for 20 h. The reaction was cooled to rt, and poured into cold 1 N NaOH. A fine, tan precipitate formed and which was collected by vacuum filtration to give 62.04 g (226 mmol) of title compound 4-bromo-2-phenoxybenzonitrile, 1a. MS m/z (MH$^+$) 277.

Procedure 2

4-Bromo-2-phenoxybenzoic acid, 2a

To a solution of 4-bromo-2-phenoxybenzonitrile, 1a (35.3 g, 129 mmol) in EtOH (130 mL) was added a 20% aqueous NaOH solution (340 mL). The reaction was heated to reflux for 20 h. The mixture was cooled to rt and poured into 6 N HCl and a precipitate formed. The solid was collected by vacuum filtration and dissolved in 3:1 THF-diethyl ether and washed with brine. The organic phase was dried over magnesium sulfate and concentrated. The solids were dried under vacuum at 60° C. overnight to give 35.1 g (128 mmol) of tilte compound 4-bromo-2-phenoxybenzoic acid, 2a. MS m/z (MH$^+$) 292.

Procedure 3

3-Bromo-xanthen-9-one, 3a

To a suspension of 4-bromo-2-phenoxybenzoic acid, 2a (35.1 g, 120 mmol) in. methylene chloride (350 mL) at 0° C. was added dropwise trifluoroacetic anhydride (20.3 mL, 144 mmol), and the reaction was stirred for 15 min. Boron trifluoride diethyl etherate (1.46 mL, 12.0 mmol) was added dropwise. The reaction became homogeneous upon stirring for 1 h at rt. The reaction was poured into 1 N NaOH, and the organic phase was dried over magnesium sulfate, filtered, and concentrated to give title compound 3-bromo-xanthen-9-one, 3a (32.14 g, 116 mmol). MS m/z (MH$^+$) 275.

Procedure 4

9-Oxo-9H-xanthene-3-carboxylic acid methyl ester, 4a

To a solution of 3-bromo-xanthen-9-one, 3a (20 g, 72.2 mmol) in a 2:1 MeOH/DMF solution (600 mL) was added triethylamine (40 mL, 290 mmol) and the solution was degassed with argon. Dichlorobis(triphenylphosphine)palladium(II) (2.0 g, 2.85 mmol) was added, and the reaction was transferred to a pressure vessel and charged with 150 psi of CO (g). The reaction was heated at 90° C. for 24 h. Upon completion, the reaction was cooled to 40° C. and methylene chloride was added. The reaction was filtered while warm and evaporated to provide the crude product. Recrystallization from ethanol gave 16.62 g (65.4 mmol) of title compound 9-oxo-9H-xanthene-3-carboxylic acid methyl ester, 4a. MS m/z (MH$^+$) 255.

Procedure 5

9-Oxo-9H-xanthene-3-carboxylic acid, 5a

A suspension of 9-oxo-9H-xanthene-3-carboxylic acid methyl ester, 4a (16.6 g, 65.3 mmol) in 3 N NaOH (250 mL)

and EtOH (250 mL) was heated to reflux for 1 h. The EtOH was evaporated and the reaction was poured into 6 N HCl over ice and extracted with 1:1 THF/diethyl ether. The combined organic phases were washed with brine, dried over magnesium sulfate, filtered and evaporated to provide 13.35 g (55.6 mmol) of title compound 9-oxo-9H-xanthene-3-carboxylic acid, 5a after drying in a vacuum oven at 50° C overnight.

Procedure 6

9-Oxo-9H-xanthene-3-carboxylic acid diethylamide, 6a

To a suspension of 9-oxo-9H-xanthene-3-carboxylic acid, 5a (13.4 g, 55.6 mmol) in methylene chloride (220 mL) was added thionyl chloride (24.4 mL, 330 mmol). The mixture was heated to reflux for 6 h, adding approximately 10 mL of additional thionyl chloride per hour until the reaction became homogeneous. At that time, the thionyl chloride and solvent were removed under vacuum and the remaining residue was diluted with an additional 220 mL methylene chloride. To the suspension was added ice cold 1.5 N NaOH (100 mL), methylene chloride (100 mL), and diethylaminediethylamine (17 mL, 166 mmol). After stirring for 15 min at rt, the organic phase was separated and washed with HCl and brine, dried over magnesium sulfate, filtered and concentrated to yield title compound 9-oxo-9H-xanthene-3-carboxylic acid diethylamide, 6a (14.7 g, 49.8 mmol). MS m/z (MH$^+$) 296.

Procedure 7

3-(3-Diethylcarbamoyl-xanthen-9-ylidene)-8-aza-bicyclo[3.2.1]octane-8-carboxylic acid ethyl ester, 7a A suspension of zinc metal dust (24.2 g, 370 mmol) in THF (325 mL) under Argon at 5° C. was treated dropwise with titanium (IV) tetrachloride (20.3 mL, 180 mmol). The mixture was heated to reflux for 2 h. The mixture was allowed to cool to rt and a solution of 9-oxo-9H-xanthene-3-carboxylic acid diethylamide, 6a (13.69, 46 mmol) and N-carbethoxynortropinone (9.21 g, 46 mmol) in THF (100 mL) was added dropwise. The reaction was heated to reflux for another 2 h. The mixture was allowed to cool to rt and excess potassium carbonate in ice water was added. The mixture was extracted with ethyl acetate and the combined extracts were washed with brine, dried over magnesium sulfate, filtered and evaporated to give 22 g of a gum. This crude product was purified via flash chromatography over silica gel (eluent:1:1 EtOAc/hexanes) to yield 17 g (36.9 mmol) of title compound 3-(3-diethylcarbamoyl-xanthen-9-ylidene)-8-aza-bicyclo[3.2.1]octane-8-carboxylic acid ethyl ester, 7a. MS m/z (MH$^+$) 461.8.

Procedure 8

9-(8-Aza-bicyclo[3.2.1]oct-3-ylidene)-9H-xanthene-3-carboxylic acid diethylamide, 8a To a solution of 3-(3-diethylcarbamoyl-xanthen-9-ylidene)-8-aza-bicyclo[3.2.1]octane-8-carboxylic acid ethyl ester, 7a (16.0 g, 34.8 mmol) in acetic acid (35 mL) under Argon was added 30% HBr in acetic acid (100 mL). The mixture was heated on a steam bath for 1 h. The mixture was allowed to cool to rt, added to ice cold NaOH and extracted with methylene chloride. The organic layer was washed with brine and dried over potassium carbonate. Evaporation of the solvent provided 12 g of crude material which was purified by column chromatography (eluent: 7% 2 N NH$_3$ in methanol/ 93% CH$_2$Cl$_2$) to yield 7.66 g (19.7 mmol) of title compound 9-(8aza-bicyclo[3.2.1]oct-3-ylidene)-9H-xanthene-3-carboxylic acid diethylamide, 8a. MS m/z=389.3 (MH$^+$); $^1$H NMR 300 MHz (CDCl$_3$) δ 1.1-1.4 (m, 6H), 1.7 (m, 2H), 2.7-3.0 (m, 4H), 3.4 (br s, 4H), 3.5-3.7 (m, 4H), 7.0-7.3 (m, 7H).

Procedure 9

9-(8-Aza-bicyclo[3.2.1]oct-3-yl)-9H-xanthene-3-carboxylic acid diethylamide, 9a

To a solution of 9-(8-aza-bicyclo[3.2.1]oct-3-ylidene)-9H-xanthene-3-carboxylic acid diethylamide, 8a (3 g, 7.7 mmol) in chloroform (50 mL) were added ethanol (2.25 mL, 38.6 mmol) and trimethylsilyl iodide (5.25 mL, 38.6 mmol). The mixture was stirred at 100° C. for 2 h in a sealed tube. The reaction was allowed to cool to rt and washed with 1 N NaOH, aqueous Na$_2$S$_2$O$_4$, and brine. The organic phase was dried over sodium sulfate, filtered, and concentrated, to yield title compound 9-(8-aza-bicyclo[3.2.1]oct-3-yl)-9H-xanthene-3-carboxylic acid diethylamide, 9a (3.0 g, 0.53 mmol). MS m/z=391.4 (MH$^+$)

Procedure 10

9-(8-Furan-3-ylmethyl-8-aza-bicyclo[3.2.1]oct-3-ylidene)-9H-xanthene-3-carboxylic acid diethylamide, 10a To a solution of 9-(8-aza-bicyclo[3.2.1]oct-3-yl)-9H-xanthene-3-carboxylic acid diethylamide, 9a (0.65 g, 1.7 mmol) in CH$_2$Cl$_2$ (20 mL) were added tetramethylammonium triacetoxyborohydride (0.53 g, 2.5 mmol) and 3-furaldehyde (0.17 mL, 2.0 mmol). The mixture was stirred at rt for 24 h, diluted with CH$_2$Cl$_2$ (10 mL), and washed with 1 N NaOH. The organic phase was dried over sodium sulfate, filtered, and concentrated. The crude product was purified by flash chromatography (eluent: 5% 0.5 M NH$_3$ in methanol in CH$_2$Cl$_2$) to yield title compound 9-(8-furan-3-ylmethyl-8-aza-bicyclo [3.2.1]oct-3-ylidene)-9H-xanthene-3-carboxylic acid diethylamide, 10a (0.25 g, 0.53 mmol). MS m/z=471.2 (MH$^+$).

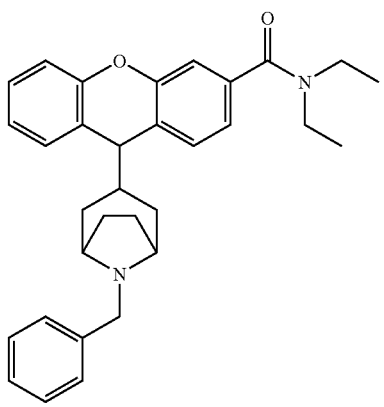

11a

9-(8-Benzyl-8-aza-bicyclo[3.2.1]oct-3-yl)-9H-xanthene-3-carboxylic acid diethylamide, 11a Using an adaptation of the method described in Procedure 10, substituting benzaldehyde for 3-furaldehyde, the title compound 9-(8-benzyl-8-aza-bicyclo[3.2.1]oct-3-yl)-9H-xanthene-3-carboxylic acid diethylamide, 11a was obtained as a TFA salt after purification via reverse phase HPLC (eluent: CH$_3$CN in H$_2$O containing 0.1% TFA). MS m/z (MH$^+$) 481.2.

9-(8-Furan-2-ylmethyl-8-aza-bicyclo[3.2.1]oct-3-yl)-9H-xanthene-3-carboxylic acid diethylamide, 13a Using an adaptation of the method described in Procedure 10, substituting 2-furaldehyde for 3-furaldehyde, the title compound 9-(8-furan-2-ylmethyl-8-aza-bicyclo[3.2.1]oct-3-yl)-9H-xanthene-3-carboxylic acid diethylamide, 13a was obtained as a TFA salt after purification via reverse phase HPLC (eluent: CH$_3$CN in H$_2$O containing 0.1% TFA). MS m/z (MH$^+$) 471.1.

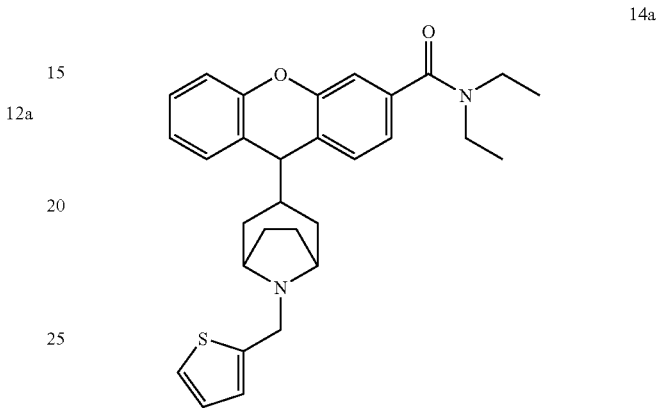

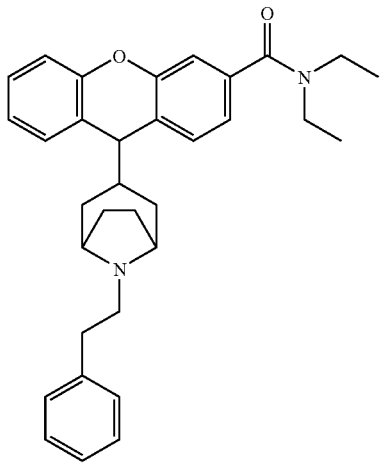

9-(8-Phenethyl-8-aza-bicyclo[3.2.1]oct-3-yl)-9H-xanthene-3-carboxylic acid diethylamide, 12a Using an adaptation of the method described in Procedure 10, substituting phenylacetaldehyde for 3-furaldehyde, the title compound 9-(8-phenethyl-8-aza-bicyclo[3.2.1]oct-3-yl)-9H-xanthene-3-carboxylic acid diethylamide, 12a was obtained as a TFA salt after purification via reverse phase HPLC (eluent: CH$_3$CN in H$_2$O containing 0.1% TFA). MS m/z (MH$^+$) 495.2.

9-(8-Thiophen-2-ylmethyl-8-aza-bicyclo[3.2.1]oct-3-yl)-9H-xanthene-3-carboxylic acid diethylamide, 14a Using an adaptation of the method described in Procedure 10, substituting 2-thiophene carboxaldehyde for 3-furaldehyde, the title compound 9-(8-thiophen-2-ylmethyl-8-aza-bicyclo[3.2.1]oct-3-yl)-9H-xanthene-3-carboxylic acid diethylamide, 14a was obtained as a TFA salt after purification via reverse phase HPLC (eluent: CH$_3$CN in H$_2$O containing 0.1% TFA). MS m/z (MH$^+$) 487.1.

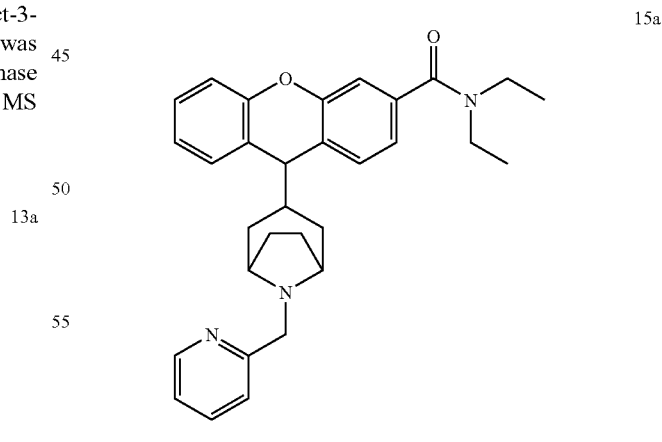

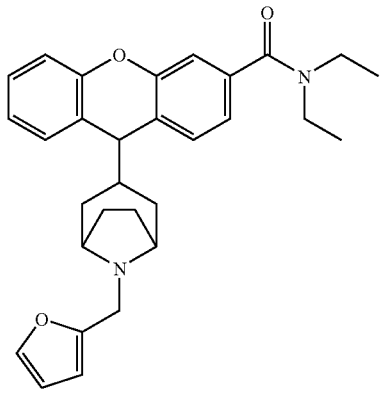

9-(8-Pyridin-2-ylmethyl-8-aza-bicyclo[3.2.1]oct-3-yl)-9H-xanthene-3-carboxylic acid diethylamide, 15a Using an adaptation of the method described in Procedure 10, substituting 2-pyridyl carboxaldehyde for 3-furaldehyde, the title compound 9-(8-pyridin-2-ylmethyl-8-aza-bicyclo

[3.2.1]oct-3-yl)-9H-xanthene-3-carboxylic acid diethylamide, 15a was obtained as a TFA salt after purification via reverse phase HPLC (eluent: CH$_3$CN in H$_2$O containing 0.1% TFA). MS m/z (MH$^+$) 482.2.

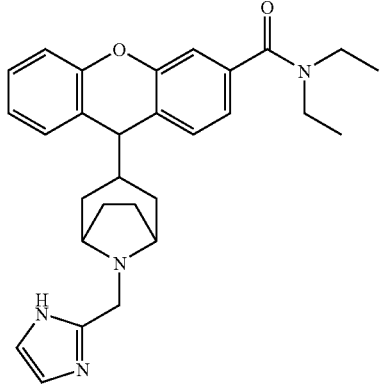

9-[8-(1H-Imidazol-2-ylmethyl)-8-aza-bicyclo[3.2.1]oct-3-yl]-9H-xanthene-3-carboxylic acid diethylamide, 16a Using an adaptation of the method described in Procedure 10, substituting 1H-imidazole-2-carboxaldehyde for 3-furaldehyde, the title compound 9-[8-(1H-imidazol-2-ylmethyl)-8-aza-bicyclo[3.2.1]oct-3-yl]-9H-xanthene-3-carboxylic acid diethylamide, 16a was obtained as a TFA salt after purification via reverse phase HPLC (eluent: CH$_3$CN in H$_2$O containing 0.1% TFA). MS m/z (MH$^+$) 471.1.

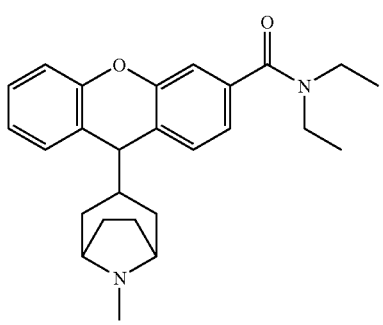

9-(8-Methyl-8-aza-bicyclo[3.2.1]oct-3-yl)-9H-xanthene-3-carboxylic acid diethylamide, 17a Using an adaptation of the method described in Procedure 10, substituting paraformaldehyde for 3-furaldehyde, the title compound 9-(8-methyl-8-aza-bicyclo[3.2.1]oct-3-yl)-9H-xanthene-3-carboxylic acid diethylamide, 17a was obtained as a TFA salt after purification via reverse phase HPLC (eluent: CH$_3$CN in H$_2$O containing 0.1% TFA). MS m/z (MH$^+$) 405.1.

Example B

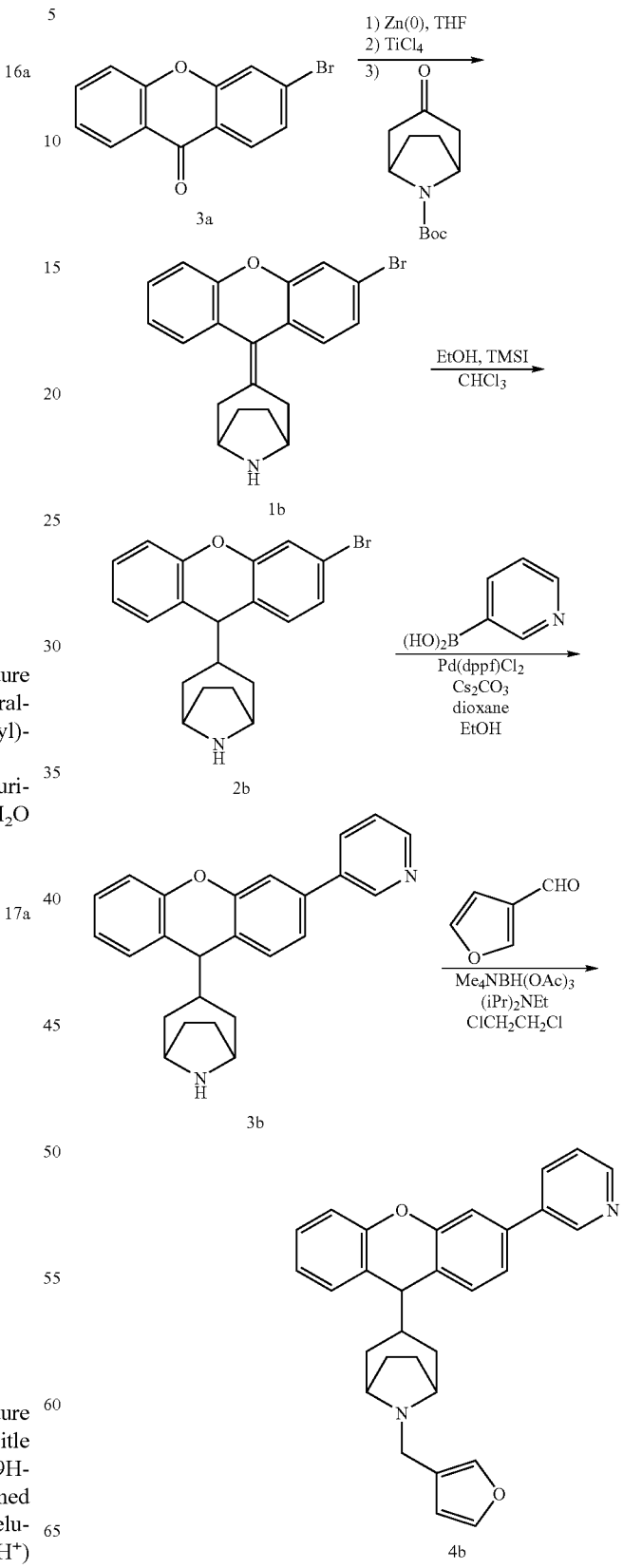

3-(3-Bromo-xanthen-9-ylidene)-8-aza-bicyclo[3.2.1]octane, 1b

Using an adaptation of the method described in Procedure 7, substituting 3-bromo-xanthen-9-one, 3a, for 9-oxo-9H-xanthene-3-carboxylic acid diethylamide, 6a (13.69, 46 mmol) and 3-oxo-8-aza-bicyclo[3.2.1]octane-8-carboxylic acid tert-butyl ester for N-carbethoxynortropinone, the title compound 3-(3-bromo-xanthen-9-ylidene)-8-aza-bicyclo[3.2.1]octane, 1b was obtained. MS m/z (MH$^+$) 368.0/370.0

3-(3-Bromo-9H-xanthen-9-yl)-8-aza-bicyclo[3.2.1]octane, 2b

Using an adaptation of the method described in Procedure 9, substituting 3-(3-bromo-xanthen-9-ylidene)-8-aza-bicyclo[3.2.1]octane, 1b for 9-(8-aza-bicyclo[3.2.1]oct-3-ylidene)-9H-xanthene-3-carboxylic acid diethylamide, 8a, the title compound 3-(3-bromo-9H-xanthen-9-yl)-8-aza-bicyclo[3.2.1]octane, 2b was obtained. MS m/z=370.0/372.0 (MH$^+$).

Procedure 11

3-(3-Pyridin-3-yl-9H-xanthen-9-yl)-8-aza-bicyclo[3.2.1]octane, 3b

To a solution of 3-(3-bromo-9H-xanthen-9-yl)-8-aza-bicyclo[3.2.1]octane, 2b (0.15 g, 0.405 mmol) in dioxane (2 mL) and ethanol (0.5 mL) were added 3-pyridylboronic acid (0.055 g, 0.446 mmol), 1,1'-bis-(diphenylphosphino)-ferrocene-palladium (II) dichloride (30 mg, 0.041 mmol), and cesium carbonate (0.277 g, 0.85 mmol), and the mixture was heated at 100°C for 2 h. The mixture was allowed to cool to rt and was filtered and concentrated. The residue was purified by reverse phase chromatography (eluent: CH$_3$CN in H$_2$O containing 0.1% TFA) to afford the title compound 3-(3-pyridin-3-yl-9H-xanthen-9-yl)-8-aza-bicyclo[3.2.1]octane, 3b as a TFA salt. MS m/z=369.5 (MH$^+$).

Procedure 12

8-Furan-3-ylmethyl-3-(3-pyridin-3-yl-9H-xanthen-9-yl)-8-aza-bicyclo[3.2.1]-octane, 4b To a solution of 3-(3-pyridin-3-yl-9H-xanthen-9-yl)-8-aza-bicyclo[3.2.1]octane, 3b (0.08 g, 0.134 mmol) in ClCH$_2$CH$_2$Cl (2 mL) was added tetramethyl-ammonium triacetoxyborohydride (0.053 g, 2.01 mmol) and 3-furaldehyde (0.17 mL, 2.0 mmol). The reaction was stirred at rt for 24 h. The reaction was diluted with CH$_2$Cl$_2$ (10 mL) and washed with 1 N NaOH. The organic phase was dried over sodium sulfate, filtered, and concentrated. The crude product was purified via reverse phase chromatography (eluent: CH$_3$CN in H$_2$O containing 0.1% TFA) to yield 0.045 g (75%) of title compound 8-furan-3-ylmethyl-3-(3-pyridin-3-yl-9H-xanthen-9-yl)-8-aza-bicyclo[3.2.1]-octane, 4b as a TFA salt. MS m/z=449.1 (MH$^+$).

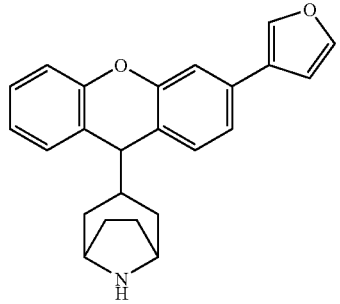

3-(3-Furan-3-yl-9H-xanthen-9-yl)-8-aza-bicyclo[3.2.1]octane, 5b

Using an adaptation of the method described in Procedure 11, substituting 3-furylboronic acid for 3-pyridylboronic acid, title compound 3-(3-furan-3-yl-9H-xanthen-9-yl)-8-aza-bicyclo[3.2.1]octane, 5b was obtained as a TFA salt. MS m/z (MH$^+$) 358. 1.

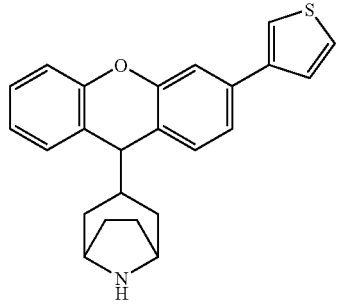

3-(3-Thiophen-3-yl-9H-xanthen-9-yl)-8-aza-bicyclo[3.2.1]octane, 6b

Using an adaptation of the method described in Procedure 11, substituting 3-thiopheneboronic acid for 3-pyridylboronic acid, title compound 3-(3-thiophen-3-yl-9H-xanthen-9-yl)-8-aza-bicyclo[3.2.1]octane, 6b was obtained as a TFA salt. MS m/z (MH$^+$) 374.0.

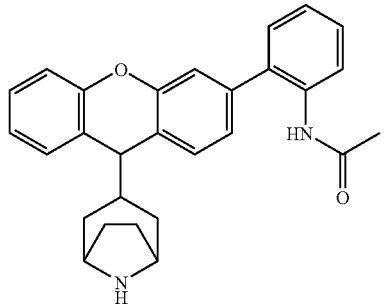

N-{2-[9-(8-Aza-bicyclo[3.2.1]oct-3-yl)-9H-xanthen-3-yl]-phenyl}-acetamide, 7b

Using an adaptation of the method described in Procedure 11, substituting 2-acetylaminophenylboronic acid for 3-pyridylboronic acid, title compound N-{2-[9-(8-aza-bicyclo[3.2.1]oct-3-yl)-9H-xanthen-3-yl]-phenyl}-acetamide, 7b was obtained as a TFA salt. MS m/z (MH+) 425.1.

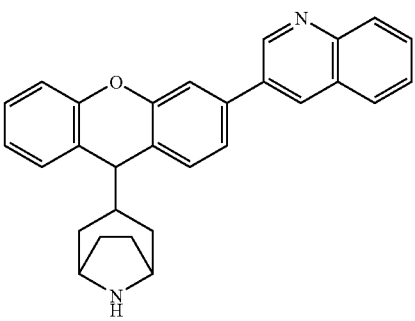

3-[9-(8-Aza-bicyclo[3.2.1]oct-3-yl)-9H-xanthen-3-yl]-quinoline, 8b

Using an adaptation of the method described in Procedure 11, substituting 3-quinolylboronic acid for 3-pyridylboronic acid, title compound 3-[9-(8-aza-bicyclo[3.2.1]oct-3-yl)-9H-xanthen-3-yl]-quinoline, 8b was obtained as a TFA salt. MS m/z(MH+)419.1.

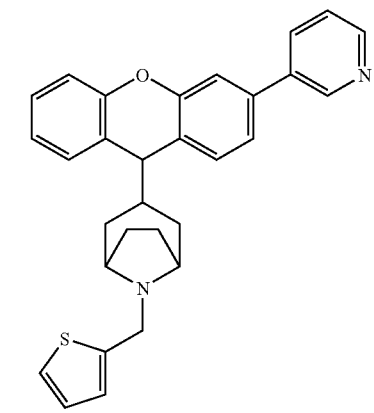

3-(3-Pyridin-3-yl-9H-xanthen-9-yl)-8-thiophen-2-ylmethyl-8-aza-bicyclo[3.2.1]octane, 9b Using an adaptation of the method described in Procedure 12, substituting 2-thiophenecarboxaldehyde for 3-furaldehyde, title compound 3-(3-pyridin-3-yl-9H-xanthen-9-yl)-8-thiophen-2-ylmethyl-8-aza-bicyclo[3.2.1]octane, 9b was obtained as a TFA salt. MS m/z (MH+) 449.1.

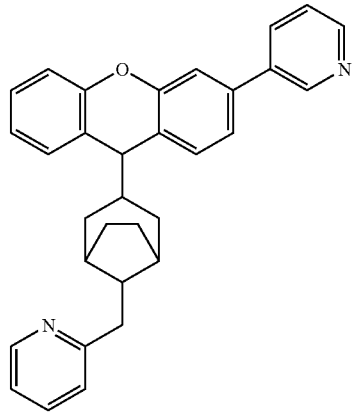

8-Pyridin-2-ylmethyl-3-(3-pyridin-3-yl-9H-xanthen-9-yl)-8-aza-bicyclo[3.2.1]octane, 10b Using an adaptation of the method described in Procedure 12, substituting 2-pyridylcarboxaldehyde for 3-furaldehyde, title compound 8-pyridin-2-ylmethyl-3-(3-pyridin-3-yl-9H-xanthen-9-yl)-8-aza-bicyclo[3.2.1]octane, 10b was obtained as a TFA salt. MS m/z (MH+) 464.9.

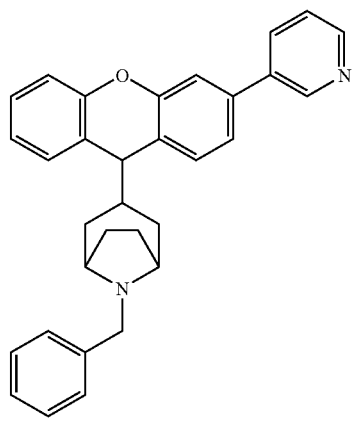

8-Benzyl-3-(3-pyridin-3-yl-9H-xanthen-9-yl)-8-aza-bicyclo[3.2.1]octane, 11b

Using an adaptation of the method described in Procedure 12, substituting benzaldehyde for 3-furaldehyde, title compound 8-benzyl-3-(3-pyridin-3-yl-9H-xanthen-9-yl)-8-aza-bicyclo[3.2.1]octane, 11b was obtained as a TFA salt. MS m/z (MH+) 459.0.

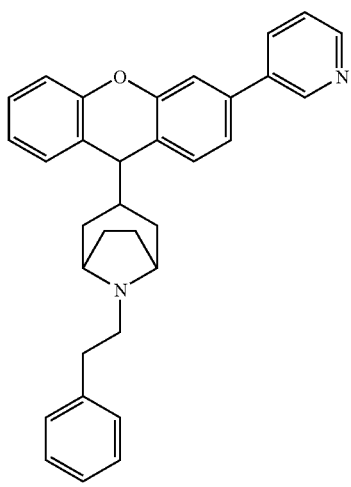

8-Phenethyl-3-(3-pyridin-3-yl-9H-xanthen-9-yl)-8-aza-bicyclo[3.2.1]octane, 12b

Using an adaptation of the method described in Procedure 12, substituting phenylacetaldehyde for 3-furaldehyde, title compound 8-phenethyl-3-(3-pyridin-3-yl-9H-xanthen-9-yl)-8-aza-bicyclo[3.2.1]octane, 12b was obtained as a TFA salt. MS m/z (MH$^+$) 473.0.

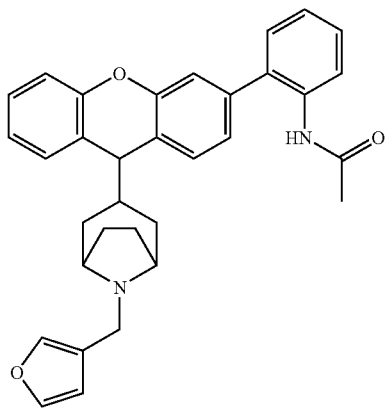

N-{2-[9-(8-Furan-3-yl methyl-8-aza-bicyclo[3.2.1]oct-3-yl)-9H-xanthen-3-yl]-phenyl}-acetamide, 13b Using an adaptation of the method described in Procedure 12, substituting N-{2-[9-(8-aza-bicyclo[3.2.1]oct-3-yl)-9H-xanthen-3-yl]-phenyl}-acetamide, 7b for 3-(3-pyridin-3-yl-9H-xanthen-9-yl)-8-aza-bicyclo[3.2.1]octane, 3b, title compound N-{2-[9-(8-furan-2-ylmethyl-8-aza-bicyclo[3.2.1]oct-3-yl)-9H-xanthen-3-yl]-phenyl}-acetamide, 13b was obtained as a TFA salt. MS m/z (MH$^+$) 505.2.

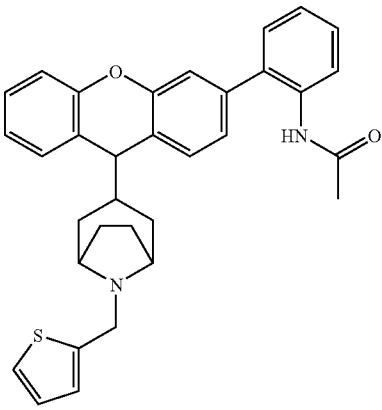

N-{2-[9-(8-Thiophen-2-ylmethyl-8-aza-bicyclo[3.2.1]oct-3-yl)-9H-xanthen-3-yl]-phenyl}-acetamide, 14b Using an adaptation of the method described in Procedure 12, substituting N-{2-[9-(8-aza-bicyclo[3.2.1]oct-3-yl)-9H-xanthen-3-yl]-phenyl}-acetamide, 7b for 3-(3-pyridin-3-yl-9H-xanthen-9-yl)-8-aza-bicyclo[3.2.1]octane, 3b and 2-thiophenecarboxaldehyde for 3-furaldehyde, title compound N-{2-[9-(8-thiophen-2-ylmethyl-8-aza-bicyclo[3.2.1]oct-3-yl)-9H-xanthen-3-yl]-phenyl}-acetamide, 14b was obtained as a TFA salt. MS m/z (MH$^+$) 521.3.

N-{2-[9-(8-Pyridin-2-ylmethyl-8-aza-bicyclo[3.2.1]oct-3-yl)-9H-xanthen-3-yl]-phenyl}-acetamide, 15b Using an adaptation of the method described in Procedure 12, substituting N-{2-[9-(8-aza-bicyclo[3.2.1]oct-3-yl)-9H-xanthen-3-yl]-phenyl}-acetamide, 7b for 3-(3-pyridin-3-yl-9H-xanthen-9-yl)-8-aza-bicyclo[3.2.1]octane, 3b and 2-pyridylcarboxaldehyde for 3-furaldehyde, title compound N-{2-[9-(8-pyridin-2-ylmethyl-8-aza-bicyclo[3.2.1]oct-3-yl)-9H-xanthen-3-yl]-phenyl}-acetamide, 15b was obtained as a TFA salt. MS m/z (MH$^+$) 516.2.

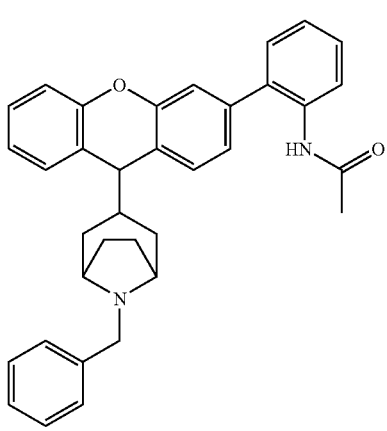

16b

N-{2-[9-(8-Benzyl-8-aza-bicyclo[3.2.1]oct-3-yl)-9H-xanthen-3-yl]-phenyl}-acetamide, 16b Using an adaptation of the method described in Procedure 12, substituting N-{2-[9-(8-aza-bicyclo[3.2.1]oct-3-yl)-9H-xanthen-3-yl]-phenyl}-acetamide, 7b for 3-(3-pyridin-3-yl-9H-xanthen-9-yl)-8-aza-bicyclo[3.2.1]octane, 3b and benzaldehyde for 3-furaldehyde, title compound N-{2-[9-(8-benzyl-8-aza-bicyclo[3.2.1]oct-3-yl)-9H-xanthen-3-yl]-phenyl}-acetamide, 16b was obtained as a TFA salt. MS m/z (MH$^+$) 515.0.

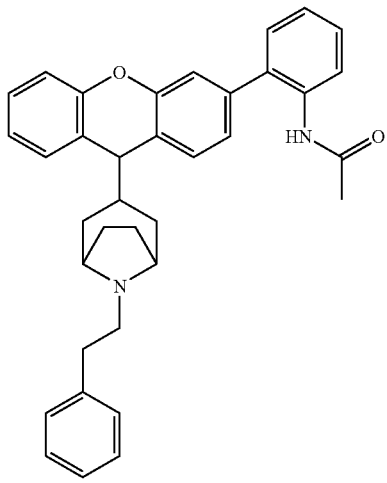

17b

N-{2-[9-(8-Phenethyl-8-aza-bicyclo[3.2.1]oct-3-yl)-9H-xanthen-3-yl]-phenyl}-acetamide, 17b Using an adaptation of the method described in Procedure 12, substituting N-{2-[9-(8-aza-bicyclo[3.2.1]oct-3-yl)-9H-xanthen-3-yl]-phenyl}-acetamide, 7b for 3-(3-pyridin-3-yl-9H-xanthen-9-yl)-8-aza-bicyclo[3.2.1]octane, 3b and phenylacetaldehyde for 3-furaldehyde, title compound N-{2-[9-(8-phenethyl-8-aza-bicyclo[3.2.1]oct-3-yl)-9H-xanthen-3-yl]-phenyl}-acetamide, 17b was obtained as a TFA salt. MS m/z (MH$^+$) 529.2.

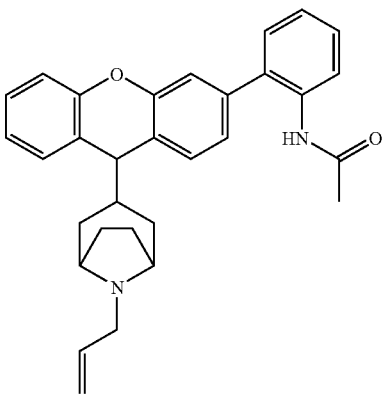

18b

Procedure 13

N-{2-[9-(8-Allyl-8-aza-bicyclo[3.2.1]oct-3-yl)-9H-xanthen-3-yl]-phenyl}-acetamide, 18b To a solution of N-{2-[9-(8-Aza-bicyclo[3.2.1]oct-3-yl)-9H-xanthen-3-yl]-phenyl}-acetamide, 7b (53 mg, 0.125 mmol) in DMF (0.5 mL) at 0° C. were added potassium carbonate (18 mg, 0.13 mmol) and allyl bromide (10.6 µL, 0.122 mmol). The mixture was stirred overnight at rt, and poured onto H$_2$O. The solid was separated via filtration and washed with H$_2$O. The solid was purified via reverse phase HPLC (eleuent gradient: 10% to 90% CH$_3$CN in H$_2$O containing 0.1% TFA) to yield 25 mg (36%) of N-{2-[9-(8-allyl-8-aza-bicyclo[3.2.1]oct-3-yl)-9H-xanthen-3-yl]-phenyl}-acetamide, 18b. MS 18b: m/z: 464.9 (MH$^+$).

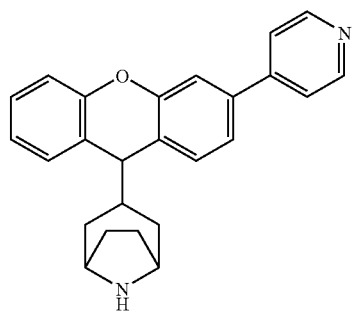

20b 3-(3-Pyridin-4-yl-9H-xanthen-9-yl)-8-aza-bicyclo[3.2.1]octane, 20b

Using an adaptation of the method described in Procedure 11, substituting 4-pyridylboronic acid for 3-pyridylboronic acid, title compound 3-(3-pyridin-4-yl-9H-xanthen-9-yl)-8-aza-bicyclo[3.2.1]octane, 20b was obtained as a TFA salt. MS m/z (MH$^+$) 369.1.

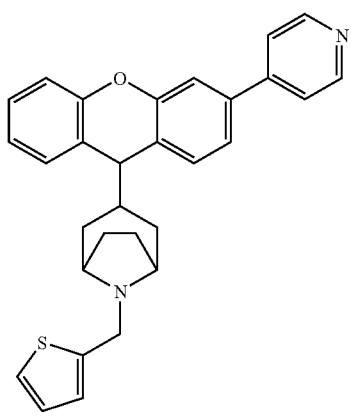

3-(3-Pyridin-4-yl-9H-xanthen-9-yl)-8-thiophen-2-ylmethyl-8-aza-bicyclo[3.2.1]octane, 21b

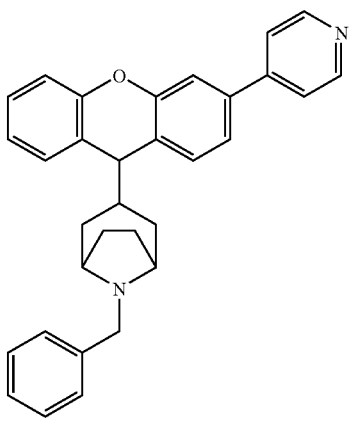

8-Benzyl-3-(3-pyridin-4-yl-9H-xanthen-9-yl)-8-aza-bicyclo[3.2.1]octane, 23b

Using an adaptation of the method described in Procedure 12, substituting the TFA salt of 3-(3-pyridin-4-yl-9H-xanthen-9-yl)-8-aza-bicyclo[3.2.1]octane, 20b for 3-(3-pyridin-3-yl-9H-xanthen-9-yl)-8-aza-bicyclo[3.2.1]octane, 3b and 2-thiophenecarboxaldehyde for 3-furaldehyde, title compound 3-(3-pyridin-4-yl-9H-xanthen-9-yl)-8-thiophen-2-ylmethyl-8-aza-bicyclo[3.2.1]octane, 21b was obtained as a TFA salt. MS m/z (MH$^+$) 464.9.

Using an adaptation of the method described in Procedure 12, substituting the TFA salt of 3-(3-pyridin-4-yl-9H-xanthen-9-yl)-8-aza-bicyclo[3.2.1]octane, 20b for 3-(3-pyridin-3-yl-9H-xanthen-9-yl)-8-aza-bicyclo[3.2.1]octane, 3b and benzaldehyde for 3-furaldehyde, title compound 8-benzyl-3-(3-pyridin-4-yl-9H-xanthen-9-yl)-8-aza-bicyclo[3.2.1]octane, 23b was obtained as a TFA salt. MS m/z (MH$^+$) 458.9.

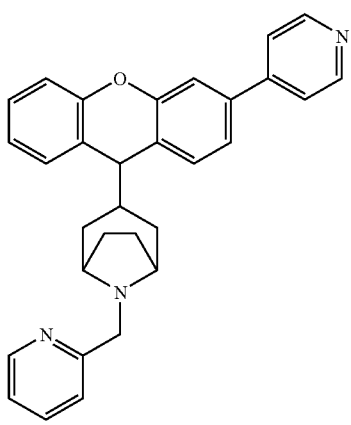

8-Pyridin-2-ylmethyl-3-(3-pyridin-4-yl-9H-xanthen-9-yl)-8-aza-bicyclo[3.2.1]octane, 22b

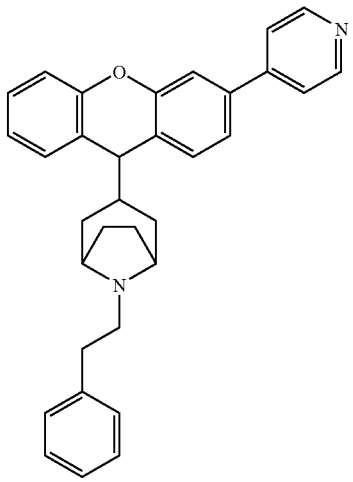

8-Phenethyl-3-(3-pyridin-4-yl-9H-xanthen-9-yl)-8-aza-bicyclo[3.2.1]octane, 24b

Using an adaptation of the method described in Procedure 12, substituting the TFA salt of 3-(3-pyridin-4-yl-9H-xanthen-9-yl)-8-aza-bicyclo[3.2.1]octane, 20b for 3-(3-pyridin-3-yl-9H-xanthen-9-yl)-8-aza-bicyclo[3.2.1]octane, 3b and 2-pyridylcarboxaldehyde for 3-furaldehyde, title compound 8-pyridin-2-ylmethyl-3-(3-pyridin-4-yl-9H-xanthen-9-yl)-8-aza-bicyclo[3.2.1]octane, 22b was obtained as a TFA salt. MS m/z (MH$^+$) 459.9.

Using an adaptation of the method described in Procedure 12, substituting the TFA salt of 3-(3-pyridin-4-yl-9H-xanthen-9-yl)-8-aza-bicyclo[3.2.1]octane, 20b for 3-(3-pyridin-3-yl-9H-xanthen-9-yl)-8-aza-bicyclo[3.2.1]octane, 3b and phenylacetaldehyde for 3-furaldehyde, title compound 8-phenethyl-3-(3-pyridin-4-yl-9H-xanthen-9-yl)-8-aza-bicyclo[3.2.1]octane, 24b was obtained as a TFA salt. MS m/z (MH$^+$) 473.0.

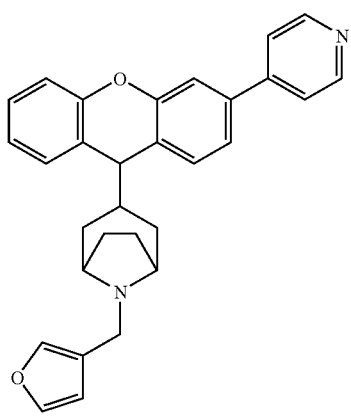

8-Furan-3-ylmethyl-3-(3-pyridin-4-yl-9H-xanthen-9-yl)-8-aza-bicyclo[3.2.1]octane, 25b Using an adaptation of the method described in Procedure 12, substituting the TFA salt of 3-(3-pyridin-4-yl-9H-xanthen-9-yl)-8-aza-bicyclo[3.2.1]octane, 20b for 3-(3-pyridin-3-yl-9H-xanthen-9-yl)-8-aza-bicyclo[3.2.1]octane, 3b, title compound 8-furan-3-ylmethyl-3-(3-pyridin-4-yl-9H-xanthen-9-yl)-8-aza-bicyclo[3.2.1]octane, 25b was obtained as a TFA salt. MS m/z (MH$^+$) 449.1.

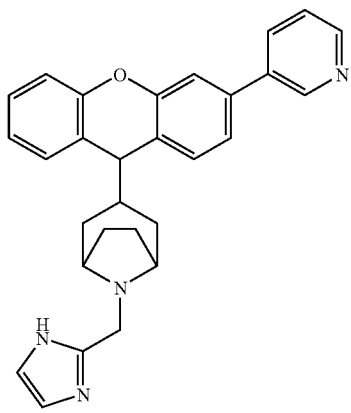

8-(1H-Imidazol-2-ylmethyl)-3-(3-pyridin-3-yl-9H-xanthen-9-yl)-8-aza-bicyclo[3.2.1]octane, 26b Using an adaptation of the method described in Procedure 12, substituting 1H-imidazole-2-carboxaldehyde for 3-furaldehyde, title compound 8-(1H-imidazol-2-ylmethyl)-3-(3-pyridin-3-yl-9H-xanthen-9-yl)-8-aza-bicyclo[3.2.1]octane, 26b was obtained as a TFA salt. MS m/z (MH$^+$) 449.0.

Example C

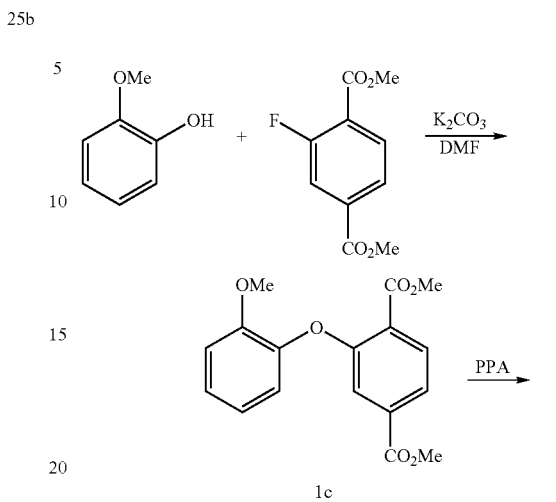

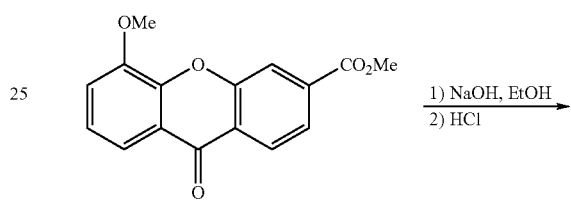

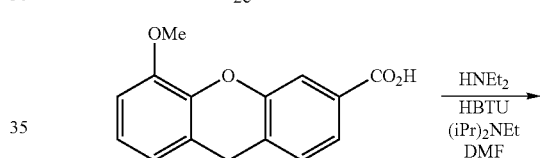

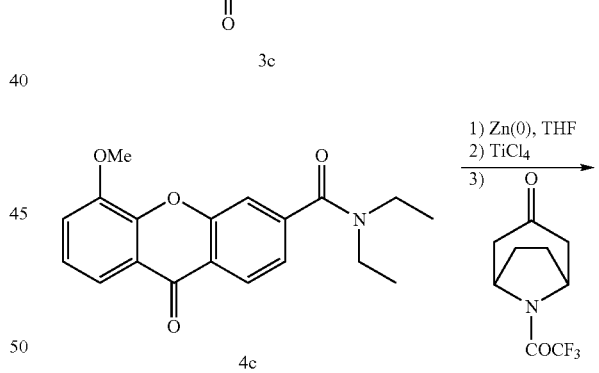

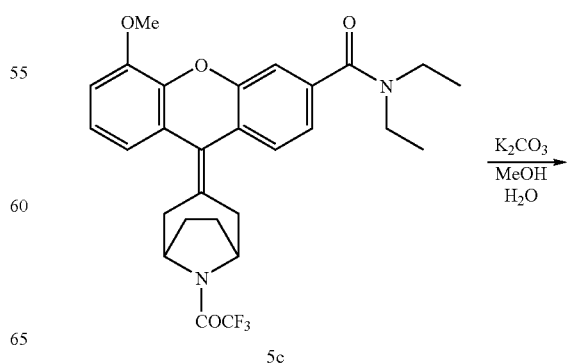

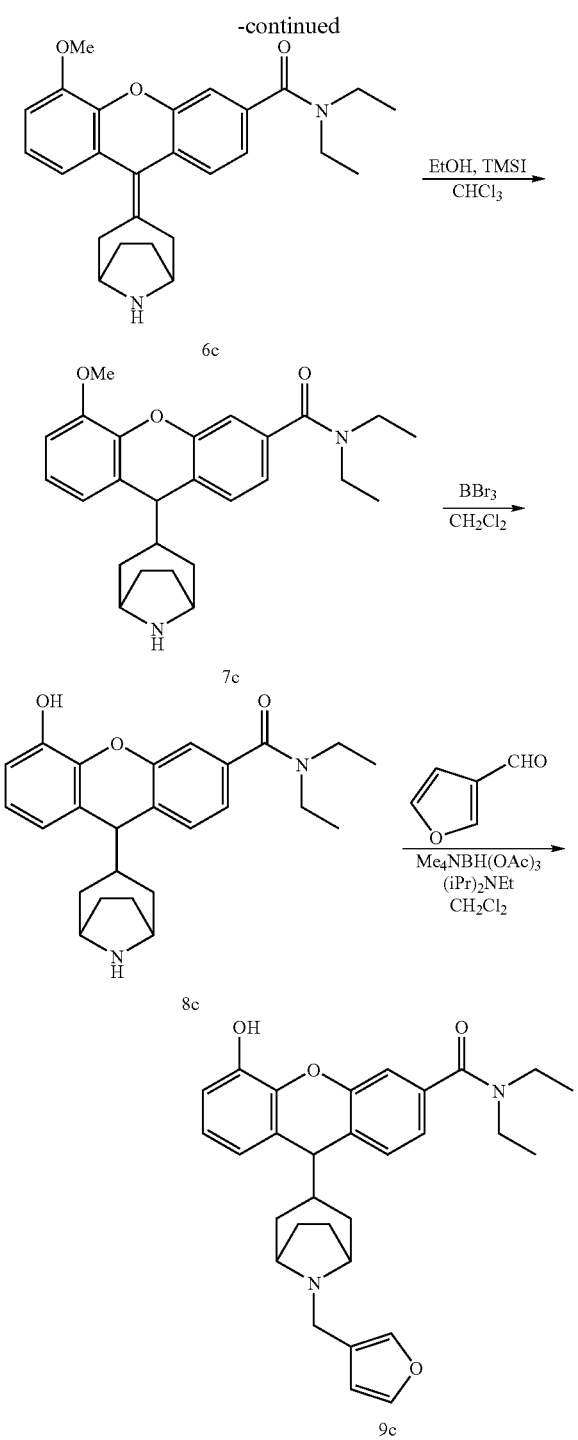

Procedure 14

2-(2-Methoxyphenoxy)-terephthalic acid dimethyl ester, 1c

A mixture of 2-methoxyphenol (5.7 mL, 51.8 mmol) and potassium carbonate (7.16 g, 51.8 mmol) in dimethylformamide (100 mL) was stirred at rt for 15 min. Dimethyl 2-fluoroterephthalate (10 g, 47.1 mmol) was added, and the, mixture was heated at 100° C. for 30 h. The reaction mixture was allowed to cool to rt and poured into ice water (300 mL). The mixture was stirred until the desired material precipitated. The solid was separated by filtration and washed with $H_2O$. After air-drying, 12.75 g (40.3 mmol) of title compound 2-(2-methoxy-phenoxy)-terephthalic acid dimethyl ester, 1c was obtained. MS m/z=449.1 ($MH^+$)

Procedure 15

5-Methoxy-9-oxo-9H-xanthene-3-carboxylic acid methyl ester, 2c 2-(2-Methoxyphenoxy)-terephthalic acid dimethyl ester, 1c (12.75 g, 40.3 mmol) was added in portions to polyphosphoric acid (280 g) and the mixture was heated to 125° C. for 2 h. The mixture was poured into ice water (500 mL) and stirred overnight. A gummy solid was separated, washed with $H_2O$, and dissolved in methanol. The methanol was evaporated, and the residual solid was triturated with diethyl ether, yielding 10.3 g (89.9%) of 5-methoxy-9-oxo-9H-xanthene-3-carboxylic acid methyl ester, 2c. MS m/z=284.9 ($MH^+$).

5-Methoxy-9-oxo-9H-xanthene-3-carboxylic acid, 3c

Using an adaptation of the method described in Procedure 5, substituting 5-methoxy-9-oxo-9H-xanthene-3-carboxylic acid methyl ester, 2c for 9-oxo-9H-xanthene-3-carboxylic acid methyl ester, 4a, title compound 5-methoxy-9-oxo-9H-xanthene-3-carboxylic acid, 3c was obtained. MS m/z ($MH^+$) 271.0.

Procedure 16

5-Methoxy-9-oxo-9H-xanthene-3-carboxylic acid diethylamide, 4c

To a solution of 5-methoxy-9-oxo-9H-xanthene-3-carboxylic acid, 3c (6.8 g, 25.2 mmol) in DMF (70 mL), were added HBTU (10 g, 26.4 mmol) and N,N-diisopropyl-N-ethylamine (5.27 mL, 30.2 mmol). The mixture was stirred for 15 min at rt. N,N-Diethylamine (3.12 mL, 30.2 mmol) was added, and the mixture was stirred for 4 h at rt. The mixture was poured into ice-water (300 mL), and a solid precipitated. The solid was separated via filtration, washed with $H_2O$, and air-dried. The solid was purified via flash column chromatography (eluent gradient: 1% MeOH in $CH_2Cl_2$ to 5% MeOH in $CH_2Cl_2$) to yield 7.93 g (96.7%) of title compound 5-methoxy-9-oxo-9H-xanthene-3-carboxylic acid diethylamide, 4c. MS m/z=326.0 ($MH^+$).

5-Methoxy-9-[8-(2,2,2-trifluoro-acetyl)-8-aza-bicyclo[3.2.1]oct-3-ylidene]-9H-xanthene-3-carboxylic acid diethylamide, 5c Following Procedure 7, substituting 5-methoxy-9-oxo-9H-xanthene-3-carboxylic acid diethylamide, 4c for 9-oxo-9H-xanthene-3-carboxylic acid diethylamide, 6a and N-trifluoroacetylnortropinone for N-carbethoxynortropinone, title compound 5-methoxy-9-[8-(2,2,2-trifluoro-acetyl)-8-azabicyclo[3.2.1]oct-3-ylidene]-9H-xanthene-3-carboxylic acid diethylamide, 5c was obtained. MS m/z=514.8 ($MH^+$)

Procedure 17

9-(8-Aza-bicyclo[3.2.1]oct-3-ylidene)-5-methoxy-9H-xanthene-3-carboxylic acid diethylamide, 6c A mixture of 5-methoxy-9-[8-(2,2,2-trifluoro-acetyl)-8-aza-bicyclo[3.2.1]-oct-3ylidene]-9H-xanthene-3-carboxylic acid diethylamide, 5c (3.2g, 6.22 mmol) and potassium carbonate (1.89 g, 13.7 mmol) in methanol (50 mL) was stirred at rt overnight. The mixture was evaporated, and partitioned between methylene chloride (100 mL) and water (100 mL). The organic layer was separated, dried over sodium sulfate, filtered, and evaporated, yielding 2.72 g of 9-(8-aza-bicyclo[3.2.1]oct-3-ylidene)-5-methoxy-9H-xanthene-3-carboxylic acid diethylamide, 6c. MS m/z=419.0 (MH+).

9-(8-Aza-bicyclo[3.2.1]oct-3-yl)-5-methoxy-9H-xanthene-3-carboxylic acid diethylamide, 7c Using an adaptation of the method described in Procedure 9, substituting 9-(8-aza-bicyclo[3.2.1]oct-3-ylidene)-5-methoxy-9H-xanthene-3-carboxylic acid diethylamide, 6c for 9-(8-aza-bicyclo[3.2.1]oct-3-ylidene)-9H-xanthene-3-carboxylic acid diethylamide, 8a, title compound 9-(8-aza-bicyclo[3.2.1]oct-3-yl)-5-methoxy-9H-xanthene-3-carboxylic acid diethylamide, 7c was obtained. MS m/z=421.4 (MH$^+$)

Procedure 18

9-(8-Aza-bicyclo[3.2.1]oct-3-yl)-5-hydroxy-9H-xanthene-3-carboxylic acid diethylamide, 8c To a solution of 9-(8-aza-bicyclo[3.2.1]oct-3-yl)-5-methoxy-9H-xanthene-3-carboxylic acid diethylamide, 7c (0.159 g, 0.38 mmol) in methylene chloride (4 mL) at rt was added a 1M solution of boron tribromide in methylene chloride (1.52 mL, 1.52 mmol) and the mixture was stirred at rt for 30 min. The mixture was cooled in an ice-water bath, and a solution of concentrated ammonia in methanol (3 mL conc NH$_4$OH in 30 ml MeOH) was added. The mixture was evaporated, dissolved in a methylene chloride and washed with water and brine. The organic phase was dried over Na$_2$SO$_4$, filtered, and evaporated. Reverse phase HPLC purification (eluent: CH$_3$CN in H$_2$O containing 0.1% TFA) yielded 9-(8-aza-bicyclo[3.2.1]oct-3-yl)-5-hydroxy-9H-xanthene-3-carboxylic acid diethylamide, 8c as a TFA salt. MS m/z=405.0 (MH$^+$).

9-(8-Furan-3-ylmethyl-8-aza-bicyclo[3.2.1]oct-3-yl)-5-hydroxy-9H-xanthene-3-carboxylic acid diethylamide, 9c Using an adaptation of the method described in Procedure 10, substituting 9-(8-aza-bicyclo[3.2.1]oct-3-yl)-5-hydroxy-9H-xanthene-3-carboxylic acid diethylamide, 8c for 9-(8-aza-bicyclo[3.2.1]oct-3-yl)-9H-xanthene-3-carboxylic acid diethylamide, 9a, the title compound 9-(8-furan-3-ylmethyl-8-aza-bicyclo[3.2.1]oct-3-yl)-5-hydroxy-9H-xanthene-3-carboxylic acid diethylamide, 9c was obtained as a TFA salt after reverse phase HPLC purification (eluent: CH$_3$CN in H$_2$O containing 0.1% TFA). MS m/z=487.1 (MH$^+$)

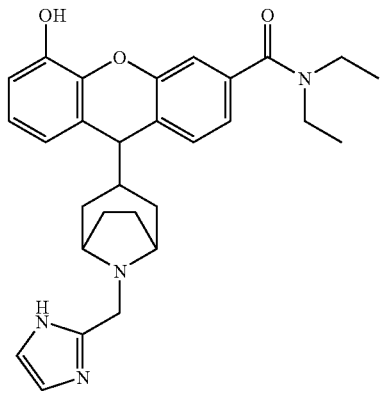

5-Hydroxy-9-[8-(1H-imidazol-2-ylmethyl)-8-aza-bicyclo[3.2.1]oct-3-yl]-9H-xanthene-3-carboxylic acid diethylamide, 10c Using an adaptation of the method described in Procedure 10, substituting 9-(8-aza-bicyclo[3.2.1]oct-3-yl )-5-hydroxy-9H-xanthene-3-carboxylic acid diethylamide, 8c for 9-(8-aza-bicyclo[3.2.1]oct-3-yl)-9H-xanthene-3-carboxylic acid diethylamide, 9a, and 1H-imidazole-2-carboxaldehyde for 3-furaldehyde the title compound 5-hydroxy-9-[8-(1H-imidazol-2-ylmethyl)-8-aza-bicyclo[3.2.1]oct-3-yl]-9H-xanthene-3-carboxylic acid diethylamide, 10c was obtained as a TFA salt after reverse phase HPLC purification (eluent: CH$_3$CN in H$_2$O containing 0.1% TFA). MS m/z (MH$^+$) 487.1.

Example D

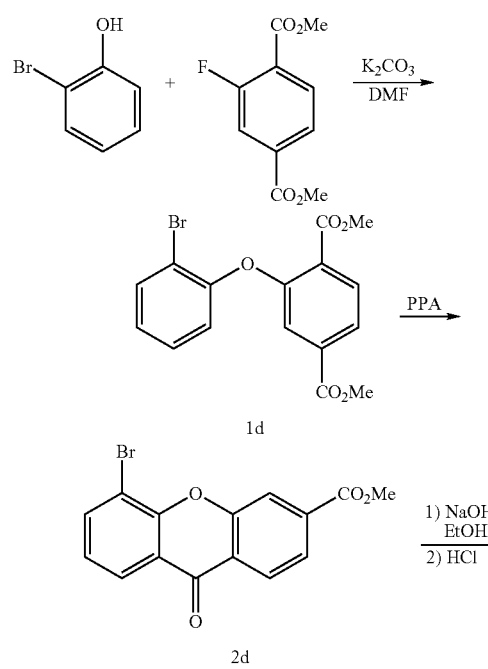

63

-continued

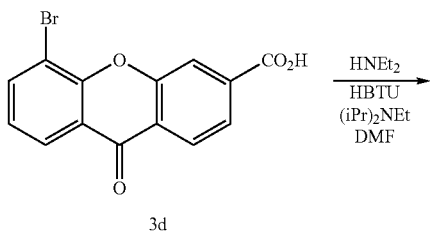

3d

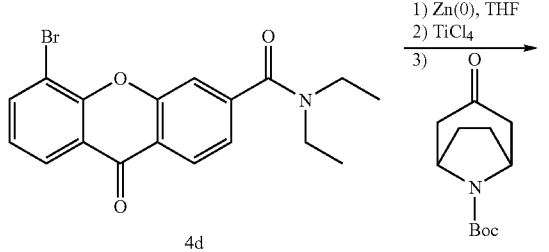

4d

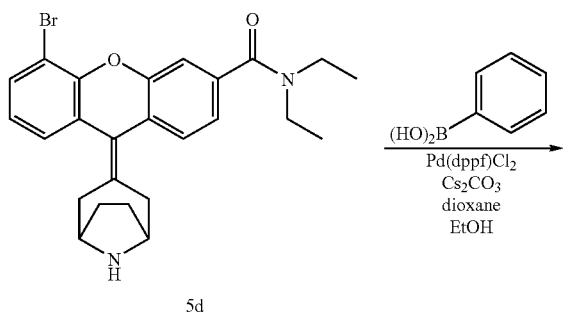

5d

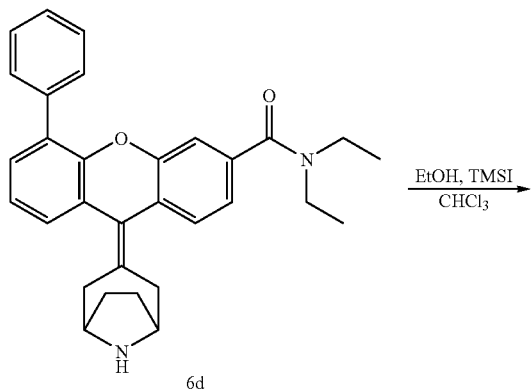

6d

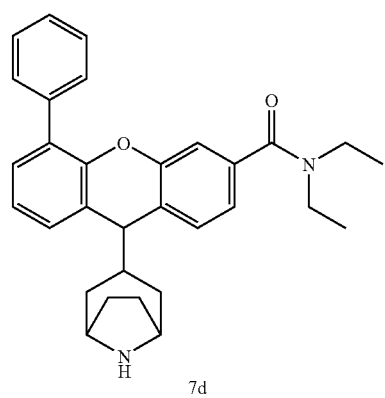

7d

64

2-(2-Bromophenoxy)-terephthalic acid dimethyl ester, 1d

Using an adaptation of the method described in Procedure 14, substituting 2-bromophenol for 2-methoxyphenol, the title compound 2-(2-bromophenoxy)-terephthalic acid dimethyl ester, 1d was obtained. MS m/z (MH$^+$) 364.6/366.7.

5-Bromo-9-oxo-9H-xanthene-3-carboxylic acid methyl ester, 2d

Using an adaptation of the method described in Procedure 15, substituting 2-(2-bromophenoxy)-terephthalic acid dimethyl ester, 1d for 2-(2-methoxy-phenoxy)-terephthalic acid dimethyl ester, 1c, title compound 5-bromo-9-oxo-9H-xanthene-3-carboxylic acid methyl ester, 2d was obtained

5-Bromo-9-oxo-9H-xanthene-3-carboxylic acid, 3d

Using an adaptation of the method described in Procedure 5, substituting 5-bromo-9-oxo-9H-xanthene-3-carboxylic acid methyl ester, 2d for 9-oxo-9H-xanthene-3-carboxylic acid methyl ester, 4a, title compound 5-bromo-9-oxo-9H-xanthene-3-carboxylic acid, 3d was obtained

5-Bromo-9-oxo-9H-xanthene-3-carboxylic acid diethylamide, 4d

Using an adaptation of the method described in Procedure 16, substituting 5-bromo-9-oxo-9H-xanthene-3-carboxylic acid, 3d for 5-methoxy-9-oxo-9H-xanthene-3-carboxylic acid, 3c, title compound 5-bromo-9-oxo&9H-xanthene-3-carboxylic acid diethylamide, 4d was obtained. MS m/z (MH$^+$) 374/375.8.

9-(8-Aza-bicyclo[3.2.1]oct-3-ylidene)-5-bromo-9H-xanthene-3-carboxylic acid diethylamide, 5d Using an adaptation of the method described in Procedure 7, substituting 5-bromo-9-oxo-9H-xanthene-3-carboxylic acid diethylamide, 4d for 9-oxo-9H-xanthene-3-carboxylic acid diethylamide, 6a, and 3-oxo-8-aza-bicyclo[3.2.1]-octane-8-carboxylic acid tert-butyl ester for N-carbethoxynortropinone, title compound 9-(8-aza-bicyclo[3.2.1]oct-3-ylidene)-5-bromo-9H-xanthene-3-carboxylic acid diethylamide, 5d was obtained. MS m/z (MH$^+$) 467/468.9.

9-(8-Aza-bicyclo[3.2.1]oct-3-ylidene)-5-phenyl-9H-xanthene-3-carboxylic acid diethylamide, 6d Using an adaptation of the method described in Procedure 11, substituting 9-(8-aza-bicyclo[3.2.1]oct-3-ylidene)-5-bromo-9H-xanthene-3-carboxylic acid diethylamide, 5d for 3-(3-bromo-9H-xanthen-9-yl)-8-aza-bicyclo[3.2.1]octane, 1b, and phenylboronic acid for 3-pyridylboronic acid, title compound 9-(8-aza-bicyclo[3.2.1]oct-3-ylidene)-5-phenyl-9H-xanthene-3-carboxylic acid diethylamide, 6d was obtained as a TFA salt after reverse phase HPLC purification (eluent: CH$_3$CN in H$_2$O containing 0.1% TFA). MS m/z (MH$^+$) 465.3.

9-(8-Aza-bicyclo[3.2.1]oct-3-yl)-5-phenyl-9H-xanthene-3-carboxylic acid diethylamide, 7d Using an adaptation of the method described in Procedure 9, substituting 9-(8-aza-bicyclo[3.2.1]oct-3-ylidene)-5-phenyl-9H-xanthene-3-carboxylic acid diethylamide, 6d for 9-(8-aza-bicyclo[3.2.1]oct-3-ylidene)-9H-xanthene-3-carboxylic acid diethylamide, 8a, title compound 9-(8-aza-bicyclo[3.2.1]oct-3-yl)-5-phenyl-9H-xanthene-3-carboxylic acid diethylamide, 7d was obtained as a TFA salt after reverse phase HPLC purification (eluent: CH₃CN in H₂O containing 0.1% TFA). MS m/z (MH⁺) 467.1.

Example E

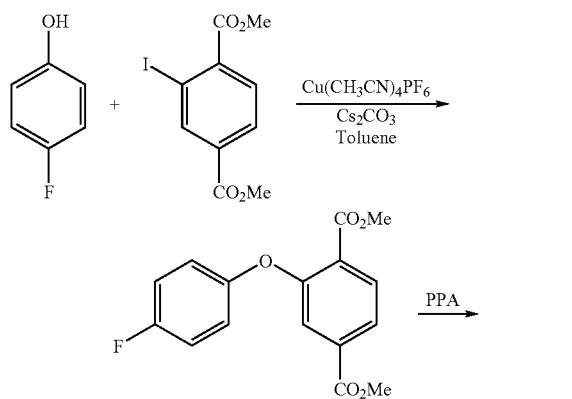

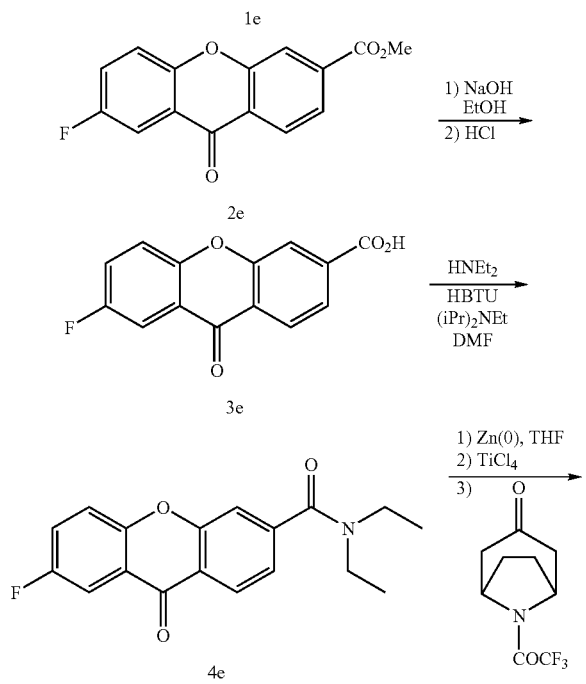

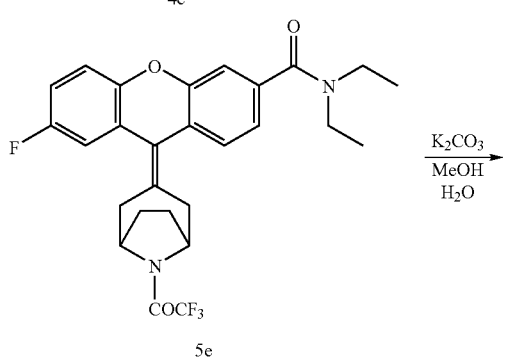

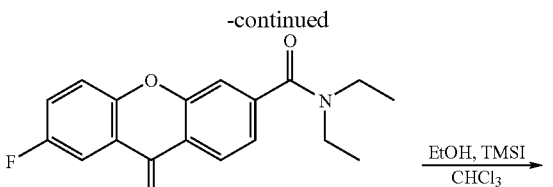

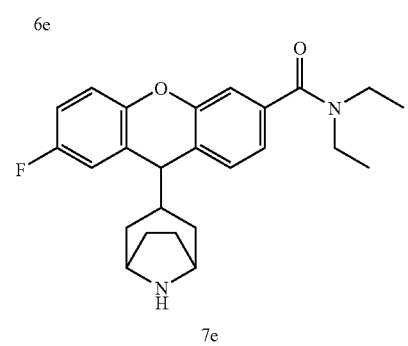

Procedure 19

2-(4-Fluorophenoxy)-terephthalic acid dimethyl ester, 1e

To a solution of 4-fluorophenol (1.25 g, 11.15 mmol) in toluene (50 mL) was added cesium carbonate (6.10 g, 18.7 mmol) and the mixture was stirred for 15 min at rt. 2-Iodoterephthalic acid dimethyl ester (3.0 g, 9.37 mmol) and tetrakisacetonitrilecopper hexafluorophosphate (435 mg) were added, and the mixture was heated to reflux for 18 h. The mixture was allowed to cool to rt and poured into an ice-cold saturated ammonium chloride solution. The organic layer was separated, washed with a saturated potassium carbonate solution and brine, dried over magnesium sulfate, filtered, and evaporated. The residue was purified via flash column chromatography (elent gradient 1% to 20% EtOAc in heptane) to yield 1.25 g (43.8%) of title compound 2-(4-fluorophenoxy)-terephthalic acid dimethyl ester, 1e. MS m/z (MH⁺) 305.0.

7-Fluoro-9-oxo-9H-xanthene-3-carboxylic acid methyl ester, 2e

Using an adaptation of the method described in Procedure 15, substituting 2-(4-fluorophenoxy)-terephthalic acid dimethyl ester, 1e for 2-(2-methoxyphenoxy)-terephthalic acid dimethyl ester, 1c, the title compound 7-fluoro-9-oxo-9H-xanthene-3-carboxylic acid methyl ester, 2e was obtained. MS m/z (MH⁺) 272.9.

7-Fluoro-9-oxo-9H-xanthene-3-carboxylic acid, 3e

Using an adaptation of the method described in Procedure 5, substituting 7-fluoro-9-oxo-9H-xanthene-3-carboxylic acid methyl ester, 2e for 9-oxo-9H-xanthene-3-carboxylic acid methyl ester, 4a, the title compound 7-fluoro-9-oxo-9H-xanthene-3-carboxylic acid, 3e was obtained. MS m/z (MH⁺) 258.9.

7-Fluoro-9-oxo-9H-xanthene-3-carboxylic acid diethylamide, 4e

Using an adaptation of the method described in Procedure 16, substituting 7-fluoro-9-oxo-9H-xanthene-3-carboxylic acid, 3e for 5-methoxy-9-oxo-9H-xanthene-3-carboxylic acid, 3d, and HATU for HBTU, the title compound 7-fluoro-9-oxo-9H-xanthene-3-carboxylic acid diethylamide, 4e was obtained. MS m/z (MH$^+$) 314.

7-Fluoro-9-[8-(2,2,2-trifluoro-acetyl)-8-aza-bicyclo[3.2.1]oct-3-ylidene]-9H-xanthene-3-carboxylic acid diethylamide, 5e Using an adaptation of the method described in Procedure 7, substituting 7-fluoro-9-oxo-9H-xanthene-3-carboxylic acid diethylamide, 4e for 9-oxo-9H-xanthene-3-carboxylic acid diethylamide, 6a, and N-trifluoroacetylnortropinone for N-carbethoxynortropinone, the title compound 7-fluoro-9-[8-(2,2,2-trifluoro-acetyl)-8-aza-bicyclo[3.2.1]oct-3-ylidene]-9H-xanthene-3-carboxylic acid diethylamide, 5e was obtained.

9-(8-Aza-bicyclo[3.2.1]oct-3-ylidene)-7-fluoro-9H-xanthene-3-carboxylic acid diethylamide, 6e Using an adaptation of the method described in Procedure 17, substituting 7-fluoro-9-[8-(2,2,2-trifluoro-acetyl)-8-aza-bicyclo[3.2.1]oct-3-ylidene]-9H-xanthene-3-carboxylic acid diethylamide, 5e for 5-methoxy-9-[8-(2,2,2-trifluoro-acetyl)-8-aza-bicyclo[3.2.1]oct-3-ylidene]-9H-xanthene-3-carboxylic acid diethylamide, 5d, the title compound 9-(8-aza-bicyclo[3.2.1]oct-3-ylidene)-7-fluoro-9H-xanthene-3-carboxylic acid diethylamide, 6e was obtained as TFA salt after reverse phase HPLC purification (eluent gradient: CH$_3$CN in H$_2$O containing 0.1% TFA). MS m/z (MH$^+$) 407.1.

9-(8-Aza-bicyclo[3.2.1]oct-3-yl)-7-fluoro-9H-xanthene-3-carboxylic acid diethylamide, 7e Using an adaptation of the method described in Procedure 9, substituting 9-(8-aza-bicyclo[3.2.1]oct-3-ylidene)-7-fluoro-9H-xanthene-3-carboxylic acid diethylamide, 6e for 9-(8-aza-bicyclo[3.2.1]oct-3-ylidene)-9H-xanthene-3-carboxylic acid diethylamide, 8a, the title compound 9-(8-aza-bicyclo[3.2.1]oct-3-yl)-7-fluoro-9H-xanthene-3-carboxylic acid diethylamide, 7e was obtained as a TFA salt after reverse phase HPLC purification (eluent gradient: CH$_3$CN in H$_2$O containing 0.1% TFA). MS m/z (MH$^+$) 409.1.

Example F

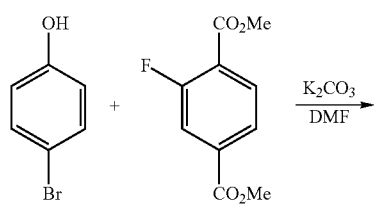

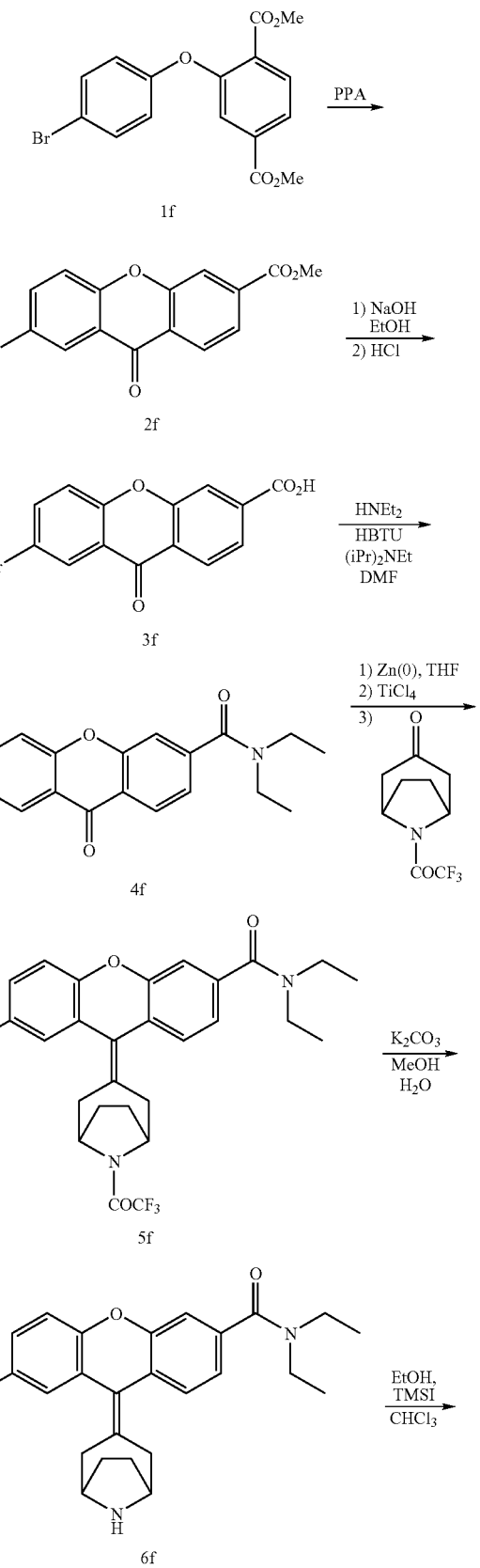

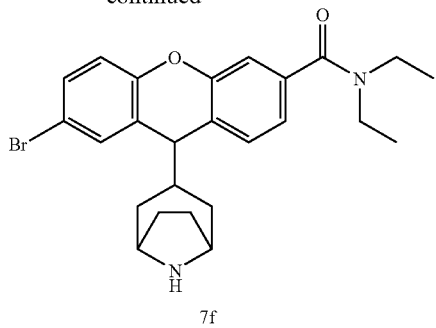

7f

2-(4-Bromophenoxy)-terephthalic acid dimethyl ester, 1f

Using an adaptation of the method described in Procedure 14, substituting 4-bromophenol for 2-methoxyphenol, the title compound 2-(4-bromophenoxy)-terephthalic acid dimethyl ester, 1f was obtained

7-Bromo-9-oxo-9H-xanthene-3-carboxylic acid methyl ester, 2f

Using an adaptation of the method described in Procedure 15, substituting 2-(4-bromophenoxy)-terephthalic acid dimethyl ester, 1f for 2-(2-methoxy-phenoxy)-terephthalic acid dimethyl ester, 1c the title compound 7-bromo-9-oxo-9H-xanthene-3-carboxylic acid methyl ester, 2f was obtained. MS m/z (MH$^+$) 332.9.

7-Bromo-9-oxo-9H-xanthene-3-carboxylic acid, 3f

Using an adaptation of the method described in Procedure 5, substituting 7-bromo-9-oxo-9H-xanthene-3-carboxylic acid methyl ester, 2f for 9-oxo-9H-xanthene-3-carboxylic acid methyl ester, 4a, the title compound 7-bromo-9-oxo-9H-xanthene-3-carboxylic acid, 3f was obtained.

7-Bromo-9-oxo-9H-xanthene-3-carboxylic acid diethylamide, 4f

Using an adaptation of the method described in Procedure 16, substituting 7-bromo-9-oxo-9H-xanthene-3-carboxylic acid, 3f for 5-methoxy-9-oxo-9H-xanthene-3-carboxylic acid, 3d, the title compound 7-bromo-9-oxo-9H-xanthene-3-carboxylic acid diethylamide, 4f was obtained. MS m/z (MH$^+$) 373.9/376.

7-Bromo-9-[8-(2,2,2-trifluoro-acetyl)-8-aza-bicyclo[3.2.1]oct-3-ylidene]-9H-xanthene-3-carboxylic acid diethylamide, 5f Using an adaptation of the method described in Procedure 7, substituting 7-bromo-9-oxo-9H-xanthene-3-carboxylic acid diethylamide, 4e for 9-oxo-9H-xanthene-3-carboxylic acid diethylamide, 6a, and N-trifluoroacetylnortropinone for N-carbethoxynortropinone, the title compound 7-bromo-9-[8-(2,2,2-trifluoro-acetyl)-8-aza-bicyclo[3.2.1]oct-3-ylidene]-9H-xanthene-3-carboxylic acid diethylamide, 5f was obtained

9-(8-Aza-bicyclo[3.2.1]oct-3-ylidene)-7-bromo-9H-xanthene-3-carboxylic acid diethylamide, 6f Using an adaptation of the method described in Procedure 17, substituting 7-bromo-9-[8-(2,2,2-trifluoro-acetyl)-8-aza-bicyclo[3.2.1]oct-3-ylidene]-9H-xanthene-3-carboxylic acid diethylamide, 5f for 5-methoxy-9-[8-(2,2,2-trifluoro-acetyl)-8-aza-bicyclo[3.2.1]oct-3-ylidene]-9H-xanthene-3-carboxylic acid diethylamide, 5d, the title compound 9-(8-aza-bicyclo[3.2.1]oct-3-ylidene)-7-bromo-9H-xanthene-3-carboxylic acid diethylamide, 6f was obtained as a TFA salt after reverse phase HPLC purification (eluent gradient: CH$_3$CN in H$_2$O containing 0.1% TFA). MS m/z (MH$^+$) 467/468.9.

9-(8-Aza-bicyclo[3.2.1]oct-3-yl)-7-bromo-9H-xanthene-3-carboxylic acid diethylamide, 7f Using an adaptation of the method described in Procedure 9, substituting 9-(8-aza-bicyclo[3.2.1]oct-3-ylidene)-7-bromo-9H-xanthene-3-carboxylic acid diethylamide, 6e for 9-(8-aza-bicyclo[3.2.1]oct-3-ylidene)-9H-xanthene-3-carboxylic acid diethylamide, 8a, the title compound 9-(8-aza-bicyclo[3.2.1]oct-3-yl)-7-bromo-9H-xanthene-3-carboxylic acid diethylamide, 7e was obtained as a TFA salt after reverse phase HPLC purification (eluent gradient: CH$_3$CN in H$_2$O containing 0.1% TFA). MS m/z (MH$^+$) 469.1.

Example G

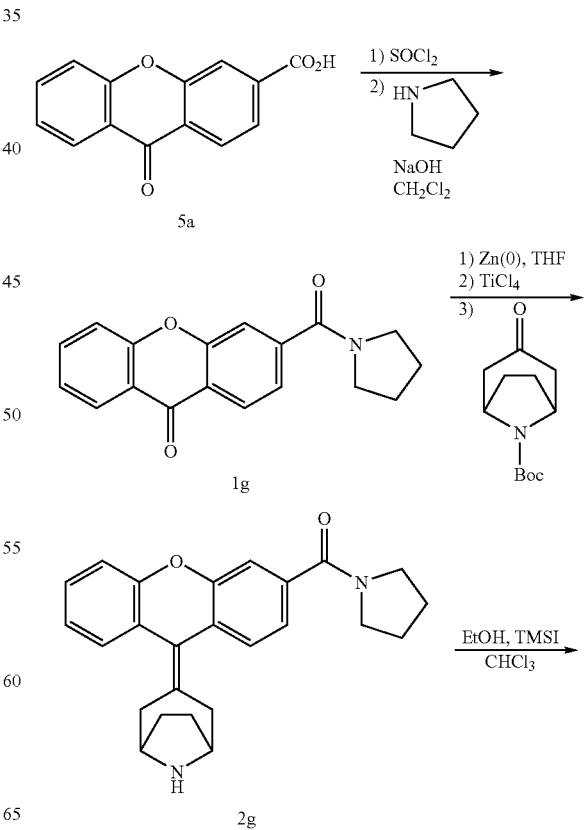

-continued

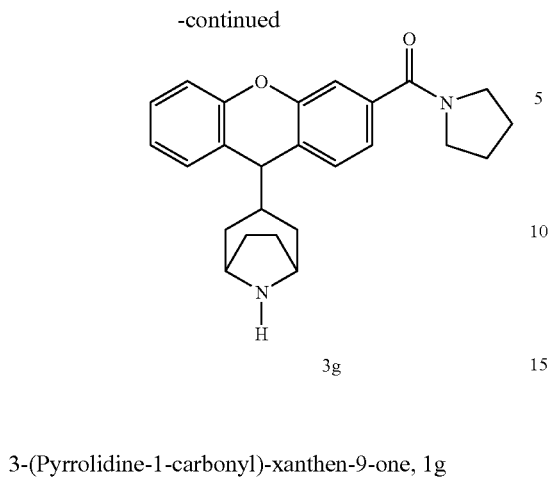

3-(Pyrrolidine-1-carbonyl)-xanthen-9-one, 1g

Using an adaptation of the method described in Procedure 6, substituting pyrrolidine for diethylamine, the title compound 3-(pyrrolidine-1-carbonyl)-xanthen-9-one, 1g was obtained.

[9-(8-Aza-bicyclo[3.2.1]oct-3-ylidene)-9H-xanthen-3-yl]-pyrrolidin-1-yl-methanone, 2g Using an adaptation of the method described in Procedure 7, substituting 3-(pyrrolidine-1-carbonyl)-xanthen-9-one, 1g for 9-oxo-9H-xanthene-3-carboxylic acid diethylamide, 6a and 3-oxo-8-aza-bicyclo[3.2.1]octane-8-carboxylic acid tert-butyl ester for N-carbethoxynortropinone, the title compound [9-(8-aza-bicyclo[3.2.1]oct-3-ylidene)-9H-xanthen-3-yl]-pyrrolidin-1-yl-methanone, 2g was obtained as a TFA salt after reverse phase HPLC purification (eluent gradient: $CH_3CN$ in $H_2O$ containing 0.1% TFA).

[9-(8-Aza-bicyclo[3.2.1]oct-3-yl)-9H-xanthen-3-yl]-pyrrolidin-1-yl-methanone, 3g Using an adaptation of the method described in Procedure 9, substituting [9-(8-aza-bicyclo[3.2.1]oct-3-ylidene)-9H-xanthen-3-yl]-pyrrolidin-1-yl-methanone, 2g for 9-(8-aza-bicyclo[3.2.1]oct-3-ylidene)-9H-xanthene-3-carboxylic acid diethylamide, 8a, the title [9-(8-aza-bicyclo[3.2.1]oct-3-yl)-9H-xanthen-3-yl]-pyrrolidin-1-yl-methanone, 3g was obtained as a TFA salt after reverse phase HPLC purification (eluent gradient: $CH_3CN$ in $H_2O$ containing 0.1% TFA). MS m/z ($MH^+$) 389.1.

Example H

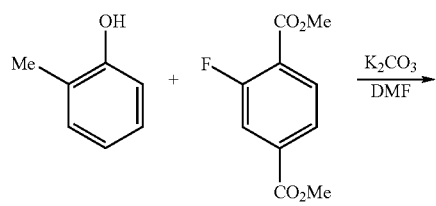

-continued

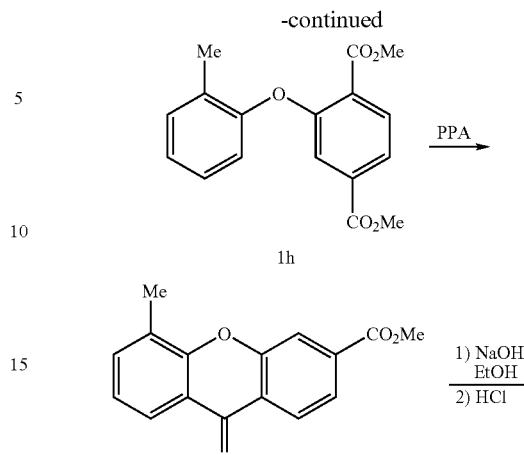

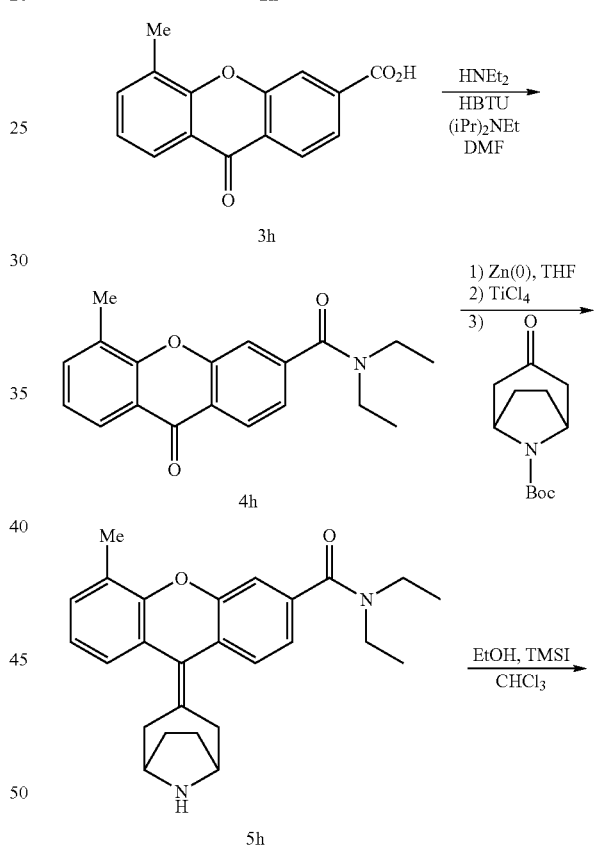

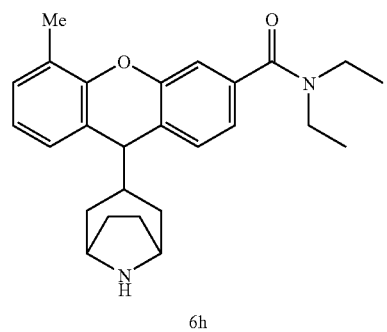

2-o-Tolyloxy-terephthalic acid dimethyl ester, 1h

Using an adaptation of the method described in Procedure 14, substituting 2-methylphenol for 2-methoxyphenol, title compound 2-o-tolyloxy-terephthalic acid dimethyl ester, 1h was obtained. MS m/z (MH⁺) 300.9.

5-Methyl-9-oxo-9H-xanthene-3-carboxylic acid methyl ester, 2h

Using an adaptation of the method described in Procedure 15, substituting 2-o-tolyloxy-terephthalic acid dimethyl ester, 1h for 2-(2-methoxyphenoxy)-terephthalic acid dimethyl ester, 1c, the title compound 5-methyl-9-oxo-9H-xanthene-3-carboxylic acid methyl ester, 2h was obtained. MS m/z (MH⁺) 269.0.

5-Methyl-9-oxo-9H-xanthene-3-carboxylic acid, 3h

Using an adaptation of the method described in Procedure 5, substituting 5-methyl-9-oxo-9H-xanthene-3-carboxylic acid methyl ester, 2h for 9-oxo-9H-xanthene-3-carboxylic acid methyl ester, 4a, title compound 5-methyl-9-oxo-9H-xanthene-3-carboxylic acid, 3h was obtained. MS m/z (MH⁺) 254.9.

5-Methyl-9-oxo-9H-xanthene-3-carboxylic acid diethylamide, 4h

Using an adaptation of the method described in Procedure 19, substituting 5-methyl-9-oxo-9H-xanthene-3-carboxylic acid, 3h for 5-methoxy-9-oxo-9H-xanthene-3-carboxylic acid, 3d, the title compound 5-methyl-9-oxo-9H-xanthene-3-carboxylic acid diethylamide, 4h was obtained. MS m/z (MH⁺) 310.1.

9-(8-Aza-bicyclo[3.2.1]oct-3-ylidene)-5-methyl-9H-xanthene-3-carboxylic acid diethylamide, 5h Using an adaptation of the method described in Procedure 7, substituting 5-methyl-9-oxo-9H-xanthene-3-carboxylic acid diethylamide, 4h for 9-oxo-9H-xanthene-3-carboxylic acid diethylamide, 6a, and 3-oxo-8-aza-bicyclo[3.2.1]-octane-8-carboxylic acid tert-butyl ester for N-carbethoxynortropinone, title compound 9-(8-aza-bicyclo[3.2.1]oct-3-ylidene)-5-methyl-9H-xanthene-3-carboxylic acid diethylamide, 5h was obtained. MS m/z (MH⁺) 402.9.

9-(8-Aza-bicyclo[3.2.1]oct-3-yl)-5-methyl-9H-xanthene-3-carboxylic acid diethylamide, 6h Using an adaptation of the method described in Procedure 9, substituting 9-(8-aza-bicyclo[3.2.1]oct-3-ylidene)-5-methyl-9H-xanthene-3-carboxylic acid diethylamide, 5h for 9-(8-aza-bicyclo[3.2.1]oct-3-ylidene)-9H-xanthene-3-carboxylic acid diethylamide, 8a, the title compound 9-(8-aza-bicyclo[3.2.1]oct-3-yl)-5-methyl-9H-xanthene-3-carboxylic acid diethylamide, 6h was obtained as a TFA salt after reverse phase HPLC purification (eluent gradient: CH₃CN in H₂O containing 0.1% TFA). MS m/z (MH⁺) 405.1.

Example I

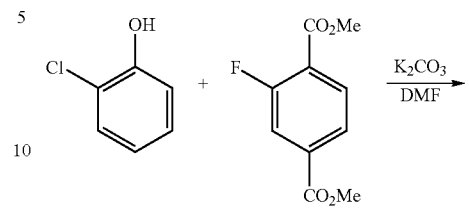

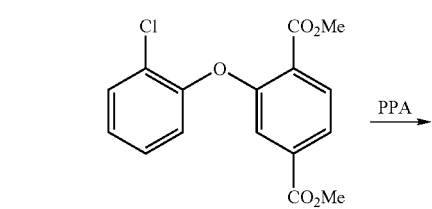

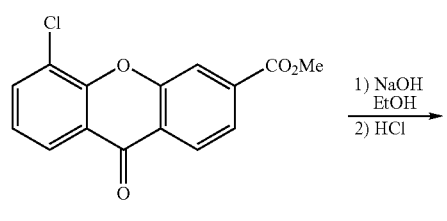

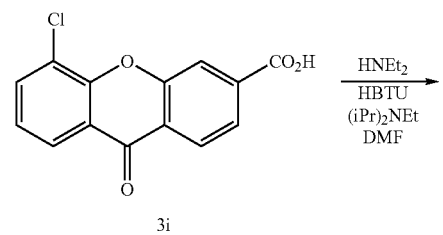

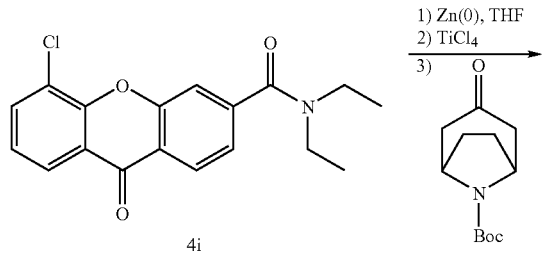

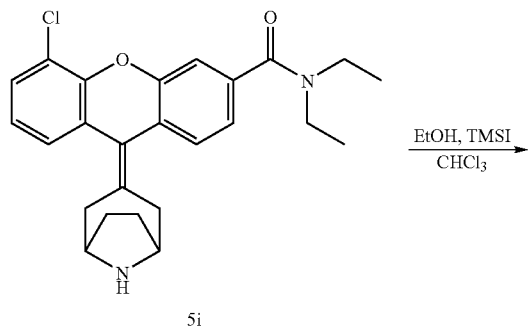

-continued

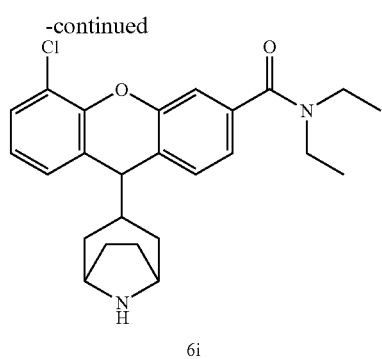

6i

2-(2-Chlorophenoxy)-terephthalic acid dimethyl ester, 1i

Using an adaptation of the method described in Procedure 17, substituting 2-chlorophenol for 2-methoxyphenol, the title compound 2-(2-chlorophenoxy)-terephthalic acid dimethyl ester, 1i was obtained. MS m/z (MH$^+$) 320.9.

5-Chloro-9-oxo-9H-xanthene-3-carboxylic acid methyl ester, 2i

Using an adaptation of the method described in Procedure 15, substituting 2-(2-chlorophenoxy)-terephthalic acid dimethyl ester, 1i for 2-(2-methoxyphenoxy)-terephthalic acid dimethyl ester, 1c, the title compound 5-chloro-9-oxo-9H-xanthene-3-carboxylic acid methyl ester, 2i was obtained. MS m/z (MH$^+$) 289.0.

5-Chloro-9-oxo-9H-xanthene-3-carboxylic acid, 3i

Using an adaptation of the method described in Procedure 5, substituting 5-chloro-9-oxo-9H-xanthene-3-carboxylic acid methyl ester, 2i for 9-oxo-9H-xanthene-3-carboxylic acid methyl ester, 4a, title compound 5-chloro-9-oxo-9H-xanthene-3-carboxylic acid, 3i was obtained.

5-Chloro-9-oxo-9H-xanthene-3-carboxylic acid diethylamide, 4i

Using an adaptation of the method described in Procedure 16, substituting 5-chloro-9-oxo-9H-xanthene-3-carboxylic acid, 3i for 5-methoxy-9-oxo-9H-xanthene-3-carboxylic acid, 3c, the title compound 5-chloro-9-oxo-9H-xanthene-3-carboxylic acid diethylamide, 4i was obtained. MS m/z (MH$^+$) 330.0.

9-(8-Aza-bicyclo[3.2.1]oct-3-ylidene)-5-chloro-9H-xanthene-3-carboxylic acid diethylamide, 5i Using an adaptation of the method described in Procedure 7, substituting 5-chloro-9-oxo-9H-xanthene-3-carboxylic acid diethylamide, 4i for 9-oxo-9H-xanthene-3-carboxylic acid diethylamide, 6a, and 3-oxo-8-aza-bicyclo[3.2.1]-octane-8-carboxylic acid tert-butyl ester for N-carbethoxynortropinone, title compound 9-(8-aza-bicyclo[3.2.1]oct-3-ylidene)-5-chloro-9H-xanthene-3-carboxylicacid diethylamide, 5i was obtained. MS m/z (MH$^+$) 423.1.

9-(8-Aza-bicyclo[3.2.1]oct-3-yl)-5-chloro-9H-xanthene-3-carboxylic acid diethylamide, 6i Using an adaptation of the method described in Procedure 9, substituting 9-(8-aza-bicyclo[3.2.1]oct-3-ylidene)-5-chloro-9H-xanthene-3-carboxylic acid diethylamide, 5i for 9-(8-aza-bicyclo[3.2.1]oct-3-ylidene)-9H-xanthene-3-carboxylic acid diethylamide, 8a, the title compound 9-(8-aza-bicyclo[3.2.1]oct-3-yl)-5-chloro-9H-xanthene-3-carboxylic acid diethylamide, 6i was obtained as a TFA salt after reverse phase HPLC purification (eluent gradient: CH$_3$CN in H$_2$O containing 0.1% TFA). MS m/z (MH$^+$) 425.1.

Example J

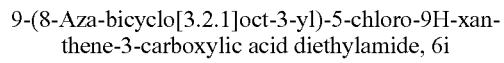

-continued

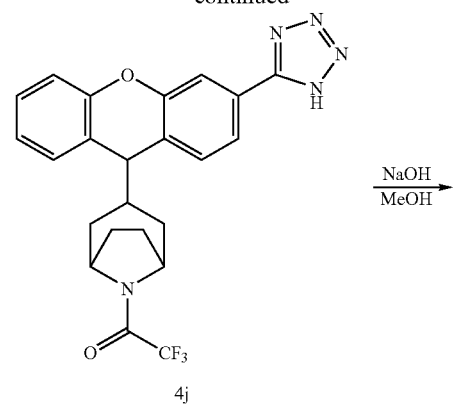

4j

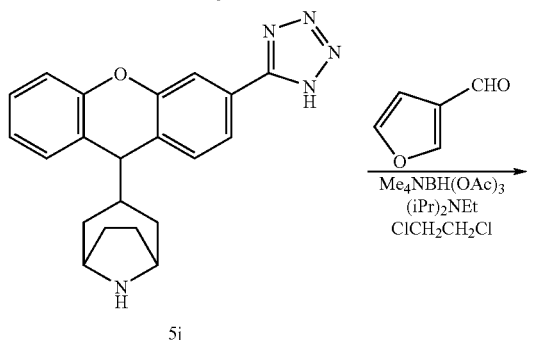

5j

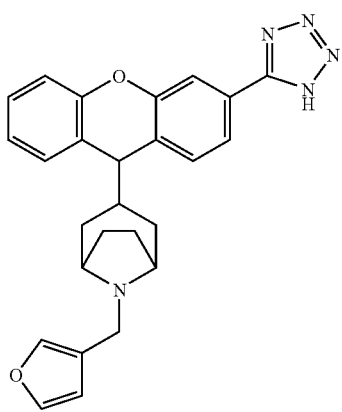

6j

Procedure 20

1-[3-(3-Bromoxanthen-9-ylidene)-8-aza-bicyclo[3.2.1]oct-8-yl]-2,2,2-trifluoroethanone, 1j To a solution of 3-(3-bromo-xanthen-9-ylidene)-8-aza-bicyclo[3.2.1]octane, 1b (3.12 g, 8.47 mmol) and N,N-diisopropyl-N-ethylamine (1.92 mL, 11 mmol) in methylene chloride (100 mL) at 0° C. was added trifluoroactic anhydride (1.41 mL, 10.2 mmol), and the mixture was allowed to stir at rt for 18 h. The solution was washed with a 1N HCl solution, dried over MgSO₄, filtered, and evaporated. The residue was purified via flash column cvhromatography (eluent gradient: 5% to 25% EtOAc in heptane) to yield 3.93 g (90%) of title compound 1-[3-(3-bromoxanthen-9-ylidene)-8-aza-bicyclo[3.2.1]oct-8-yl]-2,2,2-trifluoroethanone, 1j 1-[3-(3-Bromo-9H-xanthen-9-yl)-8-aza-bicyclo[3.2.1]oct-8-yl]-2,2,2-trifluoro-ethanone, 2j Using an adaptation of the method described in Procedure 9, substituting 1-[3-(3-bromoxanthen-9-ylidene)-8-aza-bicyclo[3.2.1]oct-8-yl]-2,2,2-trifluoro-ethanone, 1j for 9-(8-aza-bicyclo[3.2.1]oct-3-ylidene)-9H-xanthene-3-carboxylic acid diethylamide, 8a, the title compound 1-[3-(3-bromo-9H-xanthen-9-yl)-8-aza-bicyclo[3.2.1]oct-8-yl]-2,2,2-trifluoro-ethanone, 2j was obtained after puirification via flash column chromatography (eluent gradient: 5% to 25% EtOAc in heptane). MS m/z (MH⁺) 465.8.

Procedure 21

9-[8-(2,2,2-Trifluoroacetyl)-8-aza-bicyclo[3.2.1]oct-3-yl]-9H-xanthene-3-carbonitrile, 3j To a solution of 1-[3-(3-bromo-9H-xanthen-9-yl)-8-aza-bicyclo[3.2.1]oct-8-yl]-2,2,2-trifluoro-ethanone, 2j (1.8 g, 3.86 mmol) in DMF (40 mL) was added copper cyanide (0.69 g, 7.72 mmol) and potassium iodide (50 mg), and the mixture was heated to reflux for 18 h. More copper cyanide (0.43 g) was added, and the mixture was heated to reflux for 30 h. The mixture was filtered and poured in ice-water. The solid was separated via filtration, washed with water, and air-dried. The crude product was purified via flash column chromatography (eluent gradient: 5% to 30% ethyl acetate in heptane) to yield 0.956 g (60%) of title compound 9-[8-(2,2,2-trifluoroacetyl)-8-aza-bicyclo[3.2.1]oct-3-yl]-9H-xanthene-3-carbonitrile, 3j. MS m/z (MH⁺) 412.8.

Procedure 22

2,2,2-Trifluoro-1-{3-[3-(1H-tetrazol-5-yl)-9H-xanthen-9-yl]-8-aza-bicyclo[3.2.1]oct-8-yl}-ethanone, 4j To a solution of 9-[8-(2,2,2-trifluoroacetyl)-8-aza-bicyclo[3.2.1]oct-3-yl]-9H-xanthene-3-carbonitrile, 3j (0.35 g; 0.848 mmol) in DMF (10 mL) were added sodium azide (0.165 g, 2.54 mmol) and ammonium chloride (0.136 g; 2.5 mmol), and the mixture was heated at 120° C. for 3 h. The mixture was allowed to cool to rt, poured into water, and the solid was separated via filtration, yielding 0.33 g (86%) of title compound 2,2,2-trifluoro-1-{3-[3-(1H-tetrazol-5-yl)-9H-xanthen-9-yl]-8-aza-bicyclo[3.2.1]oct-8-yl}-ethanone, 4j Procedure 23

3-[3-(1H-Tetrazol-5-yl)-9H-xanthen-9-yl]-8-aza-bicyclo[3.2.1]octane, 5j

To a solution of 2,2,2-trifluoro-1-{3-[3-(1H-tetrazol-5-yl)-9H-xanthen-9-yl]-8-aza-bicyclo[3.2.1]oct-8-yl}-ethanone, 4j (0.33 g, 0.724 mmol) in methanol (10 mL) was added a 1N NaOH solution (2.17 mmol, 2.17 mL), and the mixture was heated to reflux for 1 h. The mixture was allowed to cool to rt and evaporated. The residue was purified via reverse phase HPLC (eluent gradient: CH₃CN in H₂O containing 0.1% TFA) to yield 0.22 g (64%) of title compound 3-[3-(1H-tetrazol-5-yl)-9H-xanthen-9-yl]-8-aza-bicyclo[3.2.1]octane, 5j as a TFA salt. MS m/z (MH⁺) 360.1.

8-Furan-3-ylmethyl-3-[3-(1H-tetrazol-5-yl)-9H-xanthen-9-yl]-8-aza-bicyclo[3.2.1]octane, 6j Using an adaptation of the method described in Procedure 12, substituting the TFA salt of 3-[3-(1H-tetrazol-5-yl)-9H-xanthen-9-yl]-8-aza-bicyclo[3.2.1]octane, 5j for 3-(3-pyridin-3-yl-9H-xanthen-9-yl)-8-aza-bicyclo[3.2.1]octane, 3b, title compound 8-furan-3-ylmethyl-3-[3-(1H-tetrazol-5-yl)-9H-xanthen-9-yl]-8-aza-bicyclo[3.2.1]octane, 6j was obtained as a TFA salt. MS m/z (MH+) 440.1.

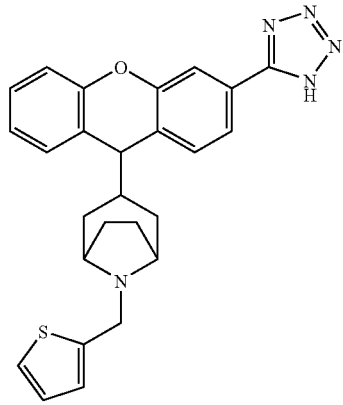

3-[3-(1H-Tetrazol-5-yl)-9H-xanthen-9-yl]-8-thiophen-2-ylmethyl-8-aza-bicyclo[3.2.1]octane, 7j Using an adaptation of the method described in Procedure 12, substituting the TFA salt of 3-[3-(1H-tetrazol-5-yl)-9H-xanthen-9-yl]-8-aza-bicyclo[3.2.1]octane, 5j for 3-(3-pyridin-3-yl-9H-xanthen-9-yl)-8-aza-bicyclo[3.2.1]octane, 3b, and 2-thiophene carboxaldehyde for 3-furaldehyde, title compound 3-[3-(1H-tetrazol-5-yl)-9H-xanthen-9-yl]-8-thiophen-2-ylmethyl-8-aza-bicyclo[3.2.1]octane, 7j was obtained as a TFA salt. MS m/z (MH+) 456.0.

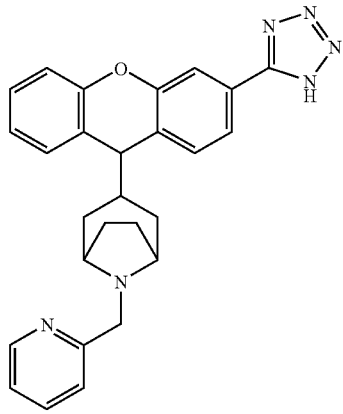

8-Pyridin-2-ylmethyl-3-[3-(1H-tetrazol-5-yl)-9H-xanthen-9-yl]-8-aza-bicyclo[3.2.1]octane, 8j Using an adaptation of the method described in Procedure 12, substituting the TFA salt of 3-[3-(1H-tetrazol-5-yl)-9H-xanthen-9-yl]-8-aza-bicyclo[3.2.1]octane, 5j for 3-(3-pyridin-3-yl-9H-xanthen-9-yl)-8-aza-bicyclo[3.2.1]octane, 3b, and 2-pyridyl carboxaldehyde for 3-furaldehyde, title compound 8-pyridin-2-ylmethyl-3-[3-(1H-tetrazol-5-yl)-9H-xanthen-9-yl]-8-aza-bicyclo[3.2.1]octane, 8j was obtained as a TFA salt. MS m/z (MH+) 451.1.

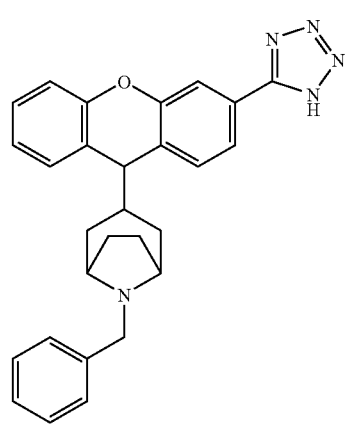

8-Benzyl-3-[3-(1H-tetrazol-5-yl)-9H-xanthen-9-yl]-8-aza-bicyclo[3.2.1]octane, 9j Using an adaptation of the method described in Procedure 12, substituting the TFA salt of 3-[3-(1H-tetrazol-5-yl)-9H-xanthen-9-yl]-8-aza-bicyclo[3.2.1]octane, 5j for 3-(3-pyridin-3-yl-9H-xanthen-9-yl)-8-aza-bicyclo[3.2.1]octane, 3b, and benzaldehyde for 3-furaldehyde, title compound 8-benzyl-3-[3-(1H-tetrazol-5-yl)-9H-xanthen-9-yl]-8-aza-bicyclo[3.2.1]octane, 9j was obtained as a TFA salt. MS m/z (MH+) 450.1.

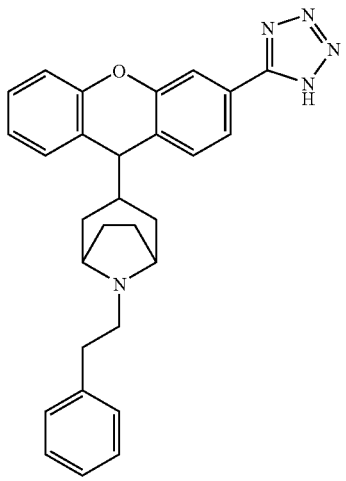

8-Phenethyl-3-[3-(1H-tetrazol-5-yl)-9H-xanthen-9-yl]-8-aza-bicyclo[3.2.1]octane, 10j Using an adaptation of the method described in Procedure 12, substituting the TFA salt of 3-[3-(1H-tetrazol-5-yl)-9H-xanthen-9-yl]-8-aza-bicyclo[3.2.1]octane, 5j for 3-(3-pyridin-3-yl-9H-xanthen-9-yl)-8-aza-bicyclo[3.2.1]octane, 3b, and phenyl acetaldehyde for 3-furaldehyde, title compound 8-phenethyl-3-[3-(1H-tetrazol-5-yl)-9H-xanthen-9-yl]-8-aza-bicyclo[3.2.1]octane, 10j was obtained as a TFA salt. MS m/z (MH$^+$) 464.1.
Example K
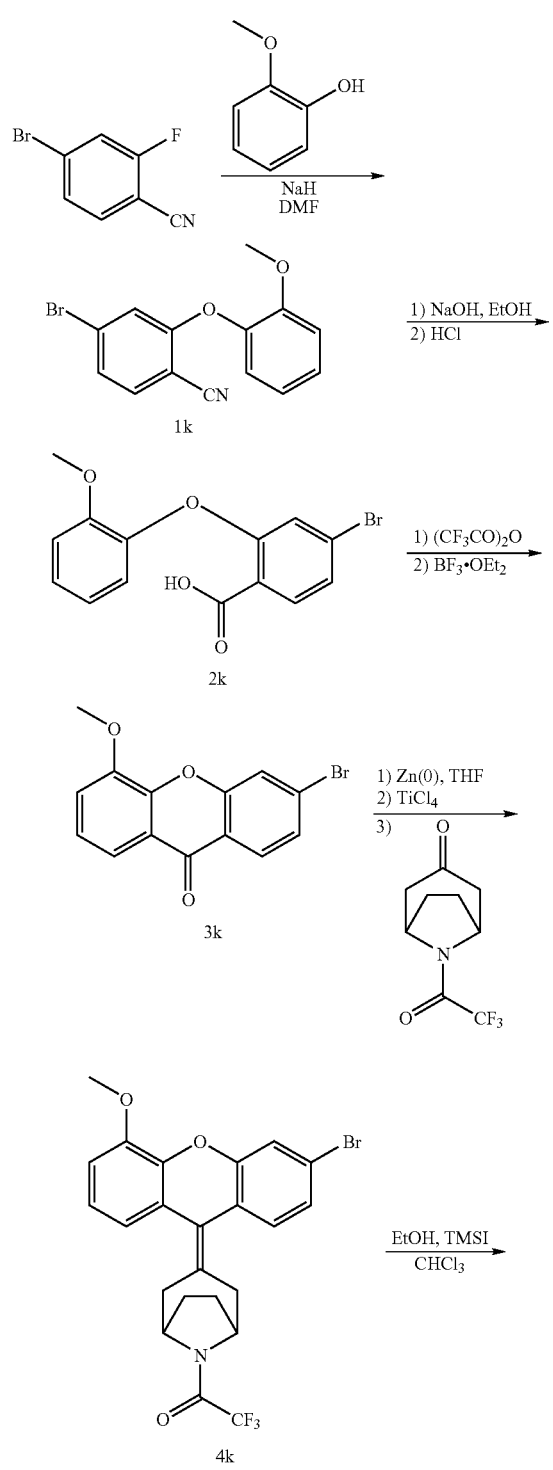
-continued -continued

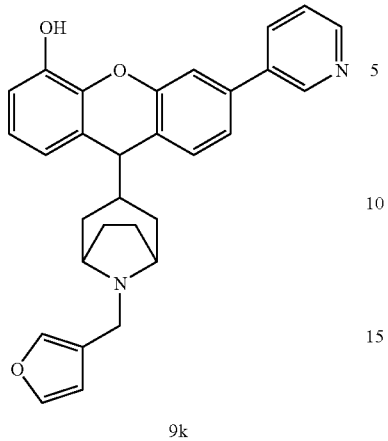

9k

4-Bromo-2-(2-methoxy-phenoxy)-benzonitrile, 1k

Using an adaptation of the method described in Procedure 1, substituting 2-methoxyphenol for phenol, the title compound 4-bromo-2-(2-methoxy-phenoxy)-benzonitrile, 1 k was obtained. MS m/z (MH$^+$) 303.8, 305.8.

4-Bromo-2-(2-methoxy-phenoxy)-benzoic acid, 2k

Using an adaptation of the method described in Procedure 2, substituting 4-bromo-2-(2-methoxy-phenoxy)-benzonitrile, 1k for 4-bromo-2-phenoxybenzonitrile, 1a, the title compound 4-bromo-2-(2-methoxy-phenoxy)-benzoic acid, 2k was obtained. MS m/z (MH$^+$) 322.8, 324.7.

3-Bromo-5-methoxy-xanthen-9-one, 3k

Using an adaptation of the method described in Procedure 3, substituting 4-bromo-2-(2-methoxy-phenoxy)-benzoic acid, 2k for 4-bromo-2-phenoxybenzoic acid, 2a, the title compound 3-bromo-5-methoxy-xanthen-9-one, 3k was obtained. MS m/z (MH$^+$) 304.8, 306.7.

1-[3-(3-Bromo-5-methoxy-xanthen-9-ylidene)-8-aza-bicyclo[3.2.1]oct-8-yl]-2,2,2-trifluoro-ethanone, 4k Using an adaptation of the method described in Procedure 7, substituting 3-bromo-5-methoxy-xanthen-9-one, 3k for 9-oxo-9H-xanthene-3-carboxylic acid diethylamide, 6a and 8-(2,2,2-trifluoro-acetyl)-8-aza-bicyclo[3.2.1]octan-3-one for N-carbethoxynortropinone, the title compound 1-[3-(3-bromo-5-methoxy-xanthen-9-ylidene)-8-aza-bicyclo[3.2.1]oct-8-yl]-2,2,2-trifluoro-ethanone, 4k was obtained. MS m/z (MH$^+$) 467.7, 469.7.

1-[3-(3-Bromo-5-methoxy-9H-xanthen-9-yl)-8-aza-bicyclo[3.2.1]oct-8-yl]-2,2,2-trifluoro-ethanone, 5k Using an adaptation of the method described in Procedure 4, substituting 1-[3-(3-bromo-5-methoxy-xanthen-9-ylidene)-8-aza-bicyclo[3.2.1]oct-8-yl]-2,2,2-trifluoro-ethanone, 4k for 9-(8-aza-bicyclo[3.2.1]oct-3-ylidene)-9H-xanthene-3-carboxylic acid diethylamide, 8a, the title compound 1-[3-(3-bromo-5-methoxy-9H-xanthen-9-yl)-8-aza-bicyclo[3.2.1]oct-8-yl]-2,2,2-trifluoro-ethanone, 5k was obtained

Procedure 24

2,2,2-Trifluoro-1-[3-(5-methoxy-3-pyridin-3-yl-9H-xanthen-9-yl)-8-aza-bicyclo[3.2.1]oct-8-yl]-ethanone, 6k To a solution of 1-[3-(3-bromo-5-methoxy-9H-xanthen-9-yl)-8-aza-bicyclo[3.2.1]oct-8-yl]-2,2,2-trifluoro-ethanone, 5k (0.505 g, 1.02 mmol) in dioxane (15 mL) were added 3-pyridylboronic acid (0.188 g, 1.53 mmol), di-tert-butylphosphine palladium (II) dichloride (35 mg), and a 2 M sodium carbonate solution (1.3 mL, 2.54 mmol), and the mixture was heated at 75° C. for 2 h under an argon atmosphere. The mixture was allowed to cool to rt and water and ethyl acetate were added. The organic phase was washed with brine, dried over MgSO$_4$, filtered and concentrated. The residue was purified by flash column chromatography (eluent gradient: 50% to 95% EtOAc in heptane) to yield 0.47 g (93%) of title compound 2,2,2-trifluoro-1-[3-(5-methoxy-3-pyridin-3-yl-9H-xanthen-9-yl)-8-aza-bicyclo[3.2.1]oct-8-yl]-ethanone, 6k. MS m/z (MH$^+$) 495.1.

3-(5-Methoxy-3-pyridin-3-yl-9H-xanthen-9-yl)-8-aza-bicyclo[3.2.1]octane, 7k

Using an adaptation of the method described in Procedure 23, substituting 2,2,2-trifluoro-1-[3-(5-methoxy-3-pyridin-3-yl-9H-xanthen-9-yl)-8-aza-bicyclo[3.2.1]oct-8-yl]-ethanone, 6k for 2,2,2-trifluoro-1-{3-[3-(1H-tetrazol-5-yl)-9H-xanthen-9-yl]-8-aza-bicyclo[3.2.1]oct-8-yl}-ethanone, 4j, the title compound 3-(5-methoxy-3-pyridin-3-yl-9H-xanthen-9-yl)-8-aza-bicyclo[3.2.1]octane, 7k was obtained as a TFA salt. MS m/z (MH$^+$) 399.1.

Procedure 25

9-(8-Aza-bicyclo[3.2.1]oct-3-yl)-6-pyridin-3-yl-9H-xanthen-4-ol, 8k

To a solution of 3-(5-methoxy-3-pyridin-3-yl-9H-xanthen-9-yl)-8-aza-bicyclo[3.2.1]octane, 7k (0.3 g, 0.803 mmol) in CH$_2$Cl$_2$ (20 mL) was added dropwise a 1M BBr$_3$ solution in methylene chloride (3.2 mL, 3.2 mmol) at 0° C. The mixture was stirred at rt for 24 h, and quenched with a saturated NaHCO$_3$ solution (20 mL). The organic layer was dried over MgSO$_4$ and concentrated. The crude product was purified via reverse phase HPLC (eluent: CH$_3$CN in water containing 0.1% TFA) to yield 20 mg (4.1%) of title compound 9-(8-aza-bicyclo[3.2.1]oct-3-yl)-6-pyridin-3-yl-9H-xanthen-4-ol, 8k as a TFA salt. MS m/z (MH$^+$) 385.2.

9-(8-Furan-3-ylmethyl-8-aza-bicyclo[3.2.1]oct-3-yl)-6-pyridin-3-yl-9H-xanthen-4-ol, 9k Using an adaptation of the method described in Procedure 12, substituting the TFA salt of 9-(8-aza-bicyclo[3.2.1]oct-3-yl)-6-pyridin-3-yl-9H-xanthen-4-ol, 8k for 3-(3-pyridin-3-yl-9H-xanthen-9-yl)-8-aza-bicyclo[3.2.1]octane, 3b, title compound 9-(8-furan-3-ylmethyl-8-aza-bicyclo[3.2.1]oct-3-yl)-6-pyridin-3-yl-9H-xanthen-4-ol, 9k was obtained as a TFA salt. MS m/z (MH$^+$) 465.1.

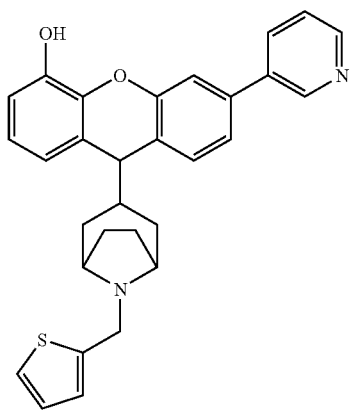

6-Pyridin-3-yl-9-(8-thiophen-2-ylmethyl-8-aza-bicyclo[3.2.1]oct-3-yl)-9H-xanthen-4-ol, 10k Using an adaptation of the method described in Procedure 12, substituting the TFA salt of 9-(8-aza-bicyclo[3.2.1]oct-3-yl)-6-pyridin-3-yl-9H-xanthen-4-ol, 8k for 3-(3-pyridin-3-yl-9H-xanthen-9-yl)-8-aza-bicyclo[3.2.1]octane, 3b and 2-thiophene carboxaldehyde for 3-furaldehyde, title compound 6-pyridin-3-yl-9-(8-thiophen-2-ylmethyl-8-aza-bicyclo[3.2.1]oct-3-yl)-9H-xanthen-4-ol, 10k was obtained as a TFA salt. MS m/z (MH$^+$) 481.1.

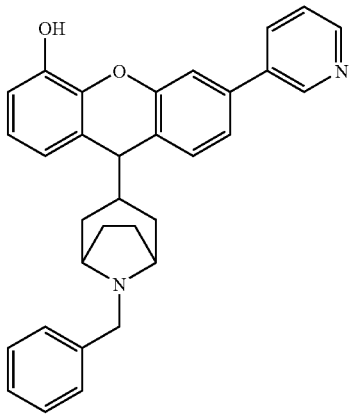

9-(8-Benzyl-8-aza-bicyclo[3.2.1]oct-3-yl)-6-pyridin-3-yl-9H-xanthen-4-ol, 12k

Using an adaptation of the method described in Procedure 12, substituting the TFA salt of 9-(8-aza-bicyclo[3.2.1]oct-3-yl)-6-pyridin-3-yl-9H-xanthen-4-ol, 8k for 3-(3-pyridin-3-yl-9H-xanthen-9-yl)-8-aza-bicyclo[3.2.1]octane, 3b and benzaldehyde for 3-furaldehyde, title compound 9-(8-benzyl-8-aza-bicyclo[3.2.1]oct-3-yl)-6-pyridin-3-yl-9H-xanthen-4-ol, 12k was obtained as a TFA salt. MS m/z (MH$^+$) 475.1.

6-Pyridin-3-yl-9-(8-pyridin-2-ylmethyl-8-aza-bicyclo[3.2.1]oct-3-yl)-9H-xanthen-4-ol, 11k Using an adaptation of the method described in Procedure 12, substituting the TFA salt of 9-(8-aza-bicyclo[3.2.1]oct-3-yl)-6-pyridin-3-yl-9H-xanthen-4-ol, 8k for 3-(3-pyridin-3-yl-9H-xanthen-9-yl)-8-aza-bicyclo[3.2.1]octane, 3b and 2-pyridyl carboxaldehyde for 3-furaldehyde, title compound 6-pyridin-3-yl-9-(8-pyridin-2-ylmethyl-8-aza-bicyclo[3.2.1]oct-3-yl)-9H-xanthen-4-ol, 11k was obtained as a TFA salt. MS m/z (MH$^+$) 476.1.

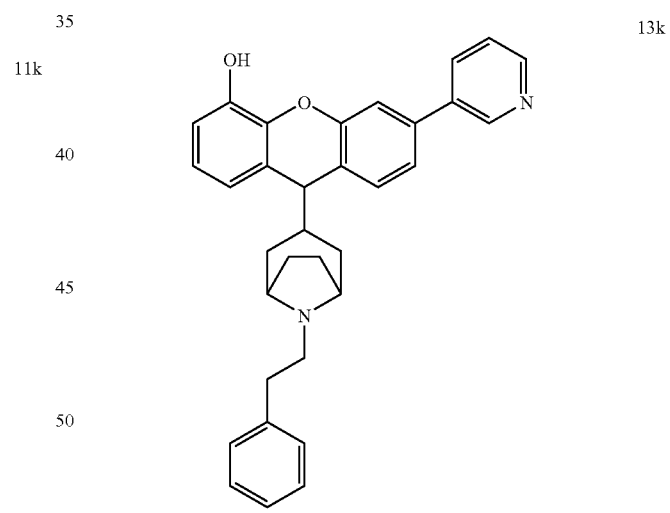

9-(8-Phenethyl-8-aza-bicyclo[3.2.1]oct-3-yl)-6-pyridin-3-yl-9H-xanthen-4-ol, 13k Using an adaptation of the method described in Procedure 12, substituting the TFA salt of 9-(8-aza-bicyclo[3.2.1]oct-3-yl)-6-pyridin-3-yl-9H-xanthen-4-ol, 8k for 3-(3-pyridin-3-yl-9H-xanthen-9-yl)-8-aza-bicyclo[3.2.1]octane, 3b and phenyl acetaldehyde for 37furaldehyde, title compound 9-(8-phenethyl-8-aza-bicyclo[3.2.1]oct-3-yl)-6-pyridin-3-yl-9H-xanthen-4-ol, 13k was obtained as a TFA salt. MS m/z (MH$^+$) 489.1.

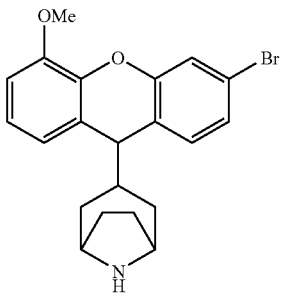

14k

3-(3-Bromo-5-methoxy-9H-xanthen-9-yl)-8-aza-bicyclo[3.2.1]octane, 14k

Using an adaptation of the method described in Procedure 23, substituting 1-[3-(3-bromo-5-methoxy-9H-xanthen-9-yl)-8-aza-bicyclo[3.2.1]oct-8-yl]-2,2,2-trifluoro-ethanone, 5k for 2,2,2-trifluoro-1-{3-[3-(1H-tetrazol-5-yl)-9H-xanthen-9-yl]-8-aza-bicyclo[3.2.1]oct-8-yl}-ethanone, 4j, the title compound 3-(3-bromo-5-methoxy-9H-xanthen-9-yl)-8-aza-bicyclo[3.2.1]octane, 14k was obtained as a TFA salt. MS m/z (MH$^+$) 400.2.

Example L

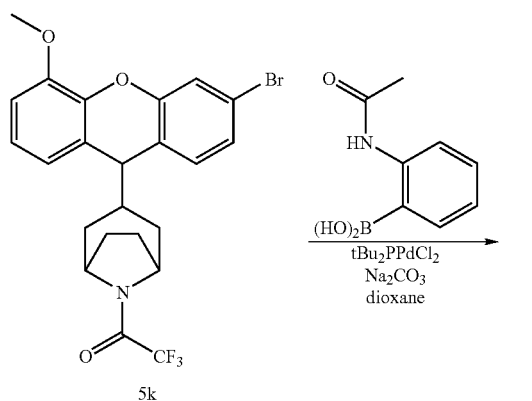

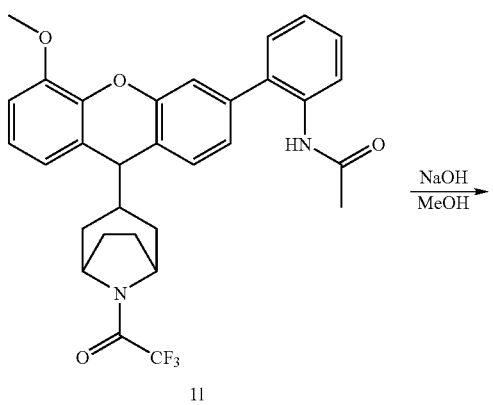

11

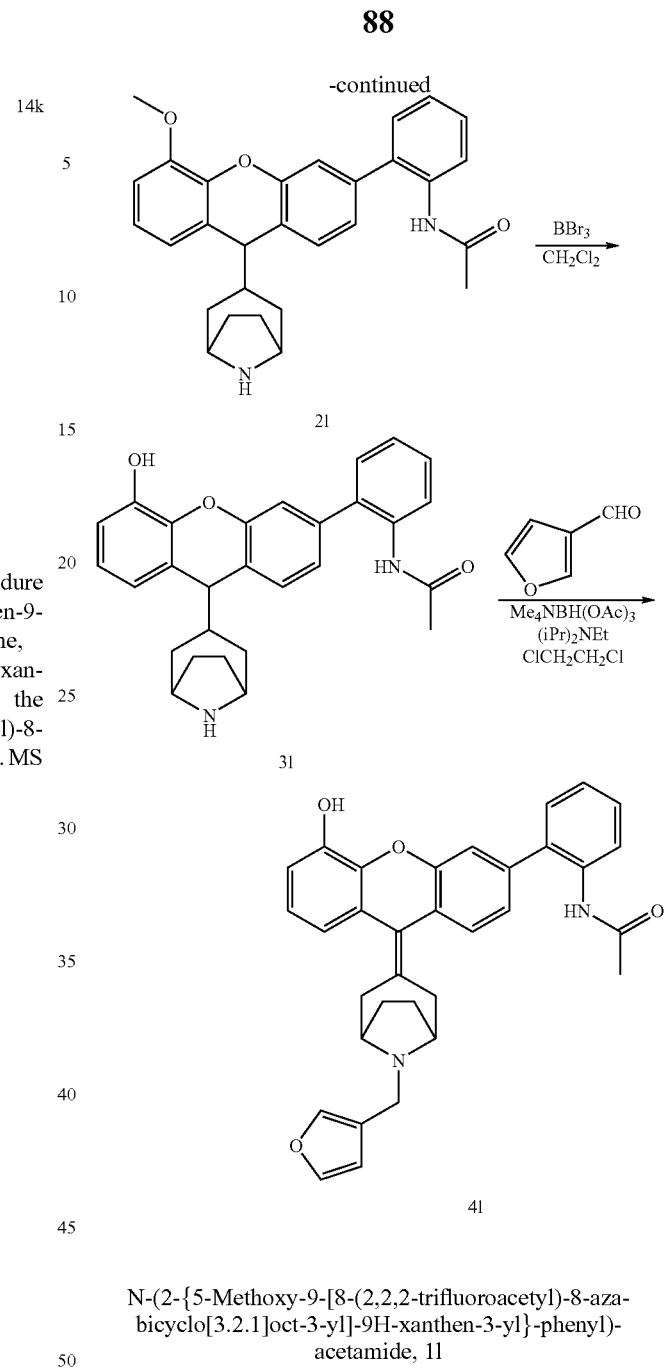

N-(2-{5-Methoxy-9-[8-(2,2,2-trifluoroacetyl)-8-aza-bicyclo[3.2.1]oct-3-yl]-9H-xanthen-3-yl}-phenyl)-acetamide, 1l Using an adaptation of the method described in Procedure 24, substituting 2-acetylaminophenyl boronic acid for 3-pyridylboronic acid, the title compound N-(2-{5-methoxy-9-[8-(2,2,2-trifluoroacetyl)-8-aza-bicyclo[3.2.1]oct-3-yl]-9H-xanthen-3-yl}-phenyl)-acetamide, 1l was obtained. MS m/z (MH$^+$) 550.1.

N-{2-[9-(8-Aza-bicyclo[3.2.1]oct-3-yl)-5-methoxy-9H-xanthen-3-yl]-phenyl}-acetamide, 2l Using an adaptation of the method described in Procedure 23, substituting N-(2-{5-methoxy-9-[8-(2,2,2-trifluoroacetyl)-8-aza-bicyclo[3.2.1]oct-3-yl]-9H-xanthen-3-yl}-phenyl)-acetamide, 1l for 2,2,2-trifluoro-1-{3-[3-(1H-tetrazol-5-yl)-9H-xanthen-9-yl]-8-aza-bicyclo[3.2.1]oct-8-yl}-ethanone, 4j, the title compound N-{2-[9-(8-aza-bicyclo

[3.2.1]oct-3-yl)-5-methoxy-9H-xanthen-3-yl]-phenyl}-acetamide, 2l was obtained as a TFA salt. MS m/z (MH+) 455.1.

N-{2-[9-(8-Aza-bicyclo[3.2.1]oct-3-yl)-5-hydroxy-9H-xanthen-3-yl]-phenyl}-acetamide, 3l Using an adaptation of the method described in Procedure 25, substituting N-{2-[9-(8-aza-bicyclo[3.2.1]oct-3-yl)-5-methoxy-9H-xanthen-3-yl]-phenyl}-acetamide, 2l for 3-(5-methoxy-3-pyridin-3-yl-9H-xanthen-9-yl)-8-aza-bicyclo[3.2.1]octane, 7k, the title compound N-{2-[9-(8-aza-bicyclo[3.2.1]oct-3-yl)-5-hydroxy-9H-xanthen-3-yl]-phenyl}-acetamide, 3l was obtained as a TFA salt. MS m/z (MH+) 441.1.

N-{2-[9-(8-Furan-3-ylmethyl-8-aza-bicyclo[3.2.1]oct-3-yl)-5-hydroxy-9H-xanthen-3-yl]-phenyl}-acetamide, 4l Using an adaptation of the method described in Procedure 12, substituting the TFA salt of N-{2-[9-(8-aza-bicyclo[3.2.1]oct-3-yl)-5-hydroxy-9H-xanthen-3-yl]-phenyl}-acetamide, 3l for 3-(3-pyridin-3-yl-9H-xanthen-9-yl)-8-aza-bicyclo[3.2.1]octane, 3b, title compound N-{2-[9-(8-furan-3-ylmethyl-8-aza-bicyclo[3.2.1]oct-3-yl)-5-hydroxy-9H-xanthen-3-yl]-phenyl}-acetamide, 4l was obtained as a TFA salt. MS m/z (MH+) 521.3.

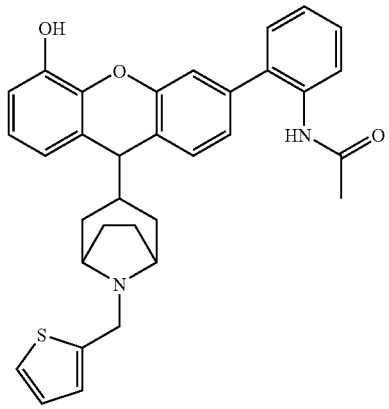

N-{2-[5-Hydroxy-9-(8-thiophen-2-ylmethyl-8-aza-bicyclo[3.2.1]oct-3-yl)-9H-xanthen-3-yl]-phenyl}-acetamide, 5l Using an adaptation of the method described in Procedure 12, substituting the TFA salt of N-{2-[9-(8-aza-bicyclo[3.2.1]oct-3-yl)-5-hydroxy-9H-xanthen-3-yl]-phenyl}-acetamide,3l for 3-(3-pyridin-3-yl-9H-xanthen-9-yl)-8-aza-bicyclo[3.2.1]octane, 3b, and 2-thiophene carboxaldehyde for 3-furaldehyde, title compound N-{2-[5-hydroxy-9-(8-thiophen-2-ylmethyl-8-aza-bicyclo-[3.2.1]oct-3-yl)-9H-xanthen-3-yl]-phenyl}-acetamide, 5l was obtained as a TFA salt. MS m/z (MH+) 537.3.

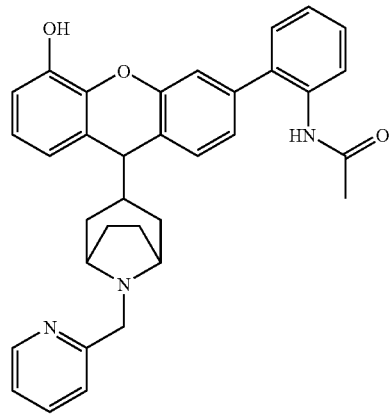

N-{2-[5-Hydroxy-9-(8-pyridin-2-ylmethyl-8-aza-bicyclo[3.2.1]oct-3-yl)-9H-xanthen-3-yl]-phenyl}-acetamide, 6l Using an adaptation of the method described in Procedure 12, substituting the TFA salt of N-{2-[9-(8-aza-bicyclo[3.2.1]oct-3-yl)-5-hydroxy-9H-xanthen-3-yl]-phenyl}-acetamide, 3l for 3-(3-pyridin-3-yl-9H-xanthen-9-yl)-8-aza-bicyclo[3.2.1]octane, 3b, and 2-pyridyl carboxaldehyde for 3-furaldehyde, title compound N-{2-[5-hydroxy-9-(8-pyridin-2-ylmethyl-8-aza-bicyclo[3.2.1]oct-3-yl)-9H-xanthen-3-yl]-phenyl}-acetamide, 6l was obtained as a TFA salt. MS m/z (MH+) 532.2.

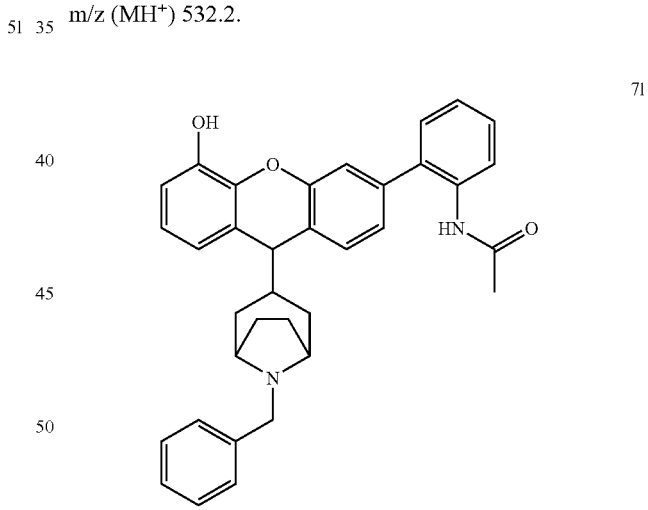

N-{2-[9-(8-Benzyl-8-aza-bicyclo[3.2.1]oct-3-yl)-5-hydroxy-9H-xanthen-3-yl]-phenyl}-acetamide, 7l Using an adaptation of the method described in Procedure 12, substituting the TFA salt of N-{2-[9-(8-aza-bicyclo[3.2.1]oct-3-yl)-5-hydroxy-9H-xanthen-3-yl]-phenyl}-acetamide, 3l for 3-(3-pyridin-3-yl-9H-xanthen-9-yl)-8-aza-bicyclo[3.2.1]octane, 3b, and benzaldehyde for 3-furaldehyde, title compound N-{2-[9-(8-benzyl-8-aza-bicyclo[3.2.1]oct-3-yl )-5-hydroxy-9H-xanthen-3-yl]-phenyl}-acetamide, 7l was obtained as a TFA salt. MS m/z (MH+) 531.3.

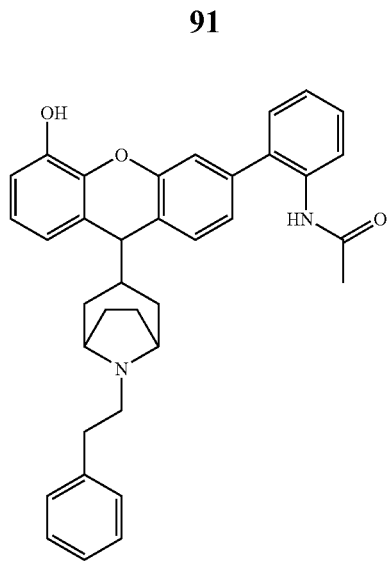

N-{2-[5-Hydroxy-9-(8-phenethyl-8-aza-bicyclo
[3.2.1]oct-3-yl)-9H-xanthen-3-yl]-phenyl}-acetamide, 8l Using an adaptation of the method described in Procedure 12, substituting the TFA salt of N-{2-[9-(8-aza-bicyclo[3.2.1]oct-3-yl)-5-hydroxy-9H-xanthen-3-yl]-phenyl}-acetamide, 3l for 3-(3-pyridin-3-yl-9H-xanthen-9-yl)-8-aza-bicyclo[3.2.1]octane, 3b, and phenyl acetaldehyde for 3-furaldehyde, title compound N-{2-[5-hydroxy-9-(8-phenethyl-8-aza-bicyclo[3.2.1]oct-3-yl)-9H-xanthen-3-yl]-phenyl}-acetamide, 8l was obtained as a TFA salt. MS m/z (MH$^+$) 545.3.

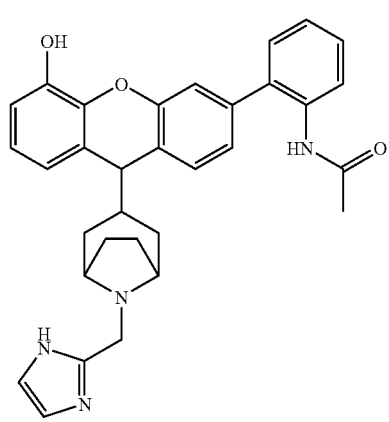

N-(2-{5-Hydroxy-9-[8-(1H-imidazol-2-ylmethyl)-8-aza-bicyclo[3.2.1]oct-3-yl]-9H-xanthen-3-yl}-phenyl)-acetamide, 9l Using an adaptation of the method described in Procedure 12, substituting the TFA salt of N-{2-[9-(8-aza-bicyclo[3.2.1]oct-3-yl)-5-hydroxy-9H-xanthen-3-yl]-phenyl}-acetamide, 3l for 3-(3-pyridin-3-yl-9H-xanthen-9-yl)-8-aza-bicyclo[3.2.1]octane, 3b, and 1H-imidazole-2-carboxaldehyde for 3-furaldehyde, title compound N-(2-{5-hydroxy-9-[8-(1H-imidazol-2-ylmethyl)-8-aza-bicyclo[3.2.1]oct-3-yl]-9H-xanthen-3-yl}-phenyl)-acetamide, 9l was obtained as a TFA salt. MS m/z (MH$^+$) 521.0.

Example M

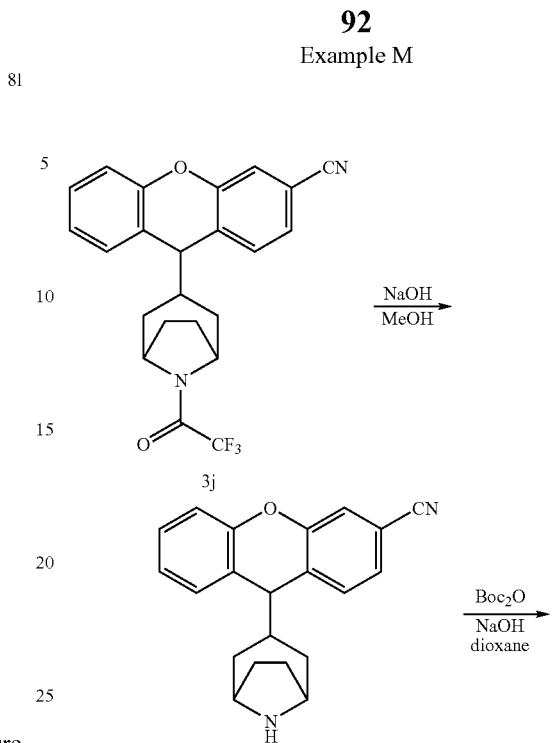

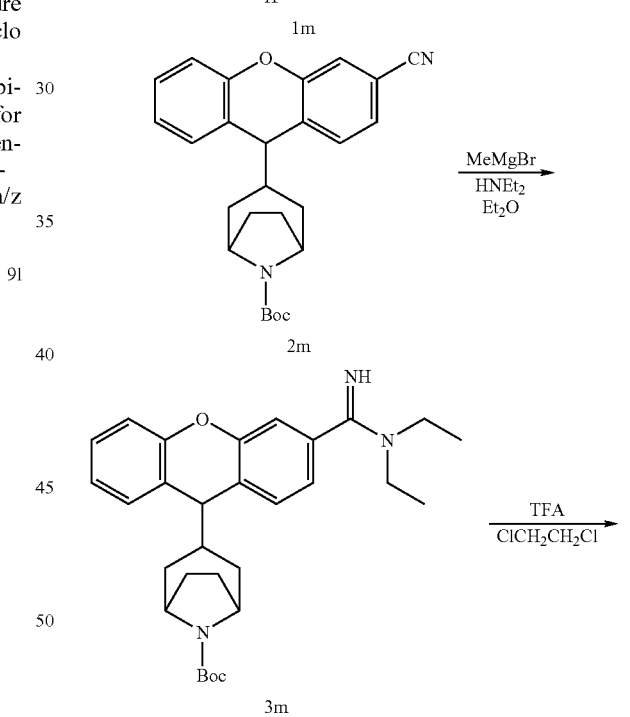

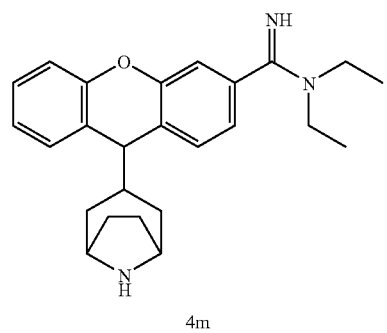

9-(8-Aza-bicyclo[3.2.1]oct-3-yl)-9H-xanthene-3-carbonitrile, 1m

Using an adaptation of the method described in Procedure 23, substituting 9-[8-(2,2,2-trifluoroacetyl)-8-aza-bicyclo[3.2.1]oct-3-yl]-9H-xanthene-3-carbonitrile, 3j for 2,2,2-trifluoro-1-{3-[3-(1H-tetrazol-5-yl)-9H-xanthen-9-yl]-8-aza-bicyclo-[3.2.1]oct-8-yl}-ethanone, 4j, the title compound 9-(8-aza-bicyclo[3.2.1]oct-3-yl)-9H-xanthene-3-carbonitrile, 1m was obtained.

Procedure 26

3-(3-Cyano-9H-xanthen-9-yl)-8-aza-bicyclo[3.2.1]octane-8-carboxylic acid tert-butyl ester, 2m To a solution of 9-(8-aza-bicyclo[3.2.1]oct-3-yl)-9H-xanthene-3-carbonitrile, 1m (0.48 g, 1.52 mmol) in methylene chloride was added Boc anhydride (0.365 g, 1.67 mmol), and the mixture was stirred at rt for 16 h. The mixture was washed with water, and the organic was separated, dired over $Na_2SO_4$, filtered, and evaporated, yielding 0.643 g, quant.) of crude 3-(3-cyano-9H-xanthen-9-yl)-8-aza-bicyclo[3.2.1]octane-8-carboxylic acid tert-butyl ester, 2m. The material was used as such in the next reaction.

Procedure 27

3-[3-(N,N-Diethyl-carbamimidoyl)-9H-xanthen-9-yl]-8-aza-bicyclo[3.2.1]octane-8-carboxylic acid tert-butyl ester, 3m To a solution of methylmagnesium bromide in diethyl ether (3.0 M, 0.77 mL) under a $N_2$ atmosphere was added dropwise a solution of diethylamine (0.238 mL; 2.3 mmol) in diethyl ether (10 mL). The mixture was heated to reflux for 30 min and allowed to cool to rt. A suspension of 4-(3-cyanophenoxazin-10-yl)-piperidine-1-carboxylic acid tert-butyl ester, 4a (1 g; 0.77 mmol) in diethyl ether (10 mL) was added, and the mixture was heated to reflux for 2 h. Water was added, and the organic layer was separated. The aqueous layer was extracted with ethyl acetate (2×10 mL), and the combined organic layers were dried over $Na_2SO_4$, filtered, and evaporated, yielding crude 3-[3-(N,N-diethyl-carbamimidoyl)-9H-xanthen-9-yl]-8-aza-bicyclo[3.2.1]octane-8-carboxylic acid tert-butyl ester, 3m. The residue was used as such for the next reaction.

Procedure 28

9-(8-Aza-bicyclo[3.2.1]oct-3-yl)-N,N-diethyl-9H-xanthene-3-carboxamidine, 4m To solution of crude 3-[3-(N,N-diethyl-carbamimidoyl)-9H-xanthen-9-yl]-8-aza-bicyclo[3.2.1]octane-8-carboxylic acid tert-butyl ester, 3m (0.34 g) in dichloroethane (2 mL) was added $H_2O$ (0.1 mL) and TFA (2 mL). The mixture was stirred at rt for 1 h and evaporated. The residue was purified via reverse phase HPLC (eluent: $CH_3CN$ in water containing 0.1% TFA), yielding 0.263 g (56%) for two steps) of 9-(8-aza-bicyclo[3.2.1]oct-3-yl)-N,N-diethyl-9H-xanthene-3-carboxamidine, 4m as a TFA salt (MS m/z ($MH^+$) 390.3.

N,N-Diethyl-9-(8-furan-3-ylmethyl-8-aza-bicyclo[3.2.1]oct-3-yl)-9H-xanthene-3-carboxamidine, 5m Using an adaptation of the method described in Procedure 10, substituting the TFA salt of 9-(8-aza-bicyclo[3.2.1]oct-3-yl)-N,N-diethyl-9H-xanthene-3-carboxamidine, 4m for 9-(8-aza-bicyclo[3.2.1]oct-3-yl)-9H-xanthene-3-carboxylic acid diethylamide, 9a, the title compound N,N-diethyl-9-(8-furan-3-ylmethyl-8-aza-bicyclo[3.2.1]oct-3-yl)-9H-xanthene-3-carboxamidine, 5m was obtained as a TFA salt after purification via reverse phase HPLC (eluent: $CH_3CN$ in $H_2O$ containing 0.1% TFA). MS mlz ($MH^+$) 470.1.

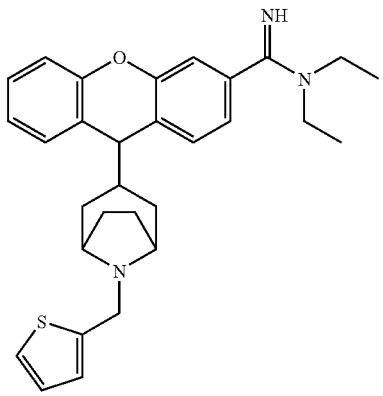

6m

N,N-Diethyl-9-(8-thiophen-2-ylmethyl-8-aza-bicyclo[3.2.1]oct-3-yl)-9H-xanthene-3-carboxamidine, 6m Using an adaptation of the method described in Procedure 10, substituting the TFA salt of 9-(8-aza-bicyclo[3.2.1]oct-3-yl)-N,N-diethyl-9H-xanthene-3-carboxamidine, 4m for 9-(8-aza-bicyclo[3.2.1]oct-3-yl)-9H-xanthene-3-carboxylic acid diethylamide, 9a, and thiophene-2-carboxaldehyde for furan-3-carboxaldehyde, the title compound N,N-diethyl-9-(8-thiophen-2-ylmethyl-8-aza-bicyclo[3.2.1]oct-3-yl)-9H-xanthene-3-carboxamidine, 6m was obtained as a TFA salt after purification via reverse phase HPLC (eluent: $CH_3CN$ in $H_2O$ containing 0.1% TFA). MS m/z ($MH^+$) 486.1.

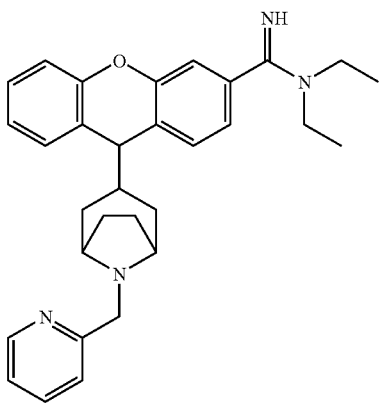

7m

N,N-Diethyl-9-(8-pyridin-2-ylmethyl-8-aza-bicyclo[3.2.1]oct-3-yl)-9H-xanthene-3-carboxamidine, 7m Using an adaptation of the method described in Procedure 10, substituting the TFA salt of 9-(8-aza-bicyclo[3.2.1]oct-3-yl)-N,N-diethyl-9H-xanthene-3-carboxamidine, 4m for 9-(8-aza-bicyclo[3.2.1]oct-3-yl)-9H-xanthene-3-carboxylic acid diethylamide, 9a, and pyridyl-2-carboxaldehyde for furan-3-carboxaldehyde, the title compound N,N-diethyl-9-(8-pyridin-2-ylmethyl-8-aza-bicyclo[3.2.1]oct-3-yl)-9H-xanthene-3-carboxamidine, 7m was obtained as a TFA salt after purification via reverse phase HPLC (eluent: $CH_3CN$ in $H_2O$ containing 0.1% TFA). MS m/z ($MH^+$) 481.3.

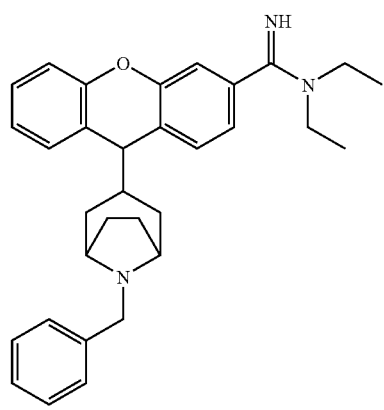

8m

9-(8-Benzyl-8-aza-bicyclo[3.2.1]oct-3-yl)-N,N-diethyl-9H-xanthene-3-carboxamidine, 8m Using an adaptation of the method described in Procedure 10, substituting the TFA salt of 9-(8-aza-bicyclo[3.2.1]oct-3-yl)-N,N-diethyl-9H-xanthene-3-carboxamidine, 4m for 9-(8-aza-bicyclo[3.2.1]oct-3-yl)-9H-xanthene-3-carboxylic acid diethylamide, 9a, and benzaldehyde for furan-3-carboxaldehyde, the title compound 9-(8-benzyl-8-aza-bicyclo[3.2.1]oct-3-yl)-N,N-diethyl-9H-xanthene-3-carboxamidine, 8m was obtained as a TFA salt after purification via reverse phase HPLC (eluent: $CH_3CN$ in $H_2O$ containing 0.1% TFA). MS m/z ($MH^+$) 480.2.

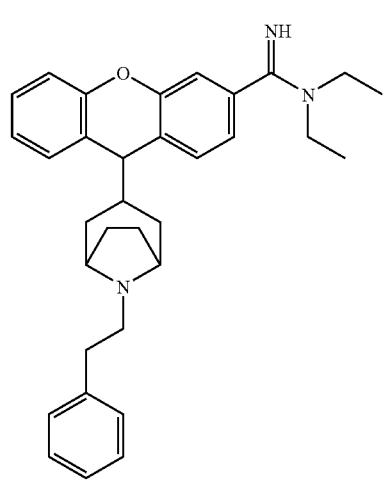

9m

N,N-Diethyl-9-(8-phenethyl-8-aza-bicyclo[3.2.1]oct-3-yl)-9H-xanthene-3-carboxamidine, 9m Using an adaptation of the method described in Procedure 10, substituting the TFA salt of 9-(8-aza-bicyclo[3.2.1]oct-3-yl)-N,N-diethyl-9H-xanthene-3-carboxamidine, 4m for 9-(8-aza-bicyclo[3.2.1]oct-3-yl)-9H-xanthene-3-carboxylic acid diethylamide, 9a, and phenyl acetaldehyde for furan-3-carboxaldehyde, the title compound N,N-diethyl-9-(8-phenethyl-8-aza-bicyclo[3.2.1]oct-3-yl)-9H-xanthene-3-carboxamidine, 9m was obtained as a TFA salt after purification via reverse phase HPLC (eluent: $CH_3CN$ in $H_2O$ containing 0.1% TFA). MS m/z ($MH^+$) 480.2.

Example N

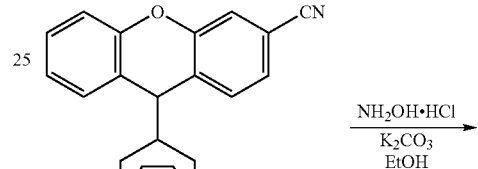

2m

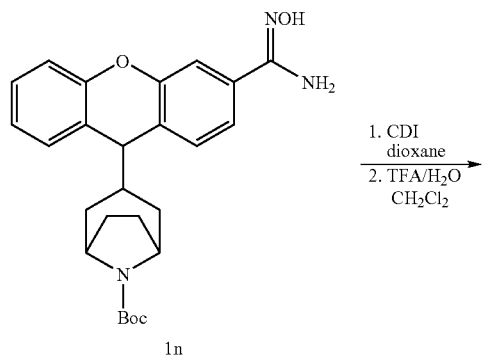

1n

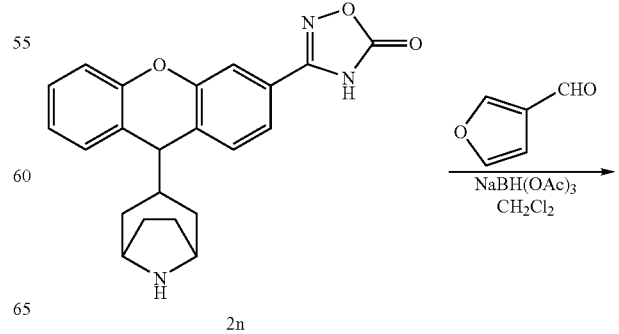

2n

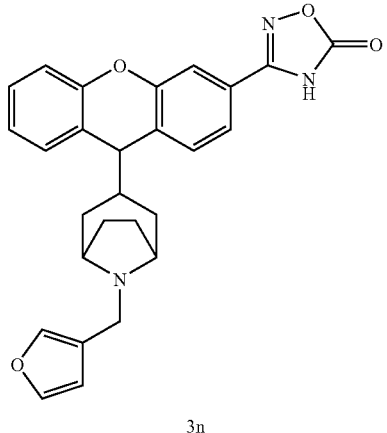

3n

Procedure 29

3-[3-(N-Hydroxycarbamimidoyl)-9H-xanthen-9-yl]-8-aza-bicyclo[3.2.1]octane-8-carboxylic acid tert-butyl ester, 1n To a solution of 3-(3-cyano-9H-xanthen-9-yl)-8-aza-bicyclo[3.2.1]octane-8-carboxylic acid tert-butyl ester (635 mg; 0.877 mmol) in ethanol (10 mL) was added hydroxylamine hydrochloride (183 mg; 2.62 mmol) and potassium carbonate (242 mg; 1.75 mmol), and the mixture was heated to reflux for 16 h. More ammonium hydroxide hydrochloride (183 mg; 2.62 mmol) and potassium carbonate (242 mg; 1.75 mmol) were added, and the mixture was heated to reflux for 24 h. The mixture was allowed to cool to rt, water was added, and the solid was collected by filtration, yielding 402 mg (quant.) of 3-[3-(N-hydroxycarbamimidoyl)-9H-xanthen-9-yl]-8-aza-bicyclo[3.2.1]octane-8-carboxylic acid tert-butyl ester, 1n. The crude material was used as such in the next reaction.

Procedure 30

3-(9-Piperidin-4-yl-9H-xanthen-3-yl)-4H-[1,2,4]oxadiazol-5-one, 2n

To a solution of 3-[3-(N-hydroxycarbamimidoyl)-9H-xanthen-9-yl]-8-aza-bicyclo[3.2.1]octane-8-carboxylic acid tert-butyl ester, 1n (0.402 g; 0.894 mmol) in dioxane (10 mL) was added 1,1'-carbonyldiimidazole (217 mg; 1.34 mmol), and the mixture was stirred at 110° C. for 16 h. More 1,1'-carbonyldiimidazole (217 mg; 1.34 mmol) was added, and the mixture was heated to reflux for 24 h. The mixture was evaporated and treated with water. The solid was collected via filtration, yielding crude Boc-protected 3-(10-piperidin-4-yl-10H-phenoxazin-3-yl)-4H-[1,2,4]oxadiazol-5-one, 2b. The material was dissolved in methylene chloride (5 mL) and treated with water (0.1 mL) and TFA (5 mL). The mixture was stirred at rt for 1 h, evaporated, and purified via reverse phase HPLC (eluent: CH$_3$CN in H$_2$O containing 0.1% TFA), yielding 0.18 g (41% for two steps) of 3-(9-piperidin-4-yl-9H-xanthen-3-yl)-4H-[1,2,4]oxadiazol-5-one, 2n as a TFA salt. MS m/z (MH$^+$) 376.0.

3-[9-(1-Furan-3-ylmethyl-piperidin-4-yl)-9H-xanthen-3-yl]-4H-[1,2,4]oxadiazol-5-one, 3n Using an adaptation of the method described in Procedure 10, substituting the TFA salt of 3-(9-piperidin-4-yl-9H-xanthen-3-yl)-4H-[1,2,4]oxadiazol-5-one, 2n for 9-(8-aza-bicyclo[3.2.1]oct-3-yl)-9H-xanthene-3-carboxylic acid diethylamide, 9a, the title compound 3-[9-(1-furan-3-ylmethyl-piperidin-4-yl)-9H-xanthen-3-yl]-4H-[1,2,4]oxadiazol-5-one, 3n was obtained as a TFA salt after purification via reverse phase HPLC (eluent: CH$_3$CN in H$_2$O containing 0.1% TFA). MS m/z (MH$^+$) 455.9.

3-[9-(8-Pyridin-2-ylmethyl-8-aza-bicyclo[3.2.1]oct-3-yl)-9H-xanthen-3-yl]-4H-[1,2,4]oxadiazol-5-one, 4n Using an adaptation of the method described in Procedure 10, substituting the TFA salt of 3-(9-piperidin-4-yl-9H-xanthen-3-yl)-4H-[1,2,4]oxadiazol-5-one, 2n for 9-(8-aza-bicyclo[3.2.1]oct-3-yl)-9H-xanthene-3-carboxylic acid diethylamide, 9a, and pyridyl-2-carboxaldehyde for furan-3-carboxaldehyde, the title compound 3-[9-(8-pyridin-2-ylmethyl-8-aza-bicyclo[3.2.1]oct-3-yl)-9H-xanthen-3-yl]-4H-[1,2,4]oxadiazol-5-one, 4n was obtained as a TFA salt after purification via reverse phase HPLC (eluent: CH$_3$CN in H$_2$O containing 0.1% TFA). MS m/z (MH$^+$) 466.9.

Example O

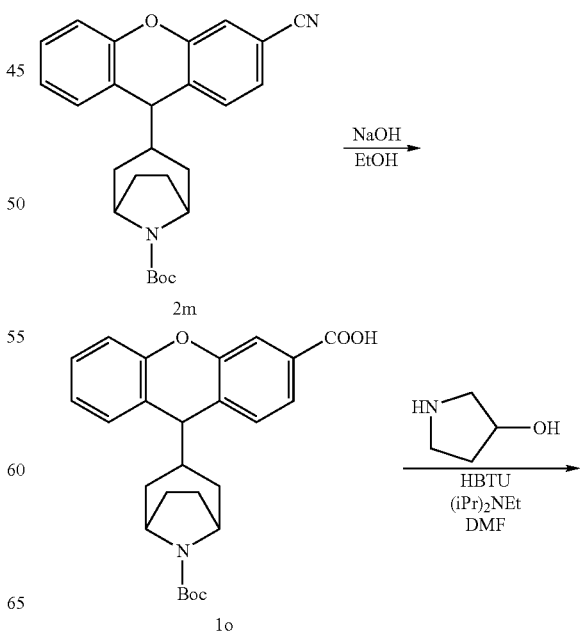

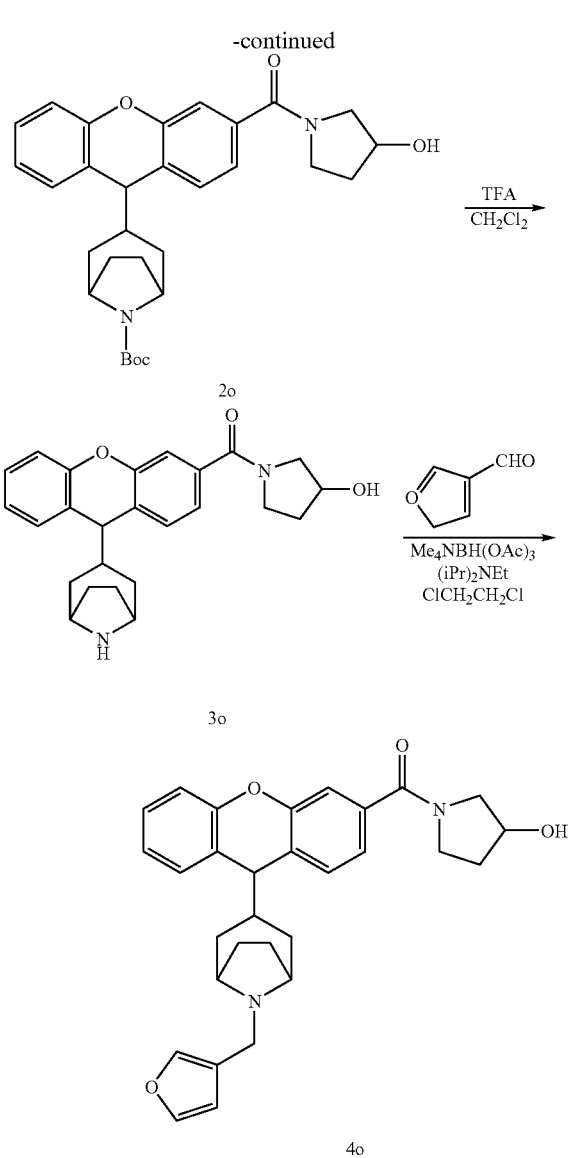

clo[3.2.1]octane-8-carboxylic acid tert-butyl ester, 1o, for 5-methoxy-9-oxo-9H-xanthene-3-carboxylic acid, 3c, and 3-hydroxypyrrolidine for N,N-diethylamine, title compound 3-[3-(3-hydroxy-pyrrolidine-1-carbonyl)-9H-xanthen-9-yl]-8-aza-bicyclo[3.2.1]octane-8-carboxylic acid tert-butyl ester, 2o was obtained.

[9-(8-Aza-bicyclo[3.2.1]oct-3-yl)-9H-xanthen-3-yl]-(3-hydroxy-pyrrolidin-1-yl)-methanone, 3o Using an adaptation of the method described in Procedure 28, substituting 3-[3-(3-hydroxy-pyrrolidine-1-carbonyl)-9H-xanthen-9-yl]-8-aza-bicyclo[3.2.1]octane-8-carboxylic acid tert-butyl ester, 2o for 3-[3-(N,N-diethyl-carbamimidoyl)-9H-xanthen-9-yl]-8-aza-bicyclo[3.2.1]octane-8-carboxylic acid tert-butyl ester, 3m, the title compound [9-(8-aza-bicyclo[3.2.1]oct-3-yl)-9H-xanthen-3-yl]-(3-hydroxy-pyrrolidin-1-yl)-methanone, 3o was obtained as a TFA salt after purification via reverse phase HPLC (eluent: $CH_3CN$ in $H_2O$ containing 0.1% TFA). MS m/z ($MH^+$) 405.0.

[9-(8-Furan-3-ylmethyl-8-aza-bicyclo[3.2.1]oct-3-yl)-9H-xanthen-3-yl]-(3-hydroxy-pyrrolidin-1-yl)-methanone, 4o Using an adaptation of the method described in Procedure 10, substituting the TFA salt of [9-(8-aza-bicyclo[3.2.1]oct-3-yl)-9H-xanthen-3-yl]-(3-hydroxy-pyrrolidin-1-yl)-methanone, 3o for 9-(8-aza-bicyclo[3.2.1]oct-3-yl)-9H-xanthene-3-carboxylic acid diethylamide, 9a, the title compound [9-(8-furan-3-ylmethyl-8-aza-bicyclo[3.2.1]oct-3-yl)-9H-xanthen-3-yl]-(3-hydroxy-pyrrolidin-1-yl )-methanone, 4o was obtained as a TFA salt after purification via reverse phase HPLC (eluent: $CH_3CN$ in $H_2O$ containing 0.1% TFA). MS m/z ($MH^+$) 485.0.

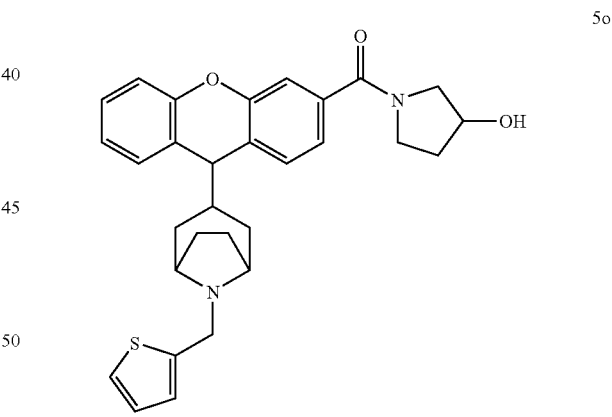

(3-Hydroxy-pyrrolidin-1-yl)-[9-(8-thiophen-2-ylmethyl-8-aza-bicyclo[3.2.1]oct-3-yl)-9H-xanthen-3-yl]-methanone, 5o

3-(3-Carboxy-9H-xanthen-9-yl)-8-aza-bicyclo[3.2.1]octane-8-carboxylic acid tert-butyl ester, 1o To a solution of 3-(3-cyano-9H-xanthen-9-yl)-8-aza-bicyclo[3.2.1]octane-8-carboxylic acid tert-butyl ester, 2m (1.8 g, 4.3 mmol) in ethanol was added a 20% aqueous sodium hydroxide solution (2 g). The mixture was heated to reflux for 16 h, allowed to cool to rt, and acidified with a 1N HCl solution. The mixture was extracted with methylene chloride, and the organic phase was dried over $MgSO_4$, filtered, and evaporated. The thus obtained crude title compound 3-(3-carboxy-9H-xanthen-9-yl)-8-aza-bicyclo[3.2.1]octane-8-carboxylic acid tert-butyl ester, 1o was used as such for the next reaction without further purification.

3-[3-(3-Hydroxy-pyrrolidine-1-carbonyl)-9H-xanthen-9-yl]-8-aza-bicyclo[3.2.1]octane-8-carboxylic acid tert-butyl ester, 2o Using an adaptation of the method described in Procedure 16, substituting 3-(3-carboxy-9H-xanthen-9- yl)-8-aza-bicy- Using an adaptation of the method described in Procedure 10, substituting the TFA salt of [9-(8-aza-bicyclo[3.2.1]oct-3-yl)-9H-xanthen-3-yl]-(3-hydroxy-pyrrolidin-1-yl)-methanone, 3o for 9-(8-aza-bicyclo[3.2.1]oct-3-yl)-9H-xanthene-3-carboxylic acid diethylamide, 9a, and thiophene-2-carboxaldehyde for furan-3-ylcarboxaldehyde, the title compound (3-hydroxy-pyrrolidin-1-yl)-[9-(8-thiophen-2-ylmethyl-8-aza-bicyclo[3.2.1]oct-3-yl)-9H-xanthen-3-yl]- methanone, 5o was obtained as a TFA salt after purification via reverse phase HPLC (eluent: CH$_3$CN in H$_2$O containing 0.1% TFA). MS m/z (MH$^+$) 500.9.

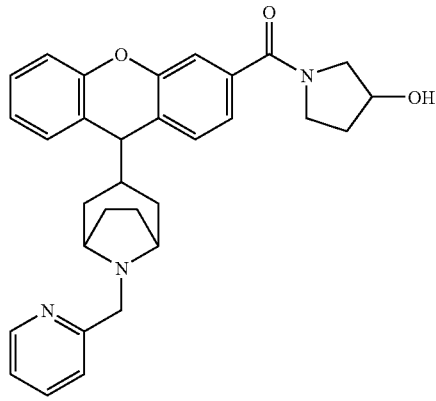

(3-Hydroxy-pyrrolidin-1-yl)-[9-(8-pyridin-2-ylmethyl-8-aza-bicyclo[3.2.1]oct-3-yl)-9H-xanthen-3-yl]-methanone, 6o Using an adaptation of the method described in Procedure 10, substituting the TFA salt of [9-(8-aza-bicyclo[3.2.1]oct-3-yl)-9H-xanthen-3-yl]-(3-hydroxy-pyrrolidin-1-yl)-methanone, 3o for 9-(8-aza-bicyclo[3.2.1]oct-3-yl)-9H-xanthene-3-carboxylic acid diethylamide, 9a, and pyridyl-2-carboxaldehyde for furan-3-ylcarboxaldehyde, the title compound (3-hydroxy-pyrrolidin-1-yl)-[9-(8-pyridin-2-ylmethyl-8-aza-bicyclo[3.2.1]oct-3-yl)-9H-xanthen-3-yl]-methanone, 6o was obtained as a TFA salt after purification via reverse phase HPLC (eluent: CH$_3$CN in H$_2$O containing 0.1% TFA). MS m/z (MH$^+$) 495.9.

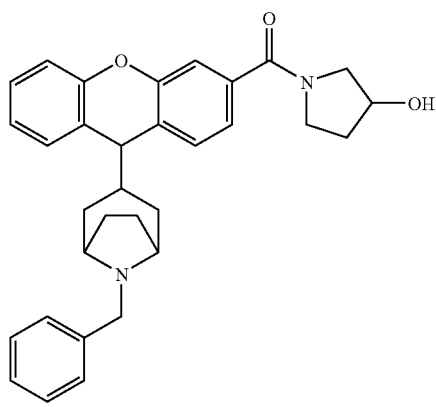

[9-(8-Benzyl-8-aza-bicyclo[3.2.1]oct-3-yl)-9H-xanthen-3-yl]-(3-hydroxy-pyrrolidin-1-yl)-methanone, 7o Using an adaptation of the method described in Procedure 10, substituting the TFA salt of [9-(8-aza-bicyclo[3.2.1]oct-3-yl)-9H-xanthen-3-yl]-(3-hydroxy-pyrrolidin-1-yl)-methanone, 3o for 9-(8-aza-bicyclo[3.2.1]oct-3-yl)-9H-xanthene-3-carboxylic acid diethylamide, 9a, and benzaldehyde for furan-3-ylcarboxaldehyde, the title compound [9-(8-benzyl-8-aza-bicyclo[3.2.1]oct-3-yl)-9H-xanthen-3-yl]-(3-hydroxy-pyrrolidin-1-yl)-methanone, 7o was obtained as a TFA salt after purification via reverse phase HPLC (eluent: CH$_3$CN in H$_2$O containing 0.1% TFA). MS m/z(MH$^+$)494.9.

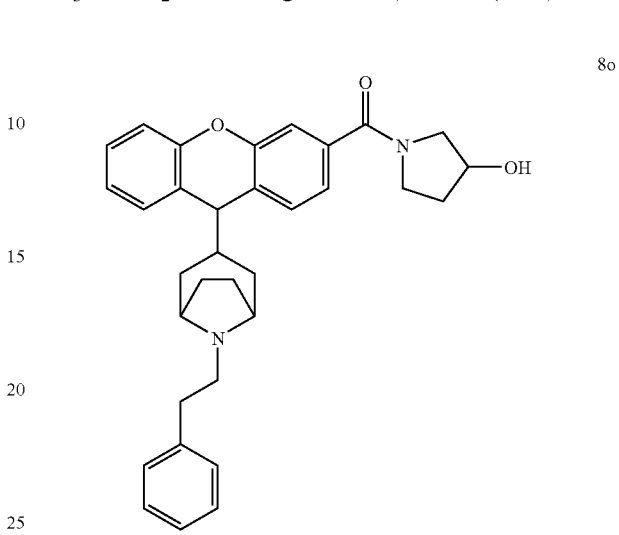

(3-Hydroxy-pyrrolidin-1-yl)-[9-(8-phenethyl-8-aza-bicyclo[3.2.1]oct-3-yl)-9H-xanthen-3-yl]-methanone, 8o Using an adaptation of the method described in Procedure 10, substituting the TFA salt of [9-(8-aza-bicyclo[3.2.1]oct-3-yl)-9H-xanthen-3-yl]-(3-hydroxy-pyrrolidin-1-yl)-methanone, 3o for 9-(8-aza-bicyclo[3.2.1]oct-3-yl)-9H-xanthene-3-carboxylic acid diethylamide, 9a, and phenyl acetaldehyde for furan-3-ylcarboxaldehyde, the title compound (3-hydroxy-pyrrolidin-1-yl)-[9-(8-phenethyl-8-aza-bicyclo[3.2.1]oct-3-yl)-9H-xanthen-3-yl]-methanone, 8o was obtained as a TFA salt after purification via reverse phase HPLC (eluent: CH$_3$CN in H$_2$O containing 0.1% TFA). MS m/z (MH$^+$) 509.0.

Biological Examples

Rat Brain Delta Opioid Receptor Binding Assay

Procedure: Male, Wistar rats (150-250 g, VAF, Charles River, Kingston, N.Y.) were killed by CO$_2$, and their brains were removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM MgCl$_2$ with several brief pulses from a Polytron homogenizer. This particulate preparation was used for the delta opioid binding assays. Following incubation with the delta selective peptide ligand ~4 nM [$^3$H]DPDPE or 0.15 nM [$^3$H]naltrindole at 25° C. for 2.5 h in a 96-well plate with total volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×50 µL of Betaplate Scint scintillation fluid (LKB) was added and the radioactivity quantified on a LKB (Wallac) 1205 BetaPlate liquid scintillation counter.

Analysis: The data from the scintillation counter were used to calculate either the % inhibition compared to control binding (when only a single concentration of test compound was evaluated) or a $K_i$ value (when a range of concentrations was tested). Percent inhibition was calculated as: [(total dpm-test compound dpm)/(total dpm-nonspecific dpm)]*100. Kd and Ki values were calculated using GraphPad PRISM data analysis program.

Rat Brain Mu Opioid Receptor Binding Assay

Procedure: Male, Wistar rats (150-250 g, VAF, Charles River, Kingston, N.Y.) were killed by $CO_2$, and their brains were removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 80 mL Tris and centrifuged at 39,000×g for 10 min. The pellet was resuspended in the same volume of Tris buffer containing 5 mM $MgCl_2$ with several brief pulses from a Polytron homogenizer. This particulate preparation was used for the delta opioid binding assays. Following incubation with the mu selective peptide ligand, ~0.8 nM [$^3$H]DAMGO, at 25° C. for 2.5 h in a 96-well plate with total assay volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×40 µL of Betaplate Scint scintillation fluid (LKB) was added and the radioactivity quantifed on a LKB (Wallac) 1205 BetaPlate liquid scintillation counter.

Analysis: The data from the scintillation counter were used to calculate either the % inhibition compared to control binding (when only a single concentration of test compound was evaluated) or a $K_i$ value (when a range of concentrations tested). Percent inhibition was calculated as: [(total dpm-test compound dpm)/(total dpm-nonspecific dpm)]*100. Kd and Ki values were calculated using GraphPad PRISM data analysis program.

[$^{35}$S]GTPγS Binding Assay in NG108-15 Cell Membranes (Delta Opioid)

Methods: NG108-15 cell membranes were purchased from Applied Cell Sciences (Rockville, Md.). 8 mg/mL of membrane protein suspended in 10 mM TRIS-HCl pH 7.2, 2 mM EDTA, 10% sucrose. Membranes were maintained at 4-8° C. A 1 mL volume of membranes was added into 10 mL cold binding assay buffer. The assay buffer contained 50 mM Tris, pH 7.6, 5 mM $MgCl_2$, 100 mM NaCl, 1 mM DTT and 1 mM EGTA. The membrane suspension was homogenized twice with a Polytron, and centrifuged at 3000 rpm for 10 min. The supernatant was then centrifuged at 18,000 rpm for 20 min. Ten mL assay buffer was added into the pellet containing tube. The pellet and buffer were mixed with a Polytron.

Incubation procedure: The pellet membranes (75 µg/mL) were preincubated with SPA (10 mg/mL) at 25° C. for 45 min in the assay buffer. The SPA (5 mg/mL) coupled with membranes (37.5 µg/mL) was then incubated with 0.1 nM [$^{35}$S] GTPγS in the same Tris buffer containing 100 µM GDP in total volume of 200 µL. Increasing concentrations of receptor agonists were used to stimulate [35S]- GTPγS binding. The basal binding was tested in the absence of agonists and non-specific binding was tested in the presence of 10 µM unlabeled GTPγS. The data were analyzed on a Packard Top Count.

Data

% of Basal=(stimulated−non specific)*100/(basal−non specific).

$EC_{50}$ values were calculated using GraphPad Prism.

[$^{35}$S]GTPγS Binding Assays in CHO-hMOR Cell Membranes

Methods: CHO-hMOR cell membranes were purchased from Receptor Biology, Inc. (Baltimore, Md.). About 10 mg/mL of membrane protein was suspended in 10 mM TRIS-HCl pH 7.2, 2 mM EDTA, 10% sucrose, and the suspension kept on ice. A 1 mL volume of membranes was added to 15 mL cold binding assay buffer containing 50 mM HEPES, pH 7.6, 5 mM $MgCl_2$, 100 mM NaCl, 1 mM DTT and 1 mM EDTA. The membrane suspension was homogenized with a Polytron and centrifuged at 3,000 rpm for 10 min. The supernatant was then centrifuged at 18,000 rpm for 20 min. The pellet was resuspended in 10 mL assay buffer with a Polytron. The membranes were preincubated with wheat germ agglutinin coated SPA beads (Amersham) at 25° C. for 45 min in the assay buffer. The SPA bead (5 mg/mL) coupled membranes (10 µg/mL) were then incubated with 0.5 nM [$^{35}$S] GTPγS in the assay buffer. The basal binding was that taking place in the absence of added test compound; this unmodulated binding was considered as 100%, with agonist stimulated binding rising to levels significantly above this value. A range of concentrations of receptor agonist was used to stimulate [$^{35}$S]GTPγS binding. Both basal and non-specific binding was tested in the absence of agonist; non-specific binding determination included 10 µM unlabeled GTPγS.

Compounds were tested for function as antagonists by evaluating their potential to inhibit agonist-stimulated GTPγS binding. Radioactivity was quantified on a Packard Top-Count. The following parameters were calculated:

$$\% \text{ stimulation} = \frac{(\text{test compound } cpm - \text{non-specific } cpm)}{(\text{basal } cpm - \text{non-specific } cpm)} \times 100$$

$$\% \text{ inhibition} = \frac{(\% \text{ stimulation by } 1 \ \mu M \ DAMGO - \% \text{ stimulation by text compound})}{(\% \text{ stimulation by } 1 \ \mu M \ DAMGO - 100)} \times 100$$

$EC_{50}$ values were calculated using GraphPad Prism.

Biological Data

| Compound number | delta (Ki, nM) | mu (Ki, nM) | delta GTPgS EC50 (nM) | delta GTPgS Rel Eff |
|---|---|---|---|---|
| 10c | 0.32 | 70 | 6.4 | 0.94 |
| 9c | 0.73 | 73 | 4.6 | 1.02 |

-continued

| Compound number | delta (Ki, nM) | mu (Ki, nM) | delta GTPgS EC50 (nM) | delta GTPgS Rel Eff |
|---|---|---|---|---|
| 8c | 1.29 | 75 | 5.0 | 0.85 |
| 3l | 1.55 | 20.3535 | | |
| 11k | 3.05 | | | |
| 7c | 3.10 | 463 | 29.2 | 0.80 |
| 9l | 4.9 | | | |
| 5l | 6.51 | | | |
| 8k | 9.6115 | 27.155 | | |
| 15a | 11.1 | 1411 | 155 | 0.63 |
| 10a | 12.3 | 546 | 21.1 | 0.75 |
| 7j | 13.82 | | | |
| 7m | 17.3 | | | |
| 14a | 18.7 | 1646 | 96.9 | 0.65 |
| 11a | 19.9 | 1118 | 118.0 | 0.78 |
| 6j | 20.64 | | | |
| 7l | 21.75 | | | |
| 4l | 22.16 | | | |
| 25b | 22.355 | 775.05 | | |
| 8l | 26.57 | | | |
| 4b | 29.2 | 556 | | |
| 13b | 38.7 | 1490.5 | | |
| 12k | 39.36 | | | |
| 13a | 42 | 3021 | | |
| 10k | 45.23 | | | |
| 6l | 49.90 | | | |
| 9k | 50.26 | | | |
| 17b | 64.8 | 116 | | |
| 11b | 70.4 | 955.4 | | |
| 22b | 71.6 | 304.9 | | |
| 6h | 73 | 4705 | | |
| 14b | 78.1 | 2148 | | |
| 7d | 91 | 8202 | | |
| 21b | 98.0 | 930.15 | | |
| 23b | 99.7 | 889.7 | | |
| 15b | 102 | 947 | | |
| 16a | 114 | 2005 | | |
| 9a | 140 | 6453 | | |
| 6m | 162.30 | | | |
| 7f | 174 | 1746 | | |
| 9j | 176.06 | | | |
| 8j | 178.0 | | | |
| 2l | 179.85 | 3696.5 | | |
| 9b | 182 | 1605 | | |
| 20b | 194 | 3493 | | |
| 12a | 200 | 667 | | |
| 4m | 207.90 | | | |
| 10b | 211 | 350 | | |
| 5m | 234.2 | | | |
| 13k | 281.10 | | | |
| 7e | 294 | 43965 | | |
| 26b | 338.35 | | | |
| 8m | 348.90 | | | |
| 18b | 408 | 3198 | | |
| 7b | 426 | 6377 | | |
| 5j | 476.5 | 4776 | | |
| 7k | 655.05 | 7739.5 | | |
| 12b | 794.1 | 292.7 | | |
| 3g | 831 | 7597 | | |
| 9m | 902.7 | | | |
| 10j | 1150.75 | | | |
| 3o | 1210.5 | | | |
| 2n | 1298.70 | | | |
| 24b | 1586 | 196.1 | | |
| 14k | 2885 | 7384 | | |
| 3b | 3149 | 4443 | | |
| 6i | 3348 | >10000 | | |
| 5b | 3446 | 19695 | | |
| 8b | 4860 | 27730 | | |
| 6b | 5799 | 83165 | | |
| 17a | >10000 | >10000 | | |
| 16b | >10000 | >10000 | | |

The invention claimed is:

1. A compound of Formula (I):

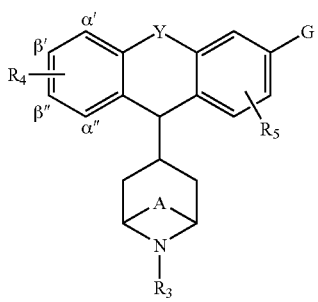

Formula (I)

wherein:

G is —C(Z)N($R_1$)$R_2$, phenyl, or a heterocycle selected from the group consisting of-tetrazolyl, oxadiazolyl, furyl, quinolinyl, thienyl, and pyridinyl; wherein phenyl and the heterocycles of G are optionally substituted with one to three substituents independently selected from the group consisting of $C_{1-8}$alkanyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, di($C_{1-8}$alkanyl)aminocarbonyl, and $C_{1-6}$alkanyloxycarbonylamino;

R1 is a substituent selected from the group consisting of hydrogen, C1-8alkanyl, $C_{2-8}$alkenyl, and $C_{2-8}$alkynyl;

$R_2$ is selected from the group consisting of hydrogen, $C_{1-4}$alkanyl and phenyl; wherein $C_{1-4}$alkanyl is optionally substituted with one to three substituents independently selected from the group consisting of phenyl, $C_{1-4}$alkanyloxy, hydroxy, fluoro, and phenoxy; and wherein any phenyl-containing substituent of $R_2$ it is optionally substituted with one to three substituents independently selected from the group consisting of $C_{1-6}$alkanyl, $C_{1-6}$alkanyloxy, fluoro, and hydroxy; or $R_1$ and $R_2$ taken together with the nitrogen to which they are attached form a pyrrolidinyl or piperidinyl ring wherein said pyrrolidinyl or piperidinyl is optionally substituted with a substituent selected from the group consisting of $C_{1-3}$alkanyl and hydroxy;

$R_3$ is selected from the group consisting of hydrogen, $C_{1-8}$alkanyl, $C_{2-8}$alkenyl, $C_{2-8}$alkynyl, $C_{1-8}$ alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-2}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, isoquinolinyl, tetrazolyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O($CH_2$)$_{1-3}$O—;

R₄ is one to three substituents independently selected from the group consisting of hydrogen, hydroxyl, methoxy, methyl, phenyl, fluoro, chloro, and bromo;

R₅ is one to two substituents independently selected from the group consisting of hydrogen, $C_{1-6}$alkanyl, $C_{2-6}$alkenyl, $C_{1-6}$alkanyloxy, amino, $C_{1-6}$alkanylamino, di($C_{1-6}$alkanyl)amino, $C_{1-6}$alkanylcarbonyl, $C_{1-6}$alkanylcarbonyloxy, $C_{1-6}$alkanyloxycarbonyl, $C_{1-6}$alkanylaminocarbonyl, $C_{1-6}$alkanylcarbonylamino, $C_{1-6}$alkanylthio, $C_{1-6}$alkanylsulfonyl, halogen, hydroxy, cyano, fluoro($C_{1-6}$)alkanyl and fluoro($C_{1-6}$)alkanyloxy;

A is —(CH2)$_m$-, wherein m is 2;

Y is O;

Z is O, S, NH, N($C_{1-6}$alkanyl), N(OH), N(O$C_{1-6}$alkanyl), or N(phenyl); and enantiomers, diastereomers, tautomers, or pharmaceutically acceptable salts thereof.

2. The compound according to claim 1 wherein G is —C(Z)N(R₁)R₂, phenyl, or a heterocycle selected from the group consisting of tetrazolyl, oxadiazolyl, furyl, quinolinyl, thienyl, and pyridinyl; wherein phenyl and the heterocycles of G are optionally substituted with one to three substituents independently selected from the group consisting of $C_{1-8}$alkanyl, $C_{1-8}$alkanyloxy, hydroxy($C_{1-8}$)alkanyl, carboxy($C_{1-8}$)alkanyl, $C_{1-8}$alkanylcarbonylamino, halogen, hydroxy, cyano, oxo, thioxo, amino, $C_{1-6}$alkanylamino, di($C_{1-6}$alkanyl)amino, $C_{1-8}$alkanylthio, aminocarbonyl, aminothiocarbonyl, $C_{1-8}$alkanylaminocarbonyl, di($C_{1-8}$alkanyl)aminocarbonyl, and $C_{1-8}$alkanyloxycarbonylamino.

3. The compound according to claim 1 wherein R₂ is selected from the group consisting of hydrogen, $C_{1-4}$alkanyl and phenyl; wherein $C_{1-4}$alkanyl is optionally substituted with one to three substituents independently selected from the group consisting of phenyl, $C_{1-4}$alkanyloxy, hydroxy, fluoro, and phenoxy; and wherein any phenyl-containing substituent of R₂ is optionally substituted with one to three substituents independently selected from the group consisting of $C_{1-6}$alkanyl, $C_{1-6}$alkanyloxy, fluoro, and hydroxy; or R₁ and R₂ taken together with the nitrogen to which they are attached form a pyrrolidinyl or piperidinyl ring wherein said pyrrolidinyl or piperidinyl is optionally substituted with a substituent selected from the group consisting of $C_{1-3}$alkanyl and hydroxy.

4. The compound according to claim 1 wherein R₃ is selected from the group consisting of hydrogen, $C_{1-8}$alkanyl, $C_{2-8}$alkenyl, $C_{2-8}$alkynyl, $C_{1-8}$alkanyloxy($C_{1-8}$)alkanyl, $C_{1-8}$alkanylthio($C_{1-8}$)alkanyl, hydroxy$C_{1-8}$alkanyl, thioformyl, phenylimino($C_{1-8}$)alkanyl, phenyl($C_{1-8}$)alkanyl, and heteroaryl($C_{1-2}$)alkanyl wherein heteroaryl is selected from the group consisting of benzo[1,3]dioxolyl, imidazolyl, furanyl, pyridinyl, thienyl, indolyl, indolinyl, isoquinolinyl, pyrazinyl, pyrazolyl, pyridazinyl, pyrimidinyl, pyrrolyl, quinolinyl, isoquinolinyl, tetrazolyl; wherein phenyl and heteroaryl are optionally substituted with one to three substituents independently selected from the group consisting of $C_{1-6}$alkanyloxy and hydroxy; or optionally, when phenyl and heteroaryl are optionally substituted with two substituents attached to adjacent carbon atoms, the two substituents together form a single fused moiety; wherein the moiety is selected from —O(CH₂)$_{1-3}$O—.

5. The compound according to claim 1 wherein:
G is —C(Z)N(R₁)R₂; tetrazolyl, furanyl, quinolinyl, thiophenyl, pyridinyl, oxadiazolyl optionally substituted with oxo; or phenyl optionally substituted with ($C_{1-8}$) alkanylcarbonylamino;
R₁ is $C_{1-4}$ alkanyl, or hydrogen;
R₂ is hydrogen or $C_{1-4}$ alkanyl;
or R₁ and R₂ taken together with the nitrogen to which they are attached form a pyrrolidinyl ring optionally substituted with hydroxy;
Z is NH or oxygen;
R₃ is pyridiny($C_{1-2}$)alkanyl, furyl($C_{1-2}$)alkanyl, $C_{1-8}$alkanyl, hydrogen, $C_{2-8}$ alkenyl, thienyl($C_{1-2}$)alkanyl, imidazolyl($C_{1-2}$)alkanyl, phenyl($C_{1-2}$)alkanyl;
R₅ is hydrogen;
A is CH₂CH₂; pyridinyl($C_{1-8}$)alkanyl, furyl($C_{1-8}$)alkanyl, thienyl($C_{1-8}$)alkanyl, imidazolyl($C_{1-8}$)alkanyl
Y is O;
Z is O or NH; and
enantiomers, diastereomers, tautomers, and pharmaceutically acceptable salts thereof.

6. The compound of claim 5 wherein when R₁ and R₂ taken together with the nitrogen to which they are attached form a pyrrolidinyl ring optionally substituted with hydroxy, Z is oxygen.

7. The compound according to claim 1 wherein:
G is —C(Z)N(R₁)R₂, 1H-tetrazol-4-yl, 4H-[1,2,4]-oxadiazol-5-oxo-3-yl, 2-methylcarbonylaminophenyl, 3-furyl, quinolin-3-yl, thiophen-3-yl, pyridin-3-yl or pyridin-4-yl;
R₁ is hydrogen, ethyl, or methyl;
R₂ is methyl, ethyl, phenethyl, or hydrogen;
or R₁ and R₂ taken together with the nitrogen to which they are attached form pyrrolidin-1-yl, 3-hydroxypyrrolidin-1-yl, or 3-(S)-hydroxypyrrolidin-1-yl;
Z is NH or oxygen, R₃ is pyridin-2-ylmethyl, fur-3-ylmethyl, methyl, hydrogen, 3-methyl-2-butenyl, thiophene-2-ylmethyl, 2-propenyl, 1H-imidazol-2-ylmethyl, 2-phenethyl, thiazol-2-ylmethyl, benzyl, or allyl;
R₅ is hydrogen
A is CH2CH2;
Y is O;
Z is O or NH; and
enantiomers, diastereomers, tautomers, and pharmaceutically acceptable salts thereof.

8. The compound according to claim 1 wherein:
G is —C(Z)N(R₁)R₂, 1H-tetrazol-4-yl, 4H-[1,2,4]-oxadiazol-5-oxo-3-yl, 2-methylcarbonylaminophenyl, 3-furyl, quinolin-3-yl, thiophen-3-yl, pyridin-3-yl or pyridin-4-yl;
R₁ is hydrogen or ethyl;
R₂ is hydrogen or ethyl;
or R₁ and R₂ taken together with the nitrogen to which they are attached form 3-hydroxypyrrolidin-1-yl;
Z is NH or oxygen;
R₃ is pyridin-2-ylmethyl, fur-3-ylmethyl, fur-2-ylmethyl, methyl, hydrogen, 3-methyl-2-butenyl, thiophene-2-ylmethyl, 2-propenyl, 1H-imidazol-2-ylmethyl, 2-phenethyl, thiazol-2-ylmethyl, allyl, or benzyl;
R₄ is hydrogen, α'-methoxy, or α'-hydroxy;
R₅ is hydrogen;
A is CH2CH2;
Y is O;
Z is O or NH; and
enantiomers, diastereomers, tautomers,-and pharmaceutically acceptable salts thereof.

9. A compound that is selected from the group consisting of:
9-(8-Aza-bicyclo[3.2.1]oct-3-yl)-9H-xanthene-3-carboxylic acid diethylamide;
9-(8-Furan-3-ylmethyl-8-aza-bicyclo[3.2.1] oct-3-ylidene)-9H-xanthene-3-carboxylic acid diethylamide;
9-(8-Benzyl-8-aza-bicyclo[3.2.1]oct-3-yl)-9H-xanthene-3-carboxylic acid diethylamide;

9-(8-Phenethyl-8-aza-bicyclo[3.2.1]oct-3-yl)-9H-xanthene-3-carboxylic acid diethylamide;
9-(8-Furan-2-ylmethyl-8-aza-bicyclo[3.2.1]oct-3-yl)-9H-xanthene-3-carboxylic acid diethylamide;
9-(8-Thiophen-2-ylmethyl-8-aza-bicyclo[3.2.1]oct-3-yl)-9H-xanthene-3-carboxylic acid diethylamide;
9-(8-Pyridin-2-ylmethyl-8-aza-bicyclo[3.2.1]oct-3-yl)-9H-xanthene-3-carboxylic acid diethylamide;
9-[8-(1H-Imidazol-2-ylmethyl)-8-aza-bicyclo[3.2.1]oct-3-yl]-9H-xanthene-3-carboxylic acid diethylamide;
8-Furan-3-ylmethyl-3-(3-pyridin-3-yl-9H-xanthen-9-yl)-8-aza-bicyclo[3.2.1]-octane;
3-(3-Thiophen-3-yl-9H-xanthen-9-yl)-8-aza-bicyclo[3.2.1]octane;
N-{2-[9-(8-Aza-bicyclo[3.2.1]oct-3-yl)-9H-xanthen-3-yl]-phenyl}-acetamide; 3-(3-Pyridin-3-yl-9H-xanthen-9-yl)-8-thiophen-2-ylmethyl-8-aza -bicyclo[3.2.1]octane;
8-Pyridin-2-ylmethyl-3-(3-pyridin-3-yl-9H-xanthen-9-yl)-8-aza -bicyclo[3.2.1]octane;
8-Benzyl-3-(3-pyridin-3-yl-9H-xanthen-9-yl)-8-aza-bicyclo[3.2.1]octane;
8-Phenethyl-3-(3-pyridin-3-yl-9H-xanthen-9-yl)-8-aza-bicyclo[3.2.1]octane; and
N-{2-[9-(8-Furan-3-ylmethyl-8-aza-bicyclo[3.2.1]oct-3-yl)-9H-xanthen-3-yl]-phenyl}-acetamide.

10. A compound that is selected from the group consisting of:
N-{2-[9-(8-Thiophen-2-ylmethyl-8-aza-bicyclo[3.2.1]oct-3-yl)-9H-xanthen-3-yl]-phenyl}-acetamide;
N-{2-[9-(8-Pyridin-2-ylmethyl-8-aza-bicyclo[3.2.1]oct-3-yl)-9H-xanthen-3-yl]-phenyl}-acetamide;
N-{2-[9-(8-Phenethyl-8-aza-bicyclo[3.2.1]oct-3-yl)-9H-xanthen-3-yl]-phenyl}-acetamide;
N-{2-[9-(8-Allyl-8-aza-bicyclo[3.2.1]oct-3-yl)-9H-xanthen-3-yl]-phenyl}-acetamide;
3-(3-Pyridin-4-yl-9H-xanthen-9-yl)-8-aza-bicyclo[3.2.1]octane;
3-(3-Pyridin-4-yl-9H-xanthen-9-yl)-8-thiophen-2-ylmethyl-8-aza-bicyclo[3.2.1]octane;
8-Pyridin-2-ylmethyl-3-(3-pyridin-4-yl-9H-xanthen-9-yl)-8-aza-bicyclo[3.2.1]octane;
8-Benzyl-3-(3-pyridin-4-yl-9H-xanthen-9-yl)-8-aza-bicyclo[3.2.1]octane;
8-Phenethyl-3-(3-pyridin-4-yl-9H-xanthen-9-yl)-8-aza-bicyclo[3.2.1]octane;
8-Furan-3-ylmethyl-3-(3-pyridin-4-yl-9H-xanthen-9-yl)-8-aza-bicyclo[3.2.1]octane;
8-(1H-Imidazol-2-ylmethyl)-3-(3-pyridin-3-yl-9H-xanthen-9-yl)-8-aza-bicyclo[3.2.1]octane;
9-(8-Aza-bicyclo[3.2.1]oct-3-yl)-5-methoxy-9H-xanthene-3-carboxylic acid diethylamide;
9-(8-Aza-bicyclo[3.2.1]oct-3-yl)-5-hydroxy-9H-xanthene-3-carboxylic acid diethylamide;
9-(8-Furan-3-ylmethyl-8-aza-bicyclo[3.2.1]oct-3-yl)-5-hydroxy-9H-xanthene-3-carboxylic acid diethylamide;
5-Hydroxy-9-[8-(1H-imidazol-2-ylmethyl)-8-aza-bicyclo[3.2.1]oct-3-yl]-9H-xanthene-3-carboxylic acid diethylamide;
9-(8-Aza-bicyclo[3.2.1]oct-3-yl)-5-phenyl-9H-xanthene-3-carboxylic acid diethylamide;
9-(8-Aza-bicyclo[3.2.1]oct-3-yl)-7-fluoro-9H-xanthene-3-carboxylic acid diethylamide;
9-(8-Aza-bicyclo[3.2.1]oct-3-yl)-7-bromo-9H-xanthene-3-carboxylic acid diethylamide; and
[9-(8-Aza-bicyclo[3.2.1]oct-3-yl)-9H-xanthen-3-yl]-pyrrolidin-1-yl-methanone.

11. A compound that is selected from the group consisting of:
9-(8-Aza-bicyclo[3.2.1]oct-3-yl)-5-methyl-9H-xanthene-3-carboxylic acid diethylamide;
3-[3-(1H-Tetrazol-5-yl)-9H-xanthen-9-yl]-8-aza-bicyclo[3.2.1]octane;
8-Furan-3-ylmethyl-3-[3-(1H-tetrazol-5-yl)-9H-xanthen-9-yl]-8-aza-bicyclo[3.2.1]octane;
3-[3-(1H-Tetrazol-5-yl)-9H-xanthen-9-yl]-8-thiophen-2-ylmethyl-8-aza-bicyclo[3.2.1]octane;
8-Pyridin-2-ylmethyl-3-[3-(1H-tetrazol-5-yl)-9H-xanthen-9-yl]-8-aza-bicyclo[3.2.1]octane;
8-Benzyl-3-[3-(1H-tetrazol-5-yl)-9H-xanthen-9-yl]-8-aza-bicyclo[3.2.1]octane;
8-Phenethyl-3-[3-(1H-tetrazol-5-yl)-9H-xanthen-9-yl]-8-aza-bicyclo[3.2.1]octane;
3-(5-Methoxy-3-pyridin-3-yl-9H-xanthen-9-yl)-8-aza-bicyclo[3.2.1]octane;
9-(8-Aza-bicyclo[3.2.1]oct-3-yl)-6-pyridin-3-yl-9H-xanthen-4-ol;
9-(8-Furan-3-ylmethyl-8-aza-bicyclo[3.2.1]oct-3-yl)-6-pyridin-3-yl-9H-xanthen-4-ol;
6-Pyridin-3-yl-9-(8-thiophen-2-ylmethyl-8-aza-bicyclo[3.2.1]oct-3-yl)-9H-xanthen-4-ol;
6-Pyridin-3-yl-9-(8-pyridin-2-ylmethyl-8-aza-bicyclo[3.2.1]oct-3-yl)-9H-xanthen-4-ol;
9-(8-Benzyl-8-aza-bicyclo[3.2.1]oct-3-yl)-6-pyridin-3-yl-9H-xanthen-4-ol;
9-(8-Phenethyl-8-aza-bicyclo[3.2.1]oct-3-yl)-6-pyridin-3-yl-9H-xanthen-4-ol;
3-(3-Bromo-5-methoxy-9H-xanthen-9-yl)-8-aza-bicyclo[3.2.1]octane;
N-{2-[9-(8-Aza-bicyclo[3.2.1]oct-3-yl)-5-methoxy-9H-xanthen-3-yl]-phenyl}-acetamide;
N-{2-[9-(8-Aza-bicyclo[3.2.1]oct-3-yl)-5-hydroxy-9H-xanthen-3-yl]-phenyl}acetamide;
N-{2-[9-(8-Furan-3-ylmethyl-8-aza-bicyclo[3.2.1]oct-3-yl)-5-hydroxy-9H-xanthen-3-yl]-phenyl}-acetamide; and
N-{2-[5-Hydroxy-9-(8-thiophen-2-ylmethyl-8-aza-bicyclo[3.2.1]oct-3-yl)-9H-xanthen-3-yl]-phenyl}-acetamide.

12. A compound that is selected from the group consisting of
N-{2-[5-Hydroxy-9-(8-pyridin-2-ylmethyl-8-aza-bicyclo[3.2.1]oct-3-yl)-9H-xanthen-3-yl]-phenyl}-acetamide;
N-{2-[9-(8-Benzyl-8-aza-bicyclo[3.2.1]oct-3-yl)-5-hydroxy-9H-xanthen-3-yl]-phenyl}-acetamide;
N-{2-[5-Hydroxy-9-(8-phenethyl-8-aza-bicyclo[3.2.1]oct-3-yl)-9H-xanthen-3-yl]-phenyl}-acetamide;
N-(2-{5-Hydroxy-9-[8-(1H-imidazol-2-ylmethyl)-8-aza-bicyclo[3.2.1]oct-3-yl]-9H-xanthen-3-yl}-phenyl)-acetamide;
9-(8-Aza-bicyclo[3.2.1]oct-3-yl)-N,N-diethyl-9H-xanthene-3-carboxamidine;
N,N-Diethyl-9-(8-furan-3-ylmethyl-8-aza-bicyclo[3.2.1]oct-3-yl)-9H-xanthene-3-carboxamidine;
N,N-Diethyl-9-(8-thiophen-2-ylmethyl-8-aza-bicyclo[3.2.1]oct-3-yl)-9H-xanthene-3-carboxamidine;
N,N-Diethyl-9-(8-pyridin-2-ylmethyl-8-aza-bicyclo[3.2.1]oct-3-yl)-9H-xanthene-3-carboxamidine;
9-(8-Benzyl-8-aza-bicyclo[3.2.1]oct-3-yl)—N,N-diethyl-9H-xanthene-3-carboxamidine;
N,N-Diethyl-9-(8-phenethyl-8-aza-bicyclo[3.2.1]oct-3-yl)-9H-xanthene-3-carboxamidine;
3-(9-Piperidin-4-yl-9H-xanthen-3-yl)-4H-[1,2,4]oxadiazol-5-one;

3-[9-(1-Furan-3-ylmethyl-piperidin-4-yl)-9H-xanthen-3-yl]-4H-[1,2,4]oxadiazol-5-one;

3-[9-(8-Pyridin-2-ylmethyl-8-aza-bicyclo[3.2.1]oct-3-yl)-9H-xanthen-3-yl]-4H-[1,2,4]oxadiazol-5-one;

[9-(8-Aza-bicyclo[3.2.1]oct-3-yl)-9H-xanthen-3-yl]-(3-hydroxy-pyrrolidin-1-yl)-methanone;

[9-(8-Furan-3-ylmethyl-8-aza-bicyclo[3.2.1]oct-3-yl)-9H-xanthen-3-yl]-(3-hydroxy-pyrrolidin-1-yl)-methanone;

(3-Hydroxy-pyrrolidin-1-yl)-[9-(8-thiophen-2-ylmethyl-8-aza-bicyclo[3.2.1]oct-3-yl)-9H-xanthen-3-yl]-methanone;

(3-Hydroxy-pyrrolidin-1-yl)-[9-(8-pyridin-2-ylmethyl-8-aza-bicyclo[3.2.1]oct-3-yl)-9H-xanthen-3-yl]-methanone;

[9-(8-Benzyl-8-aza-bicyclo[3.2.1]oct-3-yl)-9H-xanthen-3-yl]-(3-hydroxy-pyrrolidin-1-yl)-methanone; and (3-Hydroxy-pyrrolidin-1-yl)-[9-(8-phenethyl-8-aza-bicyclo[3.2.1]oct-3-yl)-9H-xanthen-3-yl]-methanone.

13. A compound that is selected from the group consisting of:

5-Hydroxy-9-[8-(1H-imidazol-2-ylmethyl)-8-aza-bicyclo[3.2.1]oct-3-yl]-9H-xanthene-3-carboxylic acid diethylamide;

9-(8-Furan-3-ylmethyl-8-aza-bicyclo[3.2.1]oct-3-yl)-5-hydroxy-9H-xanthene-3-carboxylic acid diethylamide;

9-(8-Aza-bicyclo[3.2.1]oct-3-yl)-5-hydroxy-9H-xanthene-3-carboxylic acid diethylamide;

N-{2-[9-(8-Aza-bicyclo[3.2.1]oct-3-yl)-5-hydroxy-9H-xanthen-3-yl]-phenyl}-acetamide;

6-Pyridin-3-yl-9-(8-pyridin-2-ylmethyl-8-aza-bicyclo[3.2.1]oct-3-yl)-9H-xanthen-4-ol;

9-(8-Aza-bicyclo[3.2.1]oct-3-yl)-5-methoxy-9H-xanthene-3-carboxylic acid diethylamide;

N-(2-{5-Hydroxy-9-[8-(1H-imidazol-2-ylmethyl)-8-aza-bicyclo[3.2.1]oct-3-yl]-9H-xanthen-3-yl}-phenyl)-acetamide;

N-{2-[5-Hydroxy-9-(8-thiophen-2-ylmethyl-8-aza-bicyclo[3.2.1]oct-3-yl)-9H-xanthen-3-yl]-phenyl}-acetamide; and 9-(8-Aza-bicyclo[3.2.1]oct-3-yl)-6-pyridin-3-yl-9H-xanthen-4-ol.

14. A composition comprising the dextrorotatory enantiomer of a compound according to claim 1 wherein said composition is substantially free from the levorotatory isomer of said compound.

15. A composition comprising the levororotatory enantiomer of a compound according to claim 1 wherein said composition is substantially free from the dextrorotatory isomer of said compound.

16. A composition comprising the exo isomer of a compound according to claim 1 wherein said composition is substantially free from the endo isomer of said compound.

17. A composition comprising the endo isomer of a compound according to claim 1 wherein said composition is substantially free from the exo isomer of said compound.

18. A pharmaceutical composition comprising a compound or salt according to claim 1 admixed with a pharmaceutically acceptable carrier, excipient or diluent.

19. A compound that is selected from the group consisting of:

9-(8-Aza-bicyclo[3.2.1]oct-3-yl)-5-chloro-9H-xanthene-3-carboxylic acid diethylamide;

3-(3-Pyridin-3-yl-9H-xanthen-9-yl)-8-aza-bicyclo[3.2.1]octane;

3-(3-Furan-3-yl-9H-xanthen-9-yl)-8-aza-bicyclo[3.2.1]octane; and

3-[9-(8-Aza-bicyclo[3.2.1]oct-3-yl)-9H-xanthen-3-yl]-quinoline.

* * * * *